US008470793B2

(12) United States Patent
Fishelson et al.

(10) Patent No.: US 8,470,793 B2
(45) Date of Patent: *Jun. 25, 2013

(54) DOWN-REGULATION OF MORTALIN BY SIRNA

(75) Inventors: Zvi Fishelson, Tel-Aviv (IL); David Pilzer, Holon (IL)

(73) Assignee: Ramot at Tel-Aviv University Ltd., Tel-Aviv (IL)

( * ) Notice: Subject to any disclaimer, the term of this patent is extended or adjusted under 35 U.S.C. 154(b) by 270 days.

This patent is subject to a terminal disclaimer.

(21) Appl. No.: 12/679,938

(22) PCT Filed: Sep. 25, 2008

(86) PCT No.: PCT/IL2008/001295
§ 371 (c)(1),
(2), (4) Date: Jun. 29, 2010

(87) PCT Pub. No.: WO2009/040819
PCT Pub. Date: Apr. 2, 2009

(65) Prior Publication Data
US 2010/0278841 A1    Nov. 4, 2010

Related U.S. Application Data

(60) Provisional application No. 60/960,311, filed on Sep. 25, 2007.

(51) Int. Cl.
C12N 15/11      (2006.01)
G01N 33/53      (2006.01)
A61K 39/395     (2006.01)

(52) U.S. Cl.
USPC ............... 514/44 A; 536/24.5; 530/387.7; 424/138.1; 436/512

(58) Field of Classification Search
None
See application file for complete search history.

(56) References Cited

U.S. PATENT DOCUMENTS

| | | | |
|---|---|---|---|
| 5,627,039 | A | 5/1997 | Pereira-Smith et al. |
| 5,670,530 | A | 9/1997 | Chen et al. |
| 2001/0018041 | A1 | 8/2001 | Hanna et al. |
| 2003/0228294 | A1 | 12/2003 | Dang et al. |
| 2005/0112130 | A1 | 5/2005 | Bhat et al. |
| 2005/0164231 | A1 | 7/2005 | Staudt et al. |
| 2005/0281815 | A1 | 12/2005 | Eshel et al. |
| 2006/0270622 | A1 | 11/2006 | Fishelson et al. |

FOREIGN PATENT DOCUMENTS

| | | |
|---|---|---|
| EP | 0527494 | 2/1993 |
| WO | WO 01/80884 | 11/2001 |
| WO | WO 02/12194 | 2/2002 |
| WO | WO 2004/072027 | 8/2004 |
| WO | WO 2006/022344 | 3/2006 |
| WO | WO 2008/032324 | 3/2008 |
| WO | WO 2008/156012 | 12/2008 |
| WO | WO 2009/040819 | 4/2009 |

OTHER PUBLICATIONS

Garrido et al. Heat shock proteins 27 and 70. Cell Cycle 2006, vol. 5, No. 22, pp. 2592-2601.*
Official Action Dated Sep. 20, 2011 From the US Patent and Trademark Office Re.: U.S. Appl. No. 11/440,132.
Chanan-Khan et al. "Bcl-2 Antisense Therapy in B-Cell Malignant Proliferative Disorders", Current Treatment Options in Oncology, 5: 261-267, 2004.
Official Actiion Dated Nov. 26, 2007 From the US Patent and Trademark Office Re.: U.S. Appl. No. 11/440,132.
Official Action Dated May 5, 2008 From the US Patent and Trademark Office Re.: U.S. Appl. No. 11/440,132.
Official Action Dated Jan. 13, 2009 From the US Patent and Trademark Office Re.: U.S. Appl. No. 11/440,132.
Official Action Dated Mar. 28, 2007 From the US Patent and Trademark Office Re.: U.S. Appl. No. 11/440,132.
International Search Report Dated Mar. 25, 2009 From the International Search Authority Re.: Application No. PCT/IL2008/001295.
International Search Report Dated Mar. 28, 2008 From the International Searching Authority Re.: Application No. PCT/IL2007/001132.
Official Action Dated Aug. 3, 2009 From the US Patent and Trademark Office Re.: U.S. Appl. No. 11/440,132.
Official Action Dated Aug. 22, 2008 From the US Patent and Trademark Office Re.: U.S. Appl. No. 11/440,132.
Official Action Dated Nov. 26, 2007 From the US Patent and Trademark Office Re.: U.S. Appl. No. 11/440,132.
Official Action Dated Jan. 29, 2007 From the US Patent and Trademark Office Re.: U.S. Appl. No. 11/440,132.
Response Dated Feb. 3, 2010 to Official Action of Aug. 3, 2009 From the US Patent and Trademark Office Re.: U.S. Appl. No. 11/440,132.
Response Dated Sep. 26, 2007 to Official Action of Mar. 28, 2007 From the US Patent and Trademark Office Re.: U.S. Appl. No. 11/440,132.
Written Opinion Dated Mar. 25, 2009 From the International Searching Authority Re.: Application No. PCT/IL2008/001295.
Written Opinion Dated Mar. 28, 2008 From the International Searching Authority Re.: Application No. PCT/IL2007/001132.
Bhattacharyya et al. "Cloning and Subcellular Localization of Human Mitochondrial Hsp70", The Journal of Biological Chemistry, 270(4): 1705-1710, Jan. 27, 1995.
Bindon et al. "Human Monoclonal IgG Isotypes Differ in Complement Activating Function at the Level of C4 as Well as C1q", Journal of Experimental Medicine, 168: 127-142, Jul. 1988.
Bohana-Kashtan et al. "Cell Signals Transduced by Complement", Molecular Immunology, 41: 583-597, 2004.
Britten et al. "A Phase I and Pharmacokinetic Study of the Mitochondrial-Specific Rhodacyanine Dye Analog MKT 077", Clinical Cancer Research, 6: 42-49, 2000. Abstract, Results at p. 45, Discussion at p. 47, p. 48, 2nd Col., Last §, p. 49, 1st §.

(Continued)

Primary Examiner — Shafiqul Haq

(57) ABSTRACT

Use of a siRNA molecule selected from the group consisting of SEQ ID NO: 173 to 344 for treating a disease associated with a pathological cell population in a subject in need thereof is disclosed. Pharmaceutical compositions and articles of manufacture comprising the siRNAs are also disclosed.

1 Claim, 8 Drawing Sheets

OTHER PUBLICATIONS

Carette et al. "Implication of PbP74/Mortalin/GRP75 in the Radio-Adaptive Response", International Journal of Radiation Biology, 78(3): 183-190, 2002.
Carney et al. "Elimination of Terminal Complement Complexes in the Plasma Membrane of Nucleated Cells: Influence of Extracellular Ca2+ and Association With Cellular Ca2+", The Journal of Immunology, 137(1): 263-270, 1986.
Carney et al. "Elimination of Terminal Complement Intermediates From the Plasma Membrane of Nucleated Cells: The Rate of Disappearance Differs for Cells Carrying C5b-7 or C5b-8 or a Mixture of C5b-8 With a Limited Number of C5b-9", The Journal of Immunology, 134( 3): 1804-1809, 1985.
Cragg et al. "Complement Mediated Cell Death Is Associated With DNA Fragmentation", Cell Death and Differentiation, 7: 48-58, 2000.
Curtis "New Monoclonal Antibodies for Hematologic Malignancies ( and Breast Cancer)", Medicine and Health, Rode Island, 86: 256-257, 2003.
Dashiell et al. "Terminal Complement Complexes Concomitantly Stimulate Proliferation and Rescue of Schwann Cells From Apoptosis", GLIA, 30(2): 187-198, 2000.
Deocaris et al. "Mortalin Sensitizes Human Cancer Cells to MKT-077-Induced Senescence", Cancer Letters, XP025319755, 252(2): 259-269, Jul. 18, 2007. p. 263, Fig.1, Abstract.
Devi "SiRNA-Based Approaches in Cancer Therapy", Comprehensive Cancer Center, Duke University Medical Center, Durham, NC, Cancer Gene Therapy, 13: 819-829, 2006.
Doolittle "State of the Science in Brain Tumor Classification", Seminar in Oncology Nursing, 20(4): 224-230, Nov. 2004.
Dundas et al. "Mortalin Is Over-Expressed by Colorectal Adenocarcinomas and Correlates With Poor Survival", Journal of Pathology, 205: 74-81, 2005.
Fishelson et al. "Contribution of Heat Shock Proteins to Cell Protection From Complement-Mediated Lysis", International Immunology, 13(8): 983-991, 2001.
Fishelson et al. "Obstacles to Cancer Immunotherapy: Expression of Membrane Complement Regulatory Proteins (mCRPs) in Tumors", Molecular Immunology, 40: 109-123, 2003.
Gadjeva et al. "Interaction of Human C1q With IgG and IgM: Revisited", Biochemistry, 47(49): 13093-13102, 2008.
Gelderman et al. "The Inhibitory Effect of CD46, CD55, and CD59 on Complement Activation After Immunotherapeutic Treatment of Cervical Carcinoma Cells With Monoclonal Antibodies or Bispecific Monoclonal Antibodies", Laboratory Investigation, 82(4): 483-493, 2002.
Gelderman et al. "Tumor-Specific Inhibition of Membrane-Bound Complement Regulatory Protein Crry With Bispecific Monoclonal Antibodies Prevents Outgrowth in a Rat Colorectal Cancer Lung Metastases Model", Cancer Research, 64: 4300-4372, 2004.
Gralinski et al. "Heat Stress Protects the Perfused Rabbit Heart From Complement-Mediated Injury", AJP—Heart and Circulatory Physiology, 271(2): H571-H578, 1996. Abstract.
Harris "Monoclonal Antibodies as Therapeutic Agents for Cancer", The Lancet Oncology, 5: 292-302, 2004.
Harris et al. "Tumour Cell Killing Using Chemically Engineered Antibody Constructs Specific for Tumour Cells and the Complement Inhibitor CD59", Clinical and Experimental Immunology, 107: 364-371, 1997.
Houshmand et al. "Targeting Tumor Cells", Current Opinion in Cell Biology, 15: 640-644, 2003.
Johannesen et al. "Is Mortalin a Candidate Gene for T1DM?", Autoimmunity, 37(6/7): 423-430, 2004.
Jurianz et al. "K562 Erythroleukemic Cells Are Equipped With Multiple Mechanisms of Resistance to Lysis by Compliment", International Journal of Cancer, 93: 848-854, 2001.
Kaul et al. "Overexpressed Mortalin (Mot-2)/Mthsp70/GRP75 and hTERT Cooperate to Extend the In Vivo Lifespan of Human Fibroblasts", Experimental Cell Research, 286: 96-101, 2003.
Kirmanoglou et al. "Expression of Mortalin in Patients With Chronic Atrial Fibrillation", Basic Research in Cardiology, 99: 404-408, 2004.
Koski et al. "Cytolysis of Nucleated Cells by Complement: Cell Death Displays Multi-Hit Characteristics", Proc. Natl. Acad. Sci. USA, 80: 3816-3820, 1983.
Kregel et al. "Molecular Biology and Thermoregulation, Invited Review: Heat Shock Proteins: Modifying Factors in Physiological Stress Responses and Acquired Thermotolerance", Journal of Applied Physiology, 92: 2177-2186, 2002.
Lucisano Valim et al. "The Effect of Antibody Isotype and Antigenic Epitope Density on the Complement-Fixing Activity of Immune Complexes: A Systematic Study Using Chimaeric Anti-NIP Antibodies With Human Fc Regions", Clinical & Experimental Immunology, 84: 1-8, 1991.
Mansoor et al. "Potentiation of the Antiproliferative Activity of MKT-077 by Loperamide, Diltiazem and Tamoxifen", Oncology Reports 2003, 10(6): 2023-2026, 2003, Database Medline [Online], US National Library of Medicine (NLM), Database Accession No. NLM14534737. Abstract.
Modica-Napolitano et al. "The Selective In Vitro Cytotoxicity of Carcinoma Cells by AZT Is Enhanced by Concurrent Treatment With Delocalized Lipophilic Cations", Cancer Letters, 198(1): 59-68, 2003. Abstract, Figs.3, 4, Introduction, P.59, 60, p. 66, 1st Col., Last §, p. 67, 1st §.
Morgan et al. "Complement Lysis of U937, A Nucleated Mammalian Cell Line in the Abesence of C9: Effect of C9 on C5b-8 Mediated Cell Lysis", The Journal of Immunology, 136(9): 3402-3406, 1986.
Morgan et al. "Recovery of Human Neutrophils From Complement Attack: Removal of the Membrane Attack Complex by Endocytosis and Exocytosis", The Journal of immunology, 138(1): 246-253, 1987.
Ohtsuka et al. "Mortalin Is a Novel Mediator of Erythropoietin Signaling", European Journal of Haematology, XP002519032, 79(2): 114-125, Aug. 2007.
Pilzer et al. "Mortalin/GRP75 Promotes Release of Membrane Vesicles From Immune Attacked Cells and Protection From Complement-Mediated Lysis", International Immunology, 17(9): 1239-1248, 2005. Abstract.
Propper et al. "Phase I Trial of the Selective Mitochondrial Toxin MKT 077 in Chemo-Resistant Solid Tumours", Annals of Oncology, 10: 923-927, 1999.
Ran et al. "Extramitochondrial Localization of Mortalin/Mthsp70/PBP74/GRP75", Biochemical and Biophysical Research Communications, 275: 174-179, 2000.
Reiter et al. "Sublytic Complement Attack Protects Tumor Cells From Lytic Doses of Antibody and Complement", European Journal of Immunology, 22(5): 1207-1213, 1992. Abstract.
Rüdiger et al. "Modulation of Substrate Specificity of the DnaK Chaperone by Alteration of a Hydrophobic Arch", Journal of Molecular Biology, 304: 245-251, 2000.
Schmidt "Negotiating the RNAi Patent Thicket", Nature Biotechnology, 25(3): 273-275, 2007.
Scolding et al. "Vesicular Removal by Oligodendrocytes of Membrane Attack Complexes Formed by Activated Complement", Nature, 339: 620-622, 1989.
Shin et al. "Global Profiling of the Cell Surface Proteome of Cancer Cells Uncovers an Abundance of Proteins With Chaperone Function", The Journal of Biological Chemistry, 278(9): 7607-7616, 2003.
Sims et al. "Repolarization of the Membrane Potential of Blood Platelets After Complement Damage: Evidence for a Ca++—Dependent Exocytotic Elimination of C5b-9 Pores", Blood, 68(2): 556-561, 1986.
Stein et al. "Ectocytosis Caused by Sublytic Autologous Complement Attack on Human Neutrophils", Biochemical Journal, 274: 381-386, 1991.
Takano et al. "Elevated Levels of Mortalin Expression in Human Brain Tumors", Experimental Cell Research, 237: 38-45, 1997.
Takashima et al. "Proteomic Profiling of Heat Shock Protein 70 Family Members as Biomarkers for Hepatitis C Virus-Related Hepatocellular Carcinoma", Proteomics, 3: 2487-2493, 2003.
Takashita et al. "Therapeutic Potential of RNA Interference Against Cancer", Cancer Science, 97(8): 689-696, 2006.
Tavaria et al. "A Hitchhiker's Guide to the Human Hsp70 Family", Cell Stress & Chaperones, 1(1): 23-28, 1996.

VanBuskirk et al. "Cellular and Subcellular Distribution of PBP72/74, A Peptide-Binding Protein That Plays a Role in Antigen Processing", The Journal of Immunology, 146(2): 500-506, 1991.

Vickers et al. "Efficient Reduction of Target RNAs by Small Interfering RNA and RNase H-Dependent Antisense Agents", The Journal of Biological Chemistry, 278(9): 7108-7118, 2003.

Voisine et al. "The Protein Import Motor of Mitochondria: Unfolding and Trapping of Preproteins Are Distinct and Separable Functions of Matrix Hsp70", Cell, 97: 565-574, 1999.

Wadhwa et al. "An Hsp70 Family Chaperone, Mortalin/Mthsp70/PBP74/Grp75: What, When, and Where?", Cell Stress & Chaperones, 7(3): 309-316, 2002.

Wadhwa et al. "Cellular Mortality to Immortalization: Mortalin", Cell Structure and Function, 19(1): 1-10, 1994.

Wadhwa et al. "Mortalin: A Potential Candidate for Biotechnology and Biomedicine", Histology and Histopathology, 17(4): 1173-1177, 2002. Abstract.

Wadhwa et al. "Reduction in Mortalin Level by Its Antisense Expression Causes Senescence-Like Growth Arrest in Human Immortalized Cells", The Journal of Gene Medicine, 6(4): 439-444, 2004.

Wadhwa et al. "Rhodacyanine Dye MKT-077 Inhibits In Vitro Telomerase Assay But Has No Detectable Effects on Telomerase Activity In Vivo", Cancer Research, 62: 4434-4438, 2002.

Wadhwa et al. "Selective Toxicity of MKT-077 to Cancer Cells Is Mediated by Its Binding to the Hsp70 Family Protein Mot-2 and Reactivation of P53 Function", Cancer Research, 60(24): 6818-6821, 2000.

Wadhwa et al. "Targeting Mortalin Using Conventional and RNA Helicase-Coupled Hammer-head Ribozymes", EMBO Reports, 4(6): 596-601, 2003.

Wadhwa et al. "Upregulation of Mortalin/Mthsp70/Grp75 Contributes to Human Carcinogenesis", International Journal of Cancer, 118: 2973-2980, 2006.

Walport "Complement", New England Journal of Medicine, 344(14): 1058-1066, 2001.

Zhou et al. "The Role of Complement in the Mechanism of Action of Rituximab for B-Cell Lymphoma: Implications for Therapy", The Oncologist, 13: 954-966, 2008.

Restriction Official Action Dated Dec. 19, 2011 From the US Patent and Trademark Office Re. U.S. Appl. No. 12/310,790.

Tatsuta et al. "Pharmacokinetic Analysis and Antitumor Efficacy of MKT-077, A Novel Antitumor Agent", Cancer Chemotherapy and Pharmacology, 43(4): 295-301, 1999.

Cullen "RNA Interference: Antiviral Defense and Genetic Tool", Nature Immunology, 3(7): 597-599, Jul. 2002.

Applicant-Initiated Interview Summary Dated Feb. 21, 2012 From the US Patent and Trademark Office Re.: U.S. Appl. No. 11/440,132.

Official Action Dated May 12, 2010 From the US Patent and Trademark Office Re.: U.S. Appl. No. 11/440,132.

Pilzer et al. "Mortalin Inhibitors Sensitize K562 Leukemia Cells to Complement-Dependent Cytotoxicity", International Journal of Cancer, 126: 1428-1435, 2010.

Notice of Non-Compliant Amendment Dated Jul. 29, 2011 From the US Patent and Trademark Office Re. U.S. Appl. No. 11/440,132.

International Preliminary Report on Patentability Dated Apr. 8, 2010 From the International Bureau of WIPO Re.: Application No. PCT/IL2008/001295.

Response Dated Mar. 28, 2010 to Official Action of Aug. 3, 2009 From the US Patent and Trademark Office Re.: U.S. Appl. No. 11/440,132.

Official Action Dated Apr. 19, 2012 From the US Patent and Trademark Office Re.: U.S. Appl. No. 11/440,132.

Response Dated Nov. 12, 2010 to Official Action of May 12, 2010 From the US Patent and Trademark Office Re.: U.S. Appl. No. 11/440,132.

Bernstein et al. "Role for a Bidentate Ribonuclease in the Initiation Step of RNA Interference", Nature, 409: 363-366, Jan. 18, 2001.

Brantl "Antisense-RNA Regulation and RNA Interference", Biochimica et Biophysica Acta, 1575: 15-25, 2002.

Brinker et al. "Ligand Discrimination by TPR Domains. Relevance and Selectivity of EEVD-Recognition in Hsp70•Hop•Hsp90 Complexes", The Journal of Biological Chemistry, 277(22): 19265-19275, May 31, 2002.

Hammond et al. "Post-Transcriptional Gene Silencing by Double-Stranded RNA", Nature Reviews Genetics, 2: 110-111, Feb. 2001.

Hutvágner et al. "RNAi: Nature Abhors a Double-Strand", Current Opinion in Genetics & Development, 12: 225-232, 2002.

Nucleotide "Homo Sapiens Heat Shock 70kDa Protein 9 (Mortalin) (IISPA9), Nuclear Gene Encoding Mitochondrial Protein, mRNA", Nucleotide Results, NCBI Reference Sequence: NM_004134.6, Accession No. NM_004134, 2010.

Nucleotide "Homo Sapiens Heat Shock 70kDa Protein 9B (Mortalin-2) (HSPA9B), Nuclear Gene Encoding Mitochondrial Protein, mRNA", Nucleotide Results, NCBI Reference Sequence: NM_004134.3, Accession No. NM_004134, 2003.

Odunuga et al. "Tetratricopeptide Repeat Motif-Mediated Hsc70-mSTI1 Interaction", The Journal of Biological Chemistry, 278(9): 6896-6904, Feb. 28, 2003.

Protein "Stress-70 Protein, Mitochondrial Precursor [Homo Sapiens]", Protein Results, NCBI Reference Sequence: NP_004125.3, Accession No. NP_004125, 2010.

Sadekova et al. "Induction of PBP74/Mortalin/Grp75, A member of the Hsp70 Family, by Low Doses of Ionizing Radiation: A Possible Role in Induced Radioresistance", International Journal of Radiation Biology, 72(6): 653-660, Dec. 1997. Abstract.

Sharp "RNA Interference—2001", Genes & Development, 15: 485-490, 2001.

Tuschl "RNA Interference and Small Interfering RNAs", ChemBiochem, 2: 239-245, 2001.

Yaguchi et al. "Involvement of Mortalin in Cellular Senescence From the Perspective of Its Mitochondrial Import, Chaperone, and Oxidative Stress Management Functions", Annals of the New York Academy of Sciences, 1100: 306-311, 2007.

* cited by examiner

SEQUENCE LISTING

```
<160> NUMBER OF SEQ ID NOS: 350

<210> SEQ ID NO 1
<211> LENGTH: 21
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 1
tgcctcgtac tcctccattt a                                            21

<210> SEQ ID NO 2
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 2
```

```
tggccttagt catgaggct                                              19
```

<210> SEQ ID NO 3
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 3

```
ggcgggatta tgcatcaga                                              19
```

<210> SEQ ID NO 4
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 4

```
gcaatcaagg gagcagttg                                              19
```

<210> SEQ ID NO 5
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 5

```
tcaagggagc agttgttgg                                              19
```

<210> SEQ ID NO 6
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 6

```
gggagcagtt gttggtatt                                              19
```

<210> SEQ ID NO 7
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 7

```
ctcctgcgtg gcagttatg                                              19
```

<210> SEQ ID NO 8
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 8

```
tggcagttat ggaaggtaa                                              19
```

<210> SEQ ID NO 9
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 9
ggtaaacaag caaaggtgc                                              19

<210> SEQ ID NO 10
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 10
acaagcaaag gtgctggag                                              19

<210> SEQ ID NO 11
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 11
gcaaaggtgc tggagaatg                                              19

<210> SEQ ID NO 12
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 12
aggtgctgga gaatgccga                                              19

<210> SEQ ID NO 13
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 13
tgccgaaggt gccagaacc                                              19

<210> SEQ ID NO 14
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 14
ggtgccagaa ccacccctt                                              19

<210> SEQ ID NO 15

```
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 15
ccaccccttc agttgtggc                                                19

<210> SEQ ID NO 16
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 16
gcgacaggct gtcaccaac                                                19

<210> SEQ ID NO 17
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 17
aattgtccgt gcctccaat                                                19

<210> SEQ ID NO 18
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 18
ttgtccgtgc ctccaatgg                                                19

<210> SEQ ID NO 19
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 19
tggtgatgcc tgggttgag                                                19

<210> SEQ ID NO 20
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 20
attgtattct ccgagtcag                                                19

<210> SEQ ID NO 21
<211> LENGTH: 19
<212> TYPE: DNA
```

<213> ORGANISM: Homo sapiens
<220> FEATURE:
<221> NAME/KEY: misc_feature
<223> OTHER INFORMATION: Mortalin target sequence for siRNA silencing

<400> SEQUENCE: 21
gagtcagatt ggagcattt                                           19

<210> SEQ ID NO 22
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 22
gagcatttgt gttgatgaa                                           19

<210> SEQ ID NO 23
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 23
gatgaaagag actgcagaa                                           19

<210> SEQ ID NO 24
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 24
agagactgca gaaaattac                                           19

<210> SEQ ID NO 25
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 25
aattacttgg ggcacacag                                           19

<210> SEQ ID NO 26
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 26
ttacttgggg cacacagca                                           19

<210> SEQ ID NO 27
<211> LENGTH: 19
<212> TYPE: DNA
<213> ORGANISM: Homo sapiens
<220> FEATURE:

<220> FEATURE:
<221> NAME/KEY: misc_feature
<223> OTHER INFORMATION: Mortalin target sequence for siRNA silencing

<400> SEQUENCE: 27
aaaatgctgt gatcacagt                                                19

<210> SEQ ID NO 28
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 28
aatgctgtga tcacagtcc                                                19

<210> SEQ ID NO 29
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 29
tgctgtgatc acagtccca                                                19

<210> SEQ ID NO 30
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 30
tgactcgcag agacaggcc                                                19

<210> SEQ ID NO 31
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 31
agatgctggc cagatatct                                                19

<210> SEQ ID NO 32
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 32
tgtgcttcgg gtgattaat                                                19

<210> SEQ ID NO 33
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

```
<400> SEQUENCE: 33
tgagcccaca gctgctgct                                                    19

<210> SEQ ID NO 34
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 34
tgcctatggt ctagacaaa                                                    19

<210> SEQ ID NO 35
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 35
agacaaatca gaagacaaa                                                    19

<210> SEQ ID NO 36
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 36
gacaaagtca ttgctgtat                                                    19

<210> SEQ ID NO 37
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 37
tgatttaggt ggtggaact                                                    19

<210> SEQ ID NO 38
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 38
ggaaattcag aaaggagta                                                    19

<210> SEQ ID NO 39
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 39
```

```
aggagtattt gaggtgaaa                                          19

<210> SEQ ID NO 40
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 40
atccacaaat ggggatacc                                          19

<210> SEQ ID NO 41
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 41
atggggatac cttcttagg                                          19

<210> SEQ ID NO 42
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 42
gactttgacc aggccttgc                                          19

<210> SEQ ID NO 43
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 43
ggagttcaag agagagaca                                          19

<210> SEQ ID NO 44
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 44
gagagagaca ggggttgat                                          19

<210> SEQ ID NO 45
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 45
agacaacatg gcacttcag                                          19
```

```
<210> SEQ ID NO 46
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 46
catggcactt cagagggta                                                       19

<210> SEQ ID NO 47
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 47
gctgctgaaa aggctaaat                                                       19

<210> SEQ ID NO 48
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 48
aaggctaaat gtgaactct                                                       19

<210> SEQ ID NO 49
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 49
ggctaaatgt gaactctcc                                                       19

<210> SEQ ID NO 50
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 50
atgtgaactc tcctcatct                                                       19

<210> SEQ ID NO 51
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 51
ctctcctcat ctgtgcaga                                                       19
```

```
<210> SEQ ID NO 52
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 52
tttgccctat cttacaatg                                                19

<210> SEQ ID NO 53
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 53
tggattcttc tggacccaa                                                19

<210> SEQ ID NO 54
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 54
ggacccaagc atttgaata                                                19

<210> SEQ ID NO 55
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 55
tatgaagttg acccgtgct                                                19

<210> SEQ ID NO 56
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 56
gttgacccgt gctcaattt                                                19

<210> SEQ ID NO 57
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 57
tttgaaggga ttgtcactg                                                19

<210> SEQ ID NO 58
<211> LENGTH: 19
```

```
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 58
gggattgtca ctgatctaa                                              19

<210> SEQ ID NO 59
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 59
gatctaatca gaaggacta                                              19

<210> SEQ ID NO 60
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 60
tcagaaggac tatcgctcc                                              19

<210> SEQ ID NO 61
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 61
ggactatcgc tccatgcca                                              19

<210> SEQ ID NO 62
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 62
aaagctatgc aagatgcag                                              19

<210> SEQ ID NO 63
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 63
agctatgcaa gatgcagaa                                              19

<210> SEQ ID NO 64
<211> LENGTH: 19
<212> TYPE: DNA
<213> ORGANISM: Homo sapiens
```

```
<220> FEATURE:
<221> NAME/KEY: misc_feature
<223> OTHER INFORMATION: Mortalin target sequence for siRNA silencing

<400> SEQUENCE: 64
gatgcagaag tcagcaaga                                                  19

<210> SEQ ID NO 65
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 65
gtcagcaaga gtgacatag                                                  19

<210> SEQ ID NO 66
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 66
gagtgacata ggagaagtg                                                  19

<210> SEQ ID NO 67
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 67
tgacatagga gaagtgatt                                                  19

<210> SEQ ID NO 68
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 68
gtgattcttg tgggtggca                                                  19

<210> SEQ ID NO 69
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 69
ggttcagcag actgtacag                                                  19

<210> SEQ ID NO 70
<211> LENGTH: 19
<212> TYPE: DNA
<213> ORGANISM: Homo sapiens
<220> FEATURE:
<221> NAME/KEY: misc_feature
```

```
<223> OTHER INFORMATION: Mortalin target sequence for siRNA silencing

<400> SEQUENCE: 70
gtaaagctgt caatcctga                                                19

<210> SEQ ID NO 71
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 71
agctgtcaat cctgatgag                                                19

<210> SEQ ID NO 72
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 72
tcctgatgag gctgtggcc                                                19

<210> SEQ ID NO 73
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 73
actctaggag gtgtcttta                                                19

<210> SEQ ID NO 74
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 74
taggaatacc actattcca                                                19

<210> SEQ ID NO 75
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 75
taccactatt ccaaccaag                                                19

<210> SEQ ID NO 76
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing
```

-continued

```
<400> SEQUENCE: 76
ccaagaagag ccaggtatt                                                19

<210> SEQ ID NO 77
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 77
gaagagccag gtattctct                                                19

<210> SEQ ID NO 78
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 78
gagccaggta ttctctact                                                19

<210> SEQ ID NO 79
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 79
acgcaagtgg aaattaaag                                                19

<210> SEQ ID NO 80
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 80
gtggaaatta agtgtgtc                                                 19

<210> SEQ ID NO 81
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 81
attaaagtgt gtcagggtg                                                19

<210> SEQ ID NO 82
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 82
```
agtgtgtcag ggtgaaaga                                                19

<210> SEQ ID NO 83
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 83
agagagatgg ctggagaca                                                19

<210> SEQ ID NO 84
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 84
caaactcctt ggacagttt                                                19

<210> SEQ ID NO 85
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 85
actccttgga cagtttact                                                19

<210> SEQ ID NO 86
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 86
tgggatagta catgttttct                                               19

<210> SEQ ID NO 87
<211> LENGTH: 21
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 87
gatagtacat gtttctgcta a                                             21

<210> SEQ ID NO 88
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 88
agataaaggc acaggacgt                                                19

<210> SEQ ID NO 89
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 89
aggcacagga cgtgagcag                                                        19

<210> SEQ ID NO 90
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 90
tccagtcttc tggtggatt                                                        19

<210> SEQ ID NO 91
<211> LENGTH: 21
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 91
gtggattaag caaagatgat a                                                     21

<210> SEQ ID NO 92
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 92
atgcagagaa atatgctga                                                        19

<210> SEQ ID NO 93
<211> LENGTH: 21
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 93
gcagagaaat atgctgaaga a                                                     21

<210> SEQ ID NO 94
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 94
atatgctgaa gaagaccgg                                                        19

<210> SEQ ID NO 95

```
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 95
gaagaccggc gaaagaagg                                                    19

<210> SEQ ID NO 96
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 96
gaccggcgaa agaaggaac                                                    19

<210> SEQ ID NO 97
<211> LENGTH: 21
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 97
cgaaagaagg aacgagttga a                                                 21

<210> SEQ ID NO 98
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 98
agaaggaacg agttgaagc                                                    19

<210> SEQ ID NO 99
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 99
ggaacgagtt gaagcagtt                                                    19

<210> SEQ ID NO 100
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 100
cgagttgaag cagttaata                                                    19

<210> SEQ ID NO 101
<211> LENGTH: 19
<212> TYPE: DNA
```

```
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 101
gcagttaata tggctgaag                                                    19

<210> SEQ ID NO 102
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 102
tatggctgaa ggaatcatt                                                    19

<210> SEQ ID NO 103
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 103
ggaatcattc acgacacag                                                    19

<210> SEQ ID NO 104
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 104
tcattcacga cacagaaac                                                    19

<210> SEQ ID NO 105
<211> LENGTH: 21
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 105
acagaaacca agatggaaga a                                                 21

<210> SEQ ID NO 106
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 106
accaagatgg aagaattca                                                    19

<210> SEQ ID NO 107
<211> LENGTH: 19
<212> TYPE: DNA
<213> ORGANISM: Homo sapiens
<220> FEATURE:
```

<221> NAME/KEY: misc_feature
<223> OTHER INFORMATION: Mortalin target sequence for siRNA silencing

<400> SEQUENCE: 107
gatggaagaa ttcaaggac                                       19

<210> SEQ ID NO 108
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 108
gaattcaagg accaattac                                       19

<210> SEQ ID NO 109
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 109
ttcaaggacc aattacctg                                       19

<210> SEQ ID NO 110
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 110
ggaccaatta cctgctgat                                       19

<210> SEQ ID NO 111
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 111
ttacctgctg atgagtgca                                       19

<210> SEQ ID NO 112
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 112
caagctgaaa gaagagatt                                       19

<210> SEQ ID NO 113
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 113
gctgaaagaa gagatttcc                                                19

<210> SEQ ID NO 114
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 114
gagatttcca aaatgaggg                                                19

<210> SEQ ID NO 115
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 115
aatgagggag ctcctggct                                                19

<210> SEQ ID NO 116
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 116
tgagggagct cctggctag                                                19

<210> SEQ ID NO 117
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 117
aagacagcga aacaggaga                                                19

<210> SEQ ID NO 118
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 118
gacagcgaaa caggagaaa                                                19

<210> SEQ ID NO 119
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 119
cagcgaaaca ggagaaaat                                              19

<210> SEQ ID NO 120
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 120
gctagaaaag acagcgaaa                                              19

<210> SEQ ID NO 121
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 121
aatattagac aggcagcat                                              19

<210> SEQ ID NO 122
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 122
tattagacag gcagcatcc                                              19

<210> SEQ ID NO 123
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 123
gctgttcgaa atggcatac                                              19

<210> SEQ ID NO 124
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 124
atggcataca aaagatgg                                               19

<210> SEQ ID NO 125
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 125
aaagatggca tctgagcga                                              19

<210> SEQ ID NO 126
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 126
agatggcatc tgagcgaga                                               19

<210> SEQ ID NO 127
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 127
gcgagaaggc tctggaagt                                               19

<210> SEQ ID NO 128
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 128
ggctctggaa gttctggca                                               19

<210> SEQ ID NO 129
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 129
gttctggcac tggggaaca                                               19

<210> SEQ ID NO 130
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 130
caaaaggaag atcaaaagg                                               19

<210> SEQ ID NO 131
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 131
aaggaagatc aaaaggagg                                               19

```
<210> SEQ ID NO 132
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 132
ggaagatcaa aaggaggaa                                              19

<210> SEQ ID NO 133
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 133
gatcaaaagg aggaaaaac                                              19

<210> SEQ ID NO 134
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 134
tagcagaaat tttgaagcc                                              19

<210> SEQ ID NO 135
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 135
attttgaagc cagaaggac                                              19

<210> SEQ ID NO 136
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 136
gccagaagga caacatatg                                              19

<210> SEQ ID NO 137
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 137
ggacaacata tgaagctta                                              19

<210> SEQ ID NO 138
<211> LENGTH: 19
```

```
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 138
catatgaagc ttaggagtg                                                  19

<210> SEQ ID NO 139
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 139
gcttaggagt gaagagact                                                  19

<210> SEQ ID NO 140
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 140
gagacttcct gagcagaaa                                                  19

<210> SEQ ID NO 141
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 141
atgggcgaac ttcagtctt                                                  19

<210> SEQ ID NO 142
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 142
cttcagtctt tttactgtg                                                  19

<210> SEQ ID NO 143
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 143
tggacagtga ttctaacag                                                  19

<210> SEQ ID NO 144
<211> LENGTH: 21
<212> TYPE: DNA
<213> ORGANISM: Homo sapiens
```

```
<220> FEATURE:
<221> NAME/KEY: misc_feature
<223> OTHER INFORMATION: Mortalin target sequence for siRNA silencing

<400> SEQUENCE: 144
gacagtgatt ctaacagtat a                                              21

<210> SEQ ID NO 145
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 145
tattctatgt ccctagcct                                                 19

<210> SEQ ID NO 146
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 146
aaggaggtag gatgaattg                                                 19

<210> SEQ ID NO 147
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 147
ggaggtagga tgaattgat                                                 19

<210> SEQ ID NO 148
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 148
gtgaccatat tttcaaggg                                                 19

<210> SEQ ID NO 149
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 149
ggggtgaaac catctcgca                                                 19

<210> SEQ ID NO 150
<211> LENGTH: 19
<212> TYPE: DNA
<213> ORGANISM: Homo sapiens
<220> FEATURE:
<221> NAME/KEY: misc_feature
```

-continued

<223> OTHER INFORMATION: Mortalin target sequence for siRNA silencing

<400> SEQUENCE: 150
accatctcgc acacagcaa                                                19

<210> SEQ ID NO 151
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 151
tgaaggtagt catccatag                                                19

<210> SEQ ID NO 152
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 152
ggtagtcatc catagactt                                                19

<210> SEQ ID NO 153
<211> LENGTH: 19
<212> TYPE: DNA
<213> ORGANISM: Homo sapiens

<400> SEQUENCE: 153
ccatagactt gaaatgaga                                                19

<210> SEQ ID NO 154
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 154
atgagaccac atatgggga                                                19

<210> SEQ ID NO 155
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 155
ctgaggcctt gcaagtcaa                                                19

<210> SEQ ID NO 156
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 156
gtcaagctgg ctgtgccat                                                19

```
<210> SEQ ID NO 157
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 157
gctggctgtg ccatgtttg                                               19

<210> SEQ ID NO 158
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 158
tctagaacaa tgggaaact                                               19

<210> SEQ ID NO 159
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 159
caatgggaaa cttagctat                                               19

<210> SEQ ID NO 160
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 160
aacaaggtag gaatgaggc                                               19

<210> SEQ ID NO 161
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 161
caaggtagga atgaggcta                                               19

<210> SEQ ID NO 162
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 162
ggtaggaatg aggctagac                                               19
```

<210> SEQ ID NO 163
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 163
tgaggctaga cctttaact                                               19

<210> SEQ ID NO 164
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 164
cttccctaag gcatacttt                                               19

<210> SEQ ID NO 165
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 165
ggcatacttt tctagctac                                               19

<210> SEQ ID NO 166
<211> LENGTH: 21
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 166
gaagaattca aggaccaatt a                                            21

<210> SEQ ID NO 167
<211> LENGTH: 21
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 167
acctgctgat gagtgcaaca a                                            21

<210> SEQ ID NO 168
<211> LENGTH: 21
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 168
gaagagactt cctgagcaga a                                            21

<210> SEQ ID NO 169
<211> LENGTH: 21

```
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 169
gacttgaaat gagaccacat a                                              21

<210> SEQ ID NO 170
<211> LENGTH: 21
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 170
atccttctag ttagcctagt a                                              21

<210> SEQ ID NO 171
<211> LENGTH: 19
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 171
gcagaggaat ctagaacaa                                                 19

<210> SEQ ID NO 172
<211> LENGTH: 21
<212> TYPE: DNA
<213> ORGANISM: Homo sapiens
<220> FEATURE:
<221> NAME/KEY: misc_feature
<223> OTHER INFORMATION: Mortalin target sequence for siRNA silencing

<400> SEQUENCE: 172
aggaatgagg ctagaccttt a                                              21

<210> SEQ ID NO 173
<211> LENGTH: 21
<212> TYPE: RNA
<213> ORGANISM: Artificial sequence
<220> FEATURE:
<223> OTHER INFORMATION: SiRNA oligonucleotide

<400> SEQUENCE: 173
ugccucguac uccuccauuu a                                              21

<210> SEQ ID NO 174
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 174
uggccuuagu caugaggcu                                                 19

<210> SEQ ID NO 175
<211> LENGTH: 19
<212> TYPE: RNA
<213> ORGANISM: Artificial sequence
<220> FEATURE:
<223> OTHER INFORMATION: SiRNA oligonucleotide
```

```
<400> SEQUENCE: 175
ggcgggauua ugcaucaga                                                19

<210> SEQ ID NO 176
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 176
gcaaucaagg gagcaguug                                                19

<210> SEQ ID NO 177
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 177
ucaagggagc aguuguugg                                                19

<210> SEQ ID NO 178
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 178
gggagcaguu guugguauu                                                19

<210> SEQ ID NO 179
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 179
cuccugcgug gcaguuaug                                                19

<210> SEQ ID NO 180
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 180
uggcaguuau ggaagguaa                                                19

<210> SEQ ID NO 181
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 181
gguaaacaag caaaggugc                                                19

<210> SEQ ID NO 182
<211> LENGTH: 19
```

```
<212> TYPE: RNA
<213> ORGANISM: Artificial sequence
<220> FEATURE:
<223> OTHER INFORMATION: SiRNA oligonucleotide

<400> SEQUENCE: 182
acaagcaaag gugcuggag                                                  19

<210> SEQ ID NO 183
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 183
gcaaaggugc uggagaaug                                                  19

<210> SEQ ID NO 184
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 184
aggugcugga gaaugccga                                                  19

<210> SEQ ID NO 185
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 185
ugccgaaggu gccagaacc                                                  19

<210> SEQ ID NO 186
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 186
ggugccagaa ccaccccuu                                                  19

<210> SEQ ID NO 187
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 187
ccaccccuuc aguuguggc                                                  19

<210> SEQ ID NO 188
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 188
gcgacaggcu gucaccaac                                                  19
```

```
<210> SEQ ID NO 189
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 189
aauuguccgu gccuccaau                                                        19

<210> SEQ ID NO 190
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 190
uuguccgugc cuccaaugg                                                        19

<210> SEQ ID NO 191
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 191
uggugaugcc uggguugag                                                        19

<210> SEQ ID NO 192
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 192
auuguauucu ccgagucag                                                        19

<210> SEQ ID NO 193
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 193
gagucagauu ggagcauuu                                                        19

<210> SEQ ID NO 194
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 194
gagcauuugu guugaugaa                                                        19

<210> SEQ ID NO 195
<211> LENGTH: 19
<212> TYPE: RNA
<213> ORGANISM: Artificial sequence
<220> FEATURE:
<223> OTHER INFORMATION: SiRNA oligonucleotide
```

```
<400> SEQUENCE: 195
gaugaaagag acugcagaa                                              19

<210> SEQ ID NO 196
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 196
agagacugca gaaaauuac                                              19

<210> SEQ ID NO 197
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 197
aauuacuugg ggcacacag                                              19

<210> SEQ ID NO 198
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 198
uuacuugggg cacacagca                                              19

<210> SEQ ID NO 199
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 199
aaaaugcugu gaucacagu                                              19

<210> SEQ ID NO 200
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 200
aaugcuguga ucacagucc                                              19

<210> SEQ ID NO 201
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 201
ugcugugauc acaguccca                                              19

<210> SEQ ID NO 202
<211> LENGTH: 19
```

```
<212> TYPE: RNA
<213> ORGANISM: Artificial sequence
<220> FEATURE:
<223> OTHER INFORMATION: SiRNA oligonucleotide

<400> SEQUENCE: 202
ugacucgcag agacaggcc                                              19

<210> SEQ ID NO 203
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 203
agaugcuggc cagauaucu                                              19

<210> SEQ ID NO 204
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 204
ugugcuucgg gugauuaau                                              19

<210> SEQ ID NO 205
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 205
ugagcccaca gcugcugcu                                              19

<210> SEQ ID NO 206
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 206
ugccuauggu cuagacaaa                                              19

<210> SEQ ID NO 207
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 207
agacaaauca gaagacaaa                                              19

<210> SEQ ID NO 208
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 208
gacaaaguca uugcuguau                                              19
```

<210> SEQ ID NO 209
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 209
ugauuuaggu gguggaacu                                                19

<210> SEQ ID NO 210
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 210
ggaaauucag aaaggagua                                                19

<210> SEQ ID NO 211
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 211
aggaguauuu gaggugaaa                                                19

<210> SEQ ID NO 212
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 212
auccacaaau ggggauacc                                                19

<210> SEQ ID NO 213
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 213 augggauac cuucuuagg                                                 19

<210> SEQ ID NO 214
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 214
gacuuugacc aggccuugc                                                19

<210> SEQ ID NO 215
<211> LENGTH: 19
<212> TYPE: RNA
<213> ORGANISM: Artificial sequence
<220> FEATURE:
<223> OTHER INFORMATION: SiRNA oligonucleotide -continued

<400> SEQUENCE: 215
ggaguucaag agagagaca                                                    19

<210> SEQ ID NO 216
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 216
gagagagaca ggggguugau                                                   19

<210> SEQ ID NO 217
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 217
agacaacaug gcacuucag                                                    19

<210> SEQ ID NO 218
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 218
cauggcacuu cagagggua                                                    19

<210> SEQ ID NO 219
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 219
gcugcugaaa aggcuaaau                                                    19

<210> SEQ ID NO 220
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 220
aaggcuaaau gugaacucu                                                    19

<210> SEQ ID NO 221
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 221
ggcuaaaugu gaacucucc                                                    19

<210> SEQ ID NO 222
<211> LENGTH: 19

```
<212> TYPE: RNA
<213> ORGANISM: Artificial sequence
<220> FEATURE:
<223> OTHER INFORMATION: SiRNA oligonucleotide

<400> SEQUENCE: 222
augugaacuc uccucaucu                                                    19

<210> SEQ ID NO 223
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 223
cucuccucau cugugcaga                                                    19

<210> SEQ ID NO 224
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 224
uuugcccuau cuuacaaug                                                    19

<210> SEQ ID NO 225
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 225
uggauucuuc uggacccaa                                                    19

<210> SEQ ID NO 226
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 226
ggacccaagc auuugaaua                                                    19

<210> SEQ ID NO 227
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 227
uaugaaguug acccgugcu                                                    19

<210> SEQ ID NO 228
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 228
guugacccgu gcucaauuu                                                    19
```

<210> SEQ ID NO 229
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 229
uuugaaggga uugucacug                                                    19

<210> SEQ ID NO 230
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 230
gggauuguca cugaucuaa                                                    19

<210> SEQ ID NO 231
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 231
gaucuaauca gaaggacua                                                    19

<210> SEQ ID NO 232
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 232
ucagaaggac uaucgcucc                                                    19

<210> SEQ ID NO 233
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 233
ggacuaucgc uccaugcca                                                    19

<210> SEQ ID NO 234
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 234
aaagcuaugc aagaugcag                                                    19

<210> SEQ ID NO 235
<211> LENGTH: 19
<212> TYPE: RNA
<213> ORGANISM: Artificial sequence
<220> FEATURE:
<223> OTHER INFORMATION: SiRNA oligonucleotide

```
<400> SEQUENCE: 235
agcuaugcaa gaugcagaa                                              19

<210> SEQ ID NO 236
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 236
gaugcagaag ucagcaaga                                              19

<210> SEQ ID NO 237
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 237
gucagcaaga gugacauag                                              19

<210> SEQ ID NO 238
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 238
gagugacaua ggagaagug                                              19

<210> SEQ ID NO 239
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 239
ugacauagga gaagugauu                                              19

<210> SEQ ID NO 240
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 240
gugauucuug uggguggca                                              19

<210> SEQ ID NO 241
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 241
gguucagcag acuguacag                                              19

<210> SEQ ID NO 242
<211> LENGTH: 19
```

```
<212> TYPE: RNA
<213> ORGANISM: Artificial sequence
<220> FEATURE:
<223> OTHER INFORMATION: SiRNA oligonucleotide

<400> SEQUENCE: 242
guaaagcugu caauccuga                                                    19

<210> SEQ ID NO 243
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 243
agcugucaau ccugaugag                                                    19

<210> SEQ ID NO 244
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 244
uccugaugag gcuguggcc                                                    19

<210> SEQ ID NO 245
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 245
acucuaggag gugucuuua                                                    19

<210> SEQ ID NO 246
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 246
uaggaauacc acuauucca                                                    19

<210> SEQ ID NO 247
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 247
uaccacuauu ccaaccaag                                                    19

<210> SEQ ID NO 248
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 248
ccaagaagag ccagguauu                                                    19
```

<210> SEQ ID NO 249
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 249
gaagagccag guauucucu                                                19

<210> SEQ ID NO 250
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 250
gagccaggua uucucuacu                                                19

<210> SEQ ID NO 251
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 251
acgcaagugg aaauuaaag                                                19

<210> SEQ ID NO 252
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 252
guggaaauua aaguguguc                                                19

<210> SEQ ID NO 253
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 253
auuaaagugu gucagggug                                                19

<210> SEQ ID NO 254
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 254
agugugucag ggugaaaga                                                19

<210> SEQ ID NO 255
<211> LENGTH: 19
<212> TYPE: RNA
<213> ORGANISM: Artificial sequence
<220> FEATURE:
<223> OTHER INFORMATION: SiRNA oligonucleotide

```
<400> SEQUENCE: 255
agagagaugg cuggagaca                                           19

<210> SEQ ID NO 256
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 256
caaacuccuu ggacaguuu                                           19

<210> SEQ ID NO 257
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 257
acuccuugga caguuuacu                                           19

<210> SEQ ID NO 258
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 258
ugggauagua cauguuucu                                           19

<210> SEQ ID NO 259
<211> LENGTH: 21
<212> TYPE: RNA
<213> ORGANISM: Artificial sequence
<220> FEATURE:
<223> OTHER INFORMATION: SiRNA oligonucleotide

<400> SEQUENCE: 259
gauaguacau guuucugcua a                                        21

<210> SEQ ID NO 260
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 260
agauaaaggc acaggacgu                                           19

<210> SEQ ID NO 261
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 261
aggcacagga cgugagcag                                           19

<210> SEQ ID NO 262
<211> LENGTH: 19
```

```
<212> TYPE: RNA
<213> ORGANISM: Artificial sequence
<220> FEATURE:
<223> OTHER INFORMATION: SiRNA oligonucleotide

<400> SEQUENCE: 262
uccagucuuc ugguggauu                                                  19

<210> SEQ ID NO 263
<211> LENGTH: 21
<212> TYPE: RNA
<213> ORGANISM: Artificial sequence
<220> FEATURE:
<223> OTHER INFORMATION: SiRNA oligonucleotide

<400> SEQUENCE: 263
guggauuaag caaagaugau a                                               21

<210> SEQ ID NO 264
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 264
augcagagaa auaugcuga                                                  19

<210> SEQ ID NO 265
<211> LENGTH: 21
<212> TYPE: RNA
<213> ORGANISM: Artificial sequence
<220> FEATURE:
<223> OTHER INFORMATION: SiRNA oligonucleotide

<400> SEQUENCE: 265
gcagagaaau augcugaaga a                                               21

<210> SEQ ID NO 266
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 266
auaugcugaa gaagaccgg                                                  19

<210> SEQ ID NO 267
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 267
gaagaccggc gaaagaagg                                                  19

<210> SEQ ID NO 268
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 268
gaccggcgaa agaaggaac                                                  19
```

```
<210> SEQ ID NO 269
<211> LENGTH: 21
<212> TYPE: RNA
<213> ORGANISM: Artificial sequence
<220> FEATURE:
<223> OTHER INFORMATION: SiRNA oligonucleotide

<400> SEQUENCE: 269
cgaaagaagg aacgaguuga a                                              21

<210> SEQ ID NO 270
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 270
agaaggaacg aguugaagc                                                 19

<210> SEQ ID NO 271
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 271
ggaacgaguu gaagcaguu                                                 19

<210> SEQ ID NO 272
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 272
cgaguugaag caguuaaua                                                 19

<210> SEQ ID NO 273
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 273
gcaguuaaua uggcugaag                                                 19

<210> SEQ ID NO 274
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 274
uauggcugaa ggaaucauu                                                 19

<210> SEQ ID NO 275
<211> LENGTH: 19
<212> TYPE: RNA
<213> ORGANISM: Artificial sequence
<220> FEATURE:
<223> OTHER INFORMATION: SiRNA oligonucleotide
```

```
<400> SEQUENCE: 275
ggaaucauuc acgacacag                                              19

<210> SEQ ID NO 276
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 276
ucauucacga cacagaaac                                              19

<210> SEQ ID NO 277
<211> LENGTH: 21
<212> TYPE: RNA
<213> ORGANISM: Artificial sequence
<220> FEATURE:
<223> OTHER INFORMATION: SiRNA oligonucleotide

<400> SEQUENCE: 277
acagaaacca agauggaaga a                                           21

<210> SEQ ID NO 278
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 278
accaagaugg aagaauuca                                              19

<210> SEQ ID NO 279
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 279
gauggaagaa uucaaggac                                              19

<210> SEQ ID NO 280
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 280
gaauucaagg accaauuac                                              19

<210> SEQ ID NO 281
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 281
uucaaggacc aauuaccug                                              19

<210> SEQ ID NO 282
<211> LENGTH: 19
```

```
<212> TYPE: RNA
<213> ORGANISM: Artificial sequence
<220> FEATURE:
<223> OTHER INFORMATION: SiRNA oligonucleotide

<400> SEQUENCE: 282
ggaccaauua ccugcugau                                                    19

<210> SEQ ID NO 283
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 283
uuaccugcug augagugca                                                    19

<210> SEQ ID NO 284
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 284
caagcugaaa gaagagauu                                                    19

<210> SEQ ID NO 285
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 285
gcugaaagaa gagauuucc                                                    19

<210> SEQ ID NO 286
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 286
gagauuucca aaaugaggg                                                    19

<210> SEQ ID NO 287
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 287
aaugagggag cuccuggcu                                                    19

<210> SEQ ID NO 288
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 288
ugagggagcu ccuggcuag                                                    19
```

<210> SEQ ID NO 289
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 289
aagacagcga aacaggaga                                              19

<210> SEQ ID NO 290
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 290
gacagcgaaa caggagaaa                                              19

<210> SEQ ID NO 291
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 291
cagcgaaaca ggagaaaau                                              19

<210> SEQ ID NO 292
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 292
gcuagaaaag acagcgaaa                                              19

<210> SEQ ID NO 293
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 293
aauauuagac aggcagcau                                              19

<210> SEQ ID NO 294
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 294
uauuagacag gcagcaucc                                              19

<210> SEQ ID NO 295
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 295
gcuguucgaa auggcauac                                                    19

<210> SEQ ID NO 296
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 296
auggcauaca aaagaugg                                                     19

<210> SEQ ID NO 297
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 297
aaagauggca ucugagcga                                                    19

<210> SEQ ID NO 298
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 298
agauggcauc ugagcgaga                                                    19

<210> SEQ ID NO 299
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 299
gcgagaaggc ucuggaagu                                                    19

<210> SEQ ID NO 300
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 300
ggcucuggaa guucuggca                                                    19

<210> SEQ ID NO 301
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 301
guucuggcac ugggaaca                                                     19

<210> SEQ ID NO 302
<211> LENGTH: 19

```
<212> TYPE: RNA
<213> ORGANISM: Artificial sequence
<220> FEATURE:
<223> OTHER INFORMATION: SiRNA oligonucleotide

<400> SEQUENCE: 302
caaaaggaag aucaaaagg                                                19

<210> SEQ ID NO 303
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 303
aaggaagauc aaaaggagg                                                19

<210> SEQ ID NO 304
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 304
ggaagaucaa aaggaggaa                                                19

<210> SEQ ID NO 305
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 305
gaucaaaagg aggaaaaac                                                19

<210> SEQ ID NO 306
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 306
uagcagaaau uuugaagcc                                                19

<210> SEQ ID NO 307
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 307
auuuugaagc cagaaggac                                                19

<210> SEQ ID NO 308
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 308
gccagaagga caacauaug                                                19
```

```
<210> SEQ ID NO 309
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 309
ggacaacaua ugaagcuua                                              19

<210> SEQ ID NO 310
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 310
cauaugaagc uuaggagug                                              19

<210> SEQ ID NO 311
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 311
gcuuaggagu gaagagacu                                              19

<210> SEQ ID NO 312
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 312
gagacuuccu gagcagaaa                                              19

<210> SEQ ID NO 313
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 313
augggcgaac uucagucuu                                              19

<210> SEQ ID NO 314
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 314
cuucagucuu uuuacugug                                              19

<210> SEQ ID NO 315
<211> LENGTH: 19
<212> TYPE: RNA
<213> ORGANISM: Artificial sequence
<220> FEATURE:
<223> OTHER INFORMATION: SiRNA oligonucleotide
```

```
<400> SEQUENCE: 315
uggacaguga uucuaacag                                              19

<210> SEQ ID NO 316
<211> LENGTH: 21
<212> TYPE: RNA
<213> ORGANISM: Artificial sequence
<220> FEATURE:
<223> OTHER INFORMATION: SiRNA oligonucleotide

<400> SEQUENCE: 316
gacagugauu cuaacaguau a                                           21

<210> SEQ ID NO 317
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 317
uauucuaugu cccuagccu                                              19

<210> SEQ ID NO 318
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 318
aaggagguag gaugaauug                                              19

<210> SEQ ID NO 319
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 319
ggagguagga ugaauugau                                              19

<210> SEQ ID NO 320
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 320
gugaccauau uuucaaggg                                              19

<210> SEQ ID NO 321
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 321
ggggugaaac caucucgca                                              19

<210> SEQ ID NO 322
<211> LENGTH: 19
```

```
<212> TYPE: RNA
<213> ORGANISM: Artificial sequence
<220> FEATURE:
<223> OTHER INFORMATION: SiRNA oligonucleotide

<400> SEQUENCE: 322
accaucucgc acacagcaa                                              19

<210> SEQ ID NO 323
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 323
ugaagguagu cauccauag                                              19

<210> SEQ ID NO 324
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 324
gguagucauc cauagacuu                                              19

<210> SEQ ID NO 325
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 325
ccauagacuu gaaaugaga                                              19

<210> SEQ ID NO 326
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 326
augagaccac auauggga                                               19

<210> SEQ ID NO 327
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 327
cugaggccuu gcaagucaa                                              19

<210> SEQ ID NO 328
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 328
gucaagcugg cugugccau                                              19
```

<210> SEQ ID NO 329
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 329
gcuggcugug ccauguuug                                              19

<210> SEQ ID NO 330
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 330
ucuagaacaa ugggaaacu                                              19

<210> SEQ ID NO 331
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 331
caaugggaaa cuuagcuau                                              19

<210> SEQ ID NO 332
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 332
aacaagguag gaaugaggc                                              19

<210> SEQ ID NO 333
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 333
caagguagga augaggcua                                              19

<210> SEQ ID NO 334
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 334
gguaggaaug aggcuagac                                              19

<210> SEQ ID NO 335
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 335
ugaggcuaga ccuuuaacu                                                19

<210> SEQ ID NO 336
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 336
cuucccuaag gcauacuuu                                                19

<210> SEQ ID NO 337
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 337
ggcauacuuu ucuagcuac                                                19

<210> SEQ ID NO 338
<211> LENGTH: 21
<212> TYPE: RNA
<213> ORGANISM: Artificial sequence
<220> FEATURE:
<223> OTHER INFORMATION: SiRNA oligonucleotide

<400> SEQUENCE: 338
gaagaauuca aggaccaauu a                                             21

<210> SEQ ID NO 339
<211> LENGTH: 21
<212> TYPE: RNA
<213> ORGANISM: Artificial sequence
<220> FEATURE:
<223> OTHER INFORMATION: SiRNA oligonucleotide

<400> SEQUENCE: 339
accugcugau gagugcaaca a                                             21

<210> SEQ ID NO 340
<211> LENGTH: 21
<212> TYPE: RNA
<213> ORGANISM: Artificial sequence
<220> FEATURE:
<223> OTHER INFORMATION: SiRNA oligonucleotide

<400> SEQUENCE: 340
gaagagacuu ccugagcaga a                                             21

<210> SEQ ID NO 341
<211> LENGTH: 21
<212> TYPE: RNA
<213> ORGANISM: Artificial sequence
<220> FEATURE:
<223> OTHER INFORMATION: SiRNA oligonucleotide

<400> SEQUENCE: 341
gacuugaaau gagaccacau a                                             21

<210> SEQ ID NO 342
<211> LENGTH: 21

```
<212> TYPE: RNA
<213> ORGANISM: Artificial sequence
<220> FEATURE:
<223> OTHER INFORMATION: SiRNA oligonucleotide

<400> SEQUENCE: 342
auccuucuag uuagccuagu a                                              21

<210> SEQ ID NO 343
<211> LENGTH: 19
<212> TYPE: RNA
<213> ORGANISM: Artificial sequence
<220> FEATURE:
<223> OTHER INFORMATION: SiRNA oligonucleotide

<400> SEQUENCE: 343
gcagaggaau cuagaacaa                                                 19

<210> SEQ ID NO 344
<211> LENGTH: 21
<212> TYPE: RNA
<213> ORGANISM: Artificial sequence
<220> FEATURE:
<223> OTHER INFORMATION: SiRNA oligonucleotide

<400> SEQUENCE: 344
aggaaugagg cuagaccuuu a                                              21

<210> SEQ ID NO 345
<211> LENGTH: 19
<212> TYPE: RNA
<213> ORGANISM: Artificial sequence
<220> FEATURE:
<223> OTHER INFORMATION: Control, non-specific SiRNA oligonucleotide

<400> SEQUENCE: 345
acucuaucug cacgcugac                                                 19

<210> SEQ ID NO 346
<211> LENGTH: 2850
<212> TYPE: DNA
<213> ORGANISM: Homo sapiens

<400> SEQUENCE: 346
tcaccccacg tggttggagg tttccagaag cgctgccgcc accgcatcgc gcagctcttt    60
gccgtcggag cgcttgtttg ctgcctcgta ctcctccatt tatccgccat gataagtgcc   120
agccgagctg cagcagcccg tctcgtgggc gccgcagcct cccggggccc tacggccgcc   180
cgccaccagg atagctggaa tggccttagt catgaggctt ttagacttgt ttcaaggcgg   240
gattatgcat cagaagcaat caagggagca gttgttggta ttgatttggg tactaccaac   300
tcctgcgtgg cagttatgga aggtaaacaa gcaaaggtgc tggagaatgc cgaaggtgcc   360
agaaccaccc cttcagttgt ggcctttaca gcagatggtg agcgacttgt tggaatgccg   420
gccaagcgac aggctgtcac caacccaaac aatacatttt atgctaccaa gcgtctcatt   480
ggccggcgat atgatgatcc tgaagtacag aaagacatta aaaatgttcc ctttaaaatt   540
gtccgtgcct ccaatggtga tgcctgggtt gaggctcatg ggaaattgta ttctccgagt   600
cagattggag catttgtgtt gatgaagatg aaagagactg cagaaaatta cttggggcac   660
acagcaaaaa atgctgtgat cacagtccca gcttatttca atgactcgca gagacaggcc   720
actaaagatg ctggccagat atctggactg aatgtgcttc gggtgattaa tgagcccaca   780
gctgctgctc ttgcctatgg tctagacaaa tcagaagaca agtcattgc tgtatatgat    840
```

```
ttaggtggtg gaacttttga tatttctatc ctggaaattc agaaaggagt atttgaggtg      900
aaatccacaa atggggatac cttcttaggt ggggaagact ttgaccaggc cttgctacgg      960
cacattgtga aggagttcaa gagagagaca ggggttgatt tgactaaaga caacatggca     1020
cttcagaggg tacgggaagc tgctgaaaag ctaaatgtg aactctcctc atctgtgcag      1080
actgacatca atttgcccta tcttacaatg gattcttctg acccaagca tttgaatatg      1140 aagttgaccc gtgctcaatt tgaagggatt gtcactgatc taatcagaag gactatcgct     1200
ccatgccaaa aagctatgca agatgcagaa gtcagcaaga gtgacatagg agaagtgatt     1260
cttgtgggtg gcatgactag gatgcccaag gttcagcaga ctgtacagga tcttttttggc    1320 agagccccaa gtaaagctgt caatcctgat gaggctgtgg ccattggagc tgccattcag     1380
ggaggtgtgt tggccggcga tgtcacggat gtgctgctcc ttgatgtcac tcccctgtct    1440
ctgggtattg aaactctagg aggtgtctt accaaactta ttaataggaa taccactatt      1500
ccaaccaaga gagccaggt attctctact gccgctgatg tcaaacgca agtggaaatt       1560 aaagtgtgtc agggtgaaag agagatggct ggagacaaca aactccttgg acagtttact     1620
ttgattggaa ttccaccagc ccctcgtgga gttcctcaga ttgaagttac atttgacatt    1680
gatgccaatg ggatagtaca tgttttctgct aaagataaag gcacaggacg tgagcagcag   1740
attgtaatcc agtcttctgg tggattaagc aaagatgata ttgaaaatat ggttaaaaat    1800
gcagagaaat atgctgaaga agaccggcga agaaggaac gagttgaagc agttaatatg     1860
gctgaaggaa tcattcacga cacagaaacc aagatggaag aattcaagga ccaattacct    1920
gctgatgagt gcaacaagct gaaagaagag atttccaaaa tgagggagct cctggctaga    1980
aaagacagcg aaacaggaga aaatattaga caggcagcat cctctcttca gcaggcatca     2040
ctgaagctgt tcgaaatggc atacaaaaag atggcatctg agcgagaagg ctctggaagt    2100
tctggcactg gggaacaaaa ggaagatcaa aaggaggaaa aacagtaata atagcagaaa    2160
ttttgaagcc agaaggacaa catatgaagc ttaggagtga agagacttcc tgagcagaaa    2220
tgggcgaact tcagtcttt tactgtgttt ttgcagtatt ctatatataa tttccttaat     2280
ttgtaaattt agtgaccatt agctagtgat catttaatgg acagtgattc taacagtata    2340
aagttcacaa tattctatgt ccctagcctg tcattttca gctgcatgta aaaggaggta     2400
ggatgaattg atcattataa agatttaact attttatgct gaagtgacca tatttttcaag  2460 gggtgaaacc atctcgcaca cagcaatgaa ggtagtcatc catagacttg aaatgagacc    2520
acatatgggg atgagatcct tctagttagc ctagtactgc tgtactggcc tgtatgtaca    2580
tggggtcctt caactgaggc cttgcaagtc aagctggctg tgccatgttt gtagatgggg    2640
cagaggaatc tagaacaatg ggaaacttag ctatttatat taggtacagc tattaaaaca    2700
aggtaggaat gaggctagac ctttaacttc cctaaggcat acttttctag ctaccttctg    2760
ccctgtgtct ggcacctaca tccttgatga ttgttctctt acccattctg gaattttttt    2820 tttttttaaat aaatacagaa agcatcttga                                     2850
```

<210> SEQ ID NO 347
<211> LENGTH: 672
<212> TYPE: PRT
<213> ORGANISM: Homo sapiens

<400> SEQUENCE: 347

Met Ile Ser Ala Ser Arg Ala Ala Ala Ala Arg Leu Val Gly Ala Ala
1               5                   10                  15

-continued

```
Ala Ser Arg Gly Pro Thr Ala Ala Arg His Gln Asp Ser Trp Asn Gly
             20                  25                  30

Leu Ser His Glu Ala Phe Arg Leu Val Ser Arg Arg Asp Tyr Ala Ser
         35                  40                  45

Glu Ala Ile Lys Gly Ala Val Val Gly Ile Asp Leu Gly Thr Thr Asn
 50                  55                  60

Ser Cys Val Ala Val Met Glu Gly Lys Gln Ala Lys Val Leu Glu Asn
 65                  70                  75                  80

Ala Glu Gly Ala Arg Thr Thr Pro Ser Val Val Ala Phe Thr Ala Asp
                 85                  90                  95

Gly Glu Arg Leu Val Gly Met Pro Ala Lys Arg Gln Ala Val Thr Asn
            100                 105                 110

Pro Asn Asn Thr Phe Tyr Ala Thr Lys Arg Leu Ile Gly Arg Arg Tyr
        115                 120                 125

Asp Asp Pro Glu Val Gln Lys Asp Ile Lys Asn Val Pro Phe Lys Ile
    130                 135                 140

Val Arg Ala Ser Asn Gly Asp Ala Trp Val Glu Ala His Gly Lys Leu
145                 150                 155                 160

Tyr Ser Pro Ser Gln Ile Gly Ala Phe Val Leu Met Lys Met Lys Glu
                165                 170                 175

Thr Ala Glu Asn Tyr Leu Gly His Thr Ala Lys Asn Ala Val Ile Thr
            180                 185                 190

Val Pro Ala Tyr Phe Asn Asp Ser Gln Arg Gln Ala Thr Lys Asp Ala
        195                 200                 205

Gly Gln Ile Ser Gly Leu Asn Val Leu Arg Val Ile Asn Glu Pro Thr
    210                 215                 220

Ala Ala Ala Leu Ala Tyr Gly Leu Asp Lys Ser Glu Asp Lys Val Ile
225                 230                 235                 240

Ala Val Tyr Asp Leu Gly Gly Gly Thr Phe Asp Ile Ser Ile Leu Glu
                245                 250                 255

Ile Gln Lys Gly Val Phe Glu Val Lys Ser Thr Asn Gly Asp Thr Phe
            260                 265                 270

Leu Gly Gly Glu Asp Phe Asp Gln Ala Leu Leu Arg His Ile Val Lys
        275                 280                 285

Glu Phe Lys Arg Glu Thr Gly Val Asp Leu Thr Lys Asp Asn Met Ala
    290                 295                 300

Leu Gln Arg Val Arg Glu Ala Ala Glu Lys Ala Lys Cys Glu Leu Ser
305                 310                 315                 320

Ser Ser Val Gln Thr Asp Ile Asn Leu Pro Tyr Leu Thr Met Asp Ser
                325                 330                 335

Ser Gly Pro Lys His Leu Asn Met Lys Leu Thr Arg Ala Gln Phe Glu
            340                 345                 350

Gly Ile Val Thr Asp Leu Ile Arg Arg Thr Ile Ala Pro Cys Gln Lys
        355                 360                 365

Ala Met Gln Asp Ala Glu Val Ser Lys Ser Asp Ile Gly Glu Val Ile
    370                 375                 380

Leu Val Gly Gly Met Thr Arg Met Pro Lys Val Gln Gln Thr Val Gln
385                 390                 395                 400

Asp Leu Phe Gly Arg Ala Pro Ser Lys Ala Val Asn Pro Asp Glu Ala
                405                 410                 415

Val Ala Ile Gly Ala Ala Ile Gln Gly Gly Val Leu Ala Gly Asp Val
            420                 425                 430

Thr Asp Val Leu Leu Leu Asp Val Thr Pro Leu Ser Leu Gly Ile Glu
        435                 440                 445
```

```
Thr Leu Gly Gly Val Phe Thr Lys Leu Ile Asn Arg Asn Thr Thr Ile
        450                 455                 460

Pro Thr Lys Lys Ser Gln Val Phe Ser Thr Ala Ala Asp Gly Gln Thr
465                 470                 475                 480

Gln Val Glu Ile Lys Val Cys Gln Gly Glu Arg Glu Met Ala Gly Asp
                485                 490                 495

Asn Lys Leu Leu Gly Gln Phe Thr Leu Ile Gly Ile Pro Pro Ala Pro
            500                 505                 510

Arg Gly Val Pro Gln Ile Glu Val Thr Phe Asp Ile Asp Ala Asn Gly
        515                 520                 525

Ile Val His Val Ser Ala Lys Asp Lys Gly Thr Gly Arg Glu Gln Gln
    530                 535                 540

Ile Val Ile Gln Ser Ser Gly Gly Leu Ser Lys Asp Asp Ile Glu Asn
545                 550                 555                 560

Met Val Lys Asn Ala Glu Lys Tyr Ala Glu Glu Asp Arg Arg Lys Lys
                565                 570                 575

Glu Arg Val Glu Ala Val Asn Met Ala Glu Gly Ile Ile His Asp Thr
            580                 585                 590

Glu Thr Lys Met Glu Glu Phe Lys Asp Gln Leu Pro Ala Asp Glu Cys
        595                 600                 605

Asn Lys Leu Lys Glu Glu Ile Ser Lys Met Arg Glu Leu Leu Ala Arg
    610                 615                 620

Lys Asp Ser Glu Thr Gly Glu Asn Ile Arg Gln Ala Ala Ser Ser Leu
625                 630                 635                 640

Gln Gln Ala Ser Leu Lys Leu Phe Glu Met Ala Tyr Lys Lys Met Ala
                645                 650                 655

Ser Glu Arg Glu Gly Ser Gly Ser Ser Gly Thr Gly Glu Gln Lys Glu
            660                 665                 670

<210> SEQ ID NO 348
<211> LENGTH: 21
<212> TYPE: RNA
<213> ORGANISM: Artificial sequence
<220> FEATURE:
<223> OTHER INFORMATION: SiRNA oligonucleotide

<400> SEQUENCE: 348
aaggauuaug acugcuaucu u                                           21

<210> SEQ ID NO 349
<211> LENGTH: 21
<212> TYPE: RNA
<213> ORGANISM: Artificial sequence
<220> FEATURE:
<223> OTHER INFORMATION: SiRNA oligonucleotide

<400> SEQUENCE: 349
uccuacaacu aaugccuuua a                                           21

<210> SEQ ID NO 350
<211> LENGTH: 21
<212> TYPE: RNA
<213> ORGANISM: Artificial sequence
<220> FEATURE:
<223> OTHER INFORMATION: SiRNA oligonucleotide

<400> SEQUENCE: 350
acucuaucug cacgcugacu u                                           21
```

DOWN-REGULATION OF MORTALIN BY SIRNA

RELATED APPLICATIONS

This Application is a National Phase of PCT Patent Application No. PCT/IL2008/001295 having International filing date of Sep. 25, 2008, which claims the benefit of U.S. Provisional Patent Application No. 60/960,311 filed on Sep. 25, 2007. The contents of the above Applications are all incorporated herein by reference.

FIELD AND BACKGROUND OF THE INVENTION

The present invention relates to siRNA specific to mortalin and to the use of same for decreasing the levels of mortalin for disease treatment.

Diseases such as tumoral, infectious, autoimmune and transplantation-related diseases, which are associated with pathological cells and are treatable via complement-mediated cytolysis of such cells, represent numerous highly debilitating and/or lethal diseases for which no optimal therapy exists. There is therefore a long-felt and urgent need in the art for novel and maximally effective methods and therapeutic agents for treating such diseases.

The complement system consists of more than twenty blood plasma proteins that cooperate with other sections of the innate and acquired immune systems in clearance of pathogenic organisms, immune complexes and apoptotic cells. The complement activation cascade culminates in formation of the membrane attack complex (MAC), made of complement C5b, C6, C7, C8 and C9 proteins (termed "C5b-9"), and its insertion into the plasma membrane of target cells. Membrane insertion begins when C5b-7 forms, is enhanced upon formation of C5b-8 complex and is maximal upon binding and oligomerization of C9 and formation of a transmembrane, cylinder-shape polyC9 complex attached to C5b-8. At supralytic doses, MAC normally functions to induce rapid cell death by necrosis (Koski, C. L. et aL, 1983. Proc Natl Acad Sci USA 80:3816) or apoptosis (Cragg, M. S. et al., 2000. Cell Death Differ 7:48). At low, sublytic doses, MAC acts as a potent stimulator of numerous cellular activities (for review see Bohana-Kashtan, O. et al., 2004. Mol Immunol 41:583). Treatment with sublytic MAC has been shown to transduce either anti-necrotic (Reiter, Y. et al., 1992. Eur J Immunol 22:1207) or anti-apoptotic (Dashiell, S. M. et al., 2000. Glia 30:187) signals into various cells.

As a means of protection from complement, nucleated cells can remove the MAC from their plasma membrane by endocytosis, vesiculation or proteolytic fragmentation. Physical removal of MAC by vesiculation has been demonstrated in several cell types including neutrophils, oligodendrocytes and platelets, and in the tumor cell lines U937 and K562 (Sims, P. J. and Wiedmer, T. 1986. Blood 68:556; Scolding, N. J. et al., 1989. Nature 339:620; Morgan, B. P. et al., 1986. J Immunol 136:3402; Morgan, B. P. 1992. Curr Top Microbiol Immunol 178:115). To date, little is known about the molecular mechanism responsible for MAC vesiculation. Yet, removal of complement from nucleated cells may be associated with disease pathogenesis. For example, MAC removal has been shown to protect cancer cells from complement-mediated cytotoxicity (Carney D. F., J Immunol 134: 1804, 1985; Pilzer D. and Fishelson Z., Int Immunol 17:1239, 2005). Furthermore, membrane complement regulatory proteins (mCRPs) have been shown to be over-expressed on the surface of cancer cells and render them resistant to autologous complement (Fishelson Z. et al., 2003. Mol Immunol 40:109-23).

Mechanisms protecting cells from heat-shock and from complement share some resemblance. For example, both of these shock responses depend on de-novo protein synthesis, exhibit similar functional kinetics, and studies have suggested a role for members of the 70 kilodalton heat shock protein (HSP70) family proteins in regulation of complement-mediated cytolysis (Fishelson Z. et al., 2001. Int Immunol. 13:983-991).

Mortalin, also known as GRP75, PBP74, mitochondrial HSP75 and mot-2, is a member of the HSP70 family (GeneCard #GC05M137967). This protein has been assigned multiple functions including stress response (Carette, J. et al., 2002. Int J Radiat Biol 78:183), glucose regulation, p53 inactivation, control of cell proliferation, differentiation, tumorigenesis and mitochondrial import (reviewed in Wadhwa, R. et al., 2002. Cell Stress Chaperones 7:309; Voisine, C. et al., 1999. Cell 97:565). Mortalin is thought to act as an intracellular protein, in mitochondria and several other cytoplasmic locations such as endoplasmic reticulum and cytoplasmic vesicles (Ran, Q. et al., 2000. Biochem Biophys Res Commun 275:174). Mortalin is ubiquitously and constitutively expressed in normal tissues, and has been shown to be displayed on the surface of mouse B-cells and macrophages (VanBuskirk, A. M. et al., 1991. J Immunol 146:500). Its expression level is upregulated in some tumors, such as neuroblastoma, lung adenocarcinoma, leukemia and ovarian cancer cells (Takano, S. et al., 1997. Exp Cell Res 237:38; Dundas, S R. et al., 2004. J Pathol 205:74; Shin, B. K. et al., 2003. J Biol Chem 278:7607), as well as during infection and inflammation (Kirmanoglou, K. et al., 2004. Basic Res Cardiol 99:404; Johannesen, J. et al., 2004. Autoimmunity 37:423). Overexpression of mortalin in normal cells considerably extends their lifespan (Kaul, S. C. et al., 2003. Exp Cell Res 286:96), while reduction of mortalin levels in immortalized cells causes growth arrest (Wadhwa, R. et al., 2004. J Gene Med 6:439; Wadhwa et al., 1994. Cell Struct Funct 19:1-10). In view of the expression of mortalin in cancers, the use of this protein as therapeutic target has been proposed (Wadhwa R. et al., 2002. Histol Histopathol 17:1173-7).

Several approaches have been proposed involving decreasing the levels/activity of HSP70 family proteins, such as mortalin, for treating diseases associated with pathological cells and treatable via complement-mediated cytolysis of such cells.

One approach involves administration of the mortalin inhibitor MKT-077 (formerly FJ-776) for treatment of cancers characterized by wild-type p53 (Wadhwa R. et al., 2000. Cancer Research 60, 6818-6821), chemo-resistant solid tumors (Propper D. J. et al., 1999. Ann. Oncol., 10: 923-927), untreatable/treatment-refractory solid tumors (Britten C. D. et al., 2000. Clin Cancer Res., 6: 42-49), or solid tumors of various lineages (Wadhwa R. et al., 2002. Cancer Res. 62:4434-8).

Yet another approach involves targeting mortalin using conventional and RNA-helicase-coupled hammerhead ribozymes for the treatment of cancers (Wadhwa R. et al., 2003. EMBO Rep 4: 595-601).

An additional approach suggests using mortalin as molecular target for treatment of hepatitis C virus-related hepatocellular carcinoma (Takashima M. et al., 2003. Proteomics. 3: 2487-93).

A further approach suggests employing inhibition of HSC70 with deoxyspergualin to increase the sensitivity of K562 human erythroleukemia cells to complement-mediated lysis (Fishelson Z. et al., 2001. Int Immunol. 13: 983-991).

Yet a further approach involves expression of mortalin anti-sense RNA in cancer cells for treatment of cancers characterized by compromised p53 and pRB functions and telomerase activity (Wadhwa R. et al., 2004. J Gene Med. 6: 439-44).

U.S. Publication No. 20060270622 discloses means of treating diseases associated with pathological cells by modulating the levels of mortalin in these cells and thus effecting the association of these cells with the complement system. According to the teachings of U.S. Publication No. 20060270622, decreasing the levels of mortalin level/activity can be affected by the use of anti-mortalin antibodies or by transfection with siRNA specific to mortalin. However, specific sequences of siRNA capable of down-regulating mortalin were not disclosed.

There is thus a widely recognized need for, and it would be highly advantageous to have maximally effective siRNAs capable of decreasing the levels of mortalin for the treatment of diseases such as cancer.

SUMMARY OF THE INVENTION

According to an aspect of some embodiments of the present invention there is provided a use of a siRNA molecule selected from the group consisting of SEQ ID NO: 173 to 344 for treating a disease associated with a pathological cell population in a subject in need thereof.

According to an aspect of some embodiments of the present invention there is provided an article of manufacture, comprising a packaging material identified for treating a disease associated with a pathological cell population, the packaging material comprising siRNA molecule selected from the group consisting of SEQ ID NO: 173 to 344 and an antibody capable of specifically binding a pathological cell population.

According to an aspect of some embodiments of the present invention there is provided a pharmaceutical composition comprising a siRNA molecule, wherein the siRNA molecule is selected from the group consisting of SEQ ID NO: 173 to 344.

According to some embodiments of the invention, the use further comprises administering to the subject an antibody capable of specifically binding the pathological cell population thereby increasing an association of complement with the pathological cell population in the subject.

According to some embodiments of the invention, the antibody comprises an antibody constant region.

According to some embodiments of the invention, the disease associated with the pathological cell population is selected from the group consisting of a tumoral disease, an infectious disease, an autoimmune disease and a transplantation-related disease.

According to some embodiments of the invention, the disease associated with the pathological cell population is cancer.

The present invention successfully addresses the shortcomings of the presently known configurations by providing siRNA molecules capable of down-regulating mortalin for treating diseases associated with pathological cell populations.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. In case of conflict, the patent specification, including definitions, will control. In addition, the materials, methods, and examples are illustrative only and not intended to be limiting.

As used herein, the terms "comprising" and "including" or grammatical variants thereof are to be taken as specifying the stated features, integers, steps or components but do not preclude the addition of one or more additional features, integers, steps, components or groups thereof. This term encompasses the terms "consisting of" and "consisting essentially of".

The phrase "consisting essentially of" or grammatical variants thereof when used herein are to be taken as specifying the stated features, integers, steps or components but do not preclude the addition of one or more additional features, integers, steps, components or groups thereof but only if the additional features, integers, steps, components or groups thereof do not materially alter the basic and novel characteristics of the claimed composition, device or method.

The term "method" refers to manners, means, techniques and procedures for accomplishing a given task including, but not limited to, those manners, means, techniques and procedures either known to, or readily developed from known manners, means, techniques and procedures by practitioners of the chemical, biological and biophysical arts.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

In the drawings.

DESCRIPTION OF THE PREFERRED EMBODIMENTS

Figure 1:
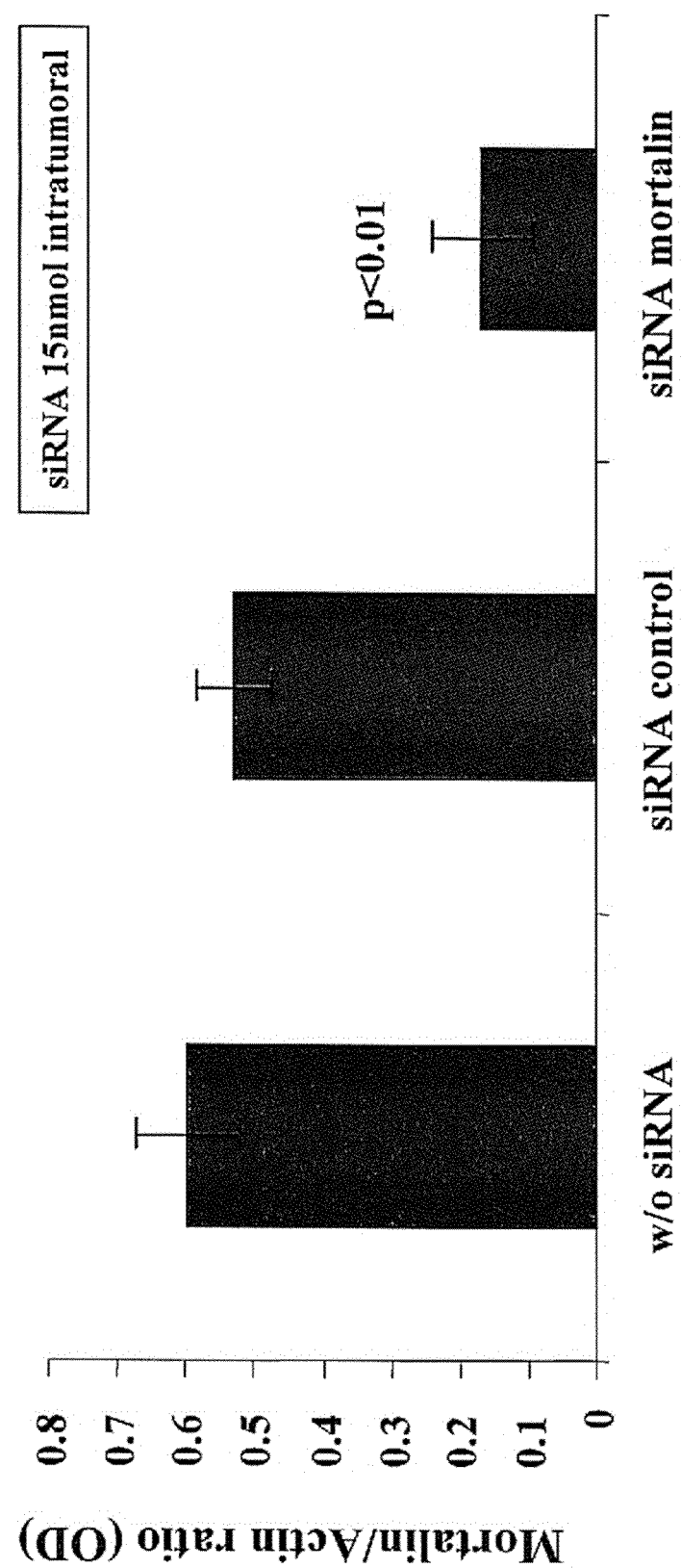
FIG. 1 is a bar graph depicting in vivo reduction of tumor mortalin expression level following intratumoral injection of mortalin specific siRNA. The results show levels of mortalin expression in K562 tumors two days after one intratumoral injection of 15 nmol mortalin specific siRNA1 (SEQ ID NO: 192, right column), control siRNA (SEQ ID NO: 345, middle column) or control PBS-injected tumors (left column). Tumor expression of mortalin was analyzed by t-test and was found to be significant ($P<0.01$). Of note, the results indicate a major difference between mortalin expression levels in tumors of mice treated with mortalin specific siRNA compared to mice treated with control siRNA.

The present invention is of a method of treating a disease associated with a pathological cell population, which is effected by decreasing the level of mortalin in pathological cells by the use of specific siRNA molecules; and is further of a pharmaceutical composition and an article of manufacture which comprises same.

Specifically, the present invention can be used for effectively regulating vesicular shedding of complement and for regulating complement-mediated cytotoxicity. As such, the present invention can be used for optimally treating diseases, such as tumoral, infectious, autoimmune and transplantation-related diseases, which are associated with pathological cells and are treatable via complement-mediated cytolysis of such cells.

The principles and operation of the present invention may be better understood with reference to the drawings and accompanying descriptions.

Before explaining at least one embodiment of the invention in detail, it is to be understood that the invention is not limited in its application to the details set forth in the following description or exemplified by the Examples. The invention is capable of other embodiments or of being practiced or carried out in various ways. Also, it is to be understood that the phraseology and terminology employed herein is for the purpose of description and should not be regarded as limiting.

Diseases such as tumoral, infectious, autoimmune and transplantation-related diseases, which are associated with pathological cells and are treatable via complement-mediated cytolysis of such cells represent numerous highly debilitating and/or lethal diseases for which no optimal therapy exists. In view of the possible role of HSP70 family proteins, such as mortalin, in mediating down-regulation of complement-mediated cytotoxicity, and in view of the over-expression of such proteins in pathological cells susceptible to elimination via such cytotoxicity, suitable modulation of levels and/or activity of such proteins may represent a potentially optimal strategy for treating such diseases.

Various approaches involving decreasing levels and/or activity of HSP70 family proteins, such as mortalin, for treating diseases associated with pathological cells and treatable via complement-mediated cytolysis of such cells have been described in the art. Such approaches involve administration of the mortalin inhibitor MKT-077 (formerly FJ-776) for treatment of cancers characterized by wild-type p53 (Wadhwa R. et al., 2000. Cancer Research 60: 6818-6821), chemo-resistant solid tumors (Propper D. J. et al., 1999. Ann. Oncol., 10: 923-927), untreatable/treatment-refractory solid tumors (Britten C. D. et al., 2000. Clin Cancer Res., 6: 42-49), or solid tumors of various lineages (Wadhwa R. et al., 2002. Cancer Res. 62: 4434-8).

Other approaches involve expression of mortalin antisense RNA in cancer cells for treatment of cancers characterized by compromised p53 and pRB functions and telomerase activity (Wadhwa R. et al., 2004. J Gene Med. 6:439-44).

Other approaches involve expression of conventional or RNA-helicase-coupled hammerhead ribozymes for treatment of cancers (Wadhwa R. et al., 2003. EMBO Rep. 2003 June; 4(6): 595-601) and using mortalin as molecular target for treatment of hepatitis C virus-related hepatocellular carcinoma (Takashima M. et al., 2003. Proteomics. 3:2487-93).

Additional approaches involve inhibition of HSC70 with deoxyspergulin to increase the sensitivity of K562 human erythroleukemia cells to complement-mediated lysis (Fishelson Z. et al., 2001. Int Immunol. 13:983-991).

While reducing the present invention to practice it was uncovered that in vivo, intratumoral injections of mortalin-specific siRNA effectively decrease mortalin expression level and tumor size (see FIGS. 1 and 2 in the Example section below). Thus, in vivo treatment of cancer with siRNA specific to mortalin can be efficiently used to reduce tumor size and to effectively treat such a disease in a subject in need thereof.

Thus, the present invention can be used to effectively treat a disease which is associated with pathological cells and/or which is associated with pathological complement-mediated cytotoxicity.

Thus, according to one aspect of the present invention there is provided a method of treating a disease associated with a pathological cell population, the method comprising administering to a subject in need thereof a siRNA molecule selected from the group consisting of SEQ ID NO: 173 to 344, thereby treating the disease associated with a pathological cell population.

As used herein, the term "treating" when relating to a disease of the present invention refers to preventing onset of the disease, alleviating, attenuating, palliating or eliminating the symptoms of a disease, slowing, reversing or arresting the progression of the disease, or curing the disease.

As used herein, the term "pathological" when relating to a pathological cell population of the present invention refers to a cell population whose elimination in a subject of the present invention having a disease associated with such a cell population can be used to treat the disease in the subject. The pathological cell population may be any nucleated cell population derived from an organism which expresses a mortalin. Exemplary pathological cells are described herein below.

As used herein, the phrase "subject in need thereof" refers to a subject which has the disease, or which is susceptible to having the disease. The subject may be any organism having an immune system capable of complement-mediated cytolysis. Preferably, the subject is a homeotherm, more preferably a mammal, more preferably a primate and most preferably a human.

As used herein, the term "mortalin polypeptide" refers to mammalian (e.g., human) mortalin polypeptide, such as set forth by GenBank Identifier gi:24234688 (SEQ ID NO: 347) or GenBank Accession No. NP_004125.3 or GenBank Accession AAH30634.1 including homologs, orthologs and isoforms thereof.

Down-regulating the mortalin polypeptide in the pathological cell population may be effected by administering to the subject an siRNA molecule capable of inducing degradation of an mRNA encoding the polypeptide.

Down-regulating the level of the mortalin polypeptide in the pathological cell population is preferably effected so as to maximally decrease, reduce and more preferably to essentially completely prevent mortalin polypeptide expression in the pathological cell population, so as to achieve optimal complement-mediated cytolysis of the pathological cell population, and hence optimal disease treatment.

Since down-regulation of mortalin decreases vesicular shedding of complement by a pathological cell population and thereby enables an increase of complement-mediated cytolysis of a pathological cell population, it can be used to treat any of various diseases associated with a pathological cell population, including tumoral, infectious, autoimmune and transplantation-related diseases.

It will be appreciated that a tumoral disease is associated with pathological tumor cells; that an infectious disease such as an intracellular pathogen infection, is associated with pathological pathogen-infected cells; that an autoimmune disease, such as one associated with immune cells such as T-lymphocytes or B-lymphocytes/antibodies specific for an autoantigen, or NK cells, is associated with such pathological immune cells; and that a transplantation-related disease such as graft rejection or graft-versus-host disease (GVHD), is associated with pathological recipient lymphocytes targeting graft antigens or pathological graft lymphocytes targeting autoantigens, respectively. As such, it will be appreciated that the method according to this aspect of the present invention can be used to treat such diseases by inducing cytolysis of such respective pathological cells associated therewith, in accordance with the teachings of the present invention, as described further hereinbelow.

Furthermore, it will be appreciated that any tumoral disease can be treated according to the teachings of the present invention. Such tumoral diseases are further described hereinbelow.

As described hereinabove, down-regulating the level of the mortalin polypeptide in the pathological cell population may be effected by administering to the subject a small interfering RNA (siRNA) molecule. RNA interference is a two step process. The first step, which is termed as the initiation step, input dsRNA is digested into 21-23 nucleotide (nt) small interfering RNAs (siRNA), probably by the action of Dicer, a member of the RNase III family of dsRNA-specific ribonucleases, which processes (cleaves) dsRNA (introduced directly or via a transgene or a virus) in an ATP-dependent manner. Successive cleavage events degrade the RNA to 19-21 by duplexes (siRNA), each with 2-nucleotide 3' overhangs [Hutvagner and Zamore Curr Opin Genetics and Development 12:225-232 (2002); and Bernstein, Nature 409: 363-366 (2001)].

In the effector step, the siRNA duplexes bind to a nuclease complex from the RNA-induced silencing complex (RISC). An ATP-dependent unwinding of the siRNA duplex is required for activation of the RISC. The active RISC then targets the homologous transcript by base pairing interactions and cleaves the mRNA into 12 nucleotide fragments from the 3' terminus of the siRNA [Hutvagner and Zamore Curr Op Gen Develop. 12:225-232 (2002); Hammond et al., 2001. Nat Rev Gen. 2:110-119 (2001); and Sharp Genes Dev. 15:485-90 (2001)]. Although the mechanism of cleavage is still to be elucidated, research indicates that each RISC contains a single siRNA and an RNase [Hutvagner and Zamore, Curr Opin Gen. Develop. 12:225-232 (2002)].

Because of the remarkable potency of RNAi, an amplification step within the RNAi pathway has been suggested. Amplification could occur by copying of the input dsRNAs which would generate more siRNAs, or by replication of the siRNAs formed. Alternatively or additionally, amplification could be effected by multiple turnover events of the RISC [Hammond et al., Nat Rev Gen. 2:110-119 (2001), Sharp Genes Dev. 15:485-90 (2001); Hutvagner and Zamore Curr Opin Gen. Develop. 12:225-232 (2002)]. Ample guidance for using RNAi to practice the present invention is provided in the literature of the art [refer, for example, to: Tuschl, ChemBiochem. 2:239-245 (2001); Cullen, Nat Immunol. 3:597-599 (2002); and Brantl, Biochem Biophys Acta 1575:15-25 (2002)].

Synthesis of RNAi molecules suitable for use with the present invention can be effected as follows. First, the mRNA sequence encoding the polypeptide of the present invention is scanned downstream of the AUG start codon for AA dinucleotide sequences. Occurrence of each AA and the 3' adjacent 19 nucleotides is recorded as potential siRNA target sites. Preferably, siRNA target sites are selected from the open reading frame, as untranslated regions (UTRs), being enriched in regulatory protein binding sites. UTR-binding proteins and/or translation initiation complexes may interfere with binding of the siRNA endonuclease complex [Tuschl, Chem Biochem. 2:239-245]. It will be appreciated though, that siRNAs directed at untranslated regions may also be effective, as demonstrated for GAPDH wherein siRNA directed at the 5' UTR mediated approximately 90% decrease in cellular GAPDH mRNA and completely abolished protein level (www.ambion.com/techlib/tn/142/3.html or www.ambion.com/techlib/tn/131/4.html).

Second, potential target sites are compared to an appropriate genomic database (e.g., human, mouse, rat etc.) using any sequence alignment software, such as the BLAST software available from the NCBI server (www.ncbi.nlm.nih.gov/BLAST/). Putative target sites which exhibit significant homology to other coding sequences are filtered out.

Qualifying target sequences are selected as template for siRNA synthesis. Preferred sequences are those including low G/C content as these have proven to be more effective in mediating gene silencing as compared to those with G/C content higher than 55%. Several target sites are preferably selected along the length of the target gene for evaluation. For better evaluation of the selected siRNAs, a negative control is preferably used in conjunction. Negative control siRNA preferably include the same nucleotide composition as the siRNAs but lack significant homology to the genome. Thus, a scrambled nucleotide sequence of the siRNA is preferably used, provided it does not display any significant homology to any other gene.

As is described in the Examples section which follows (refer, for example, to FIG. 1), siRNA can be used for down-regulating levels of mortalin polypeptides of the present invention (human mortalin).

It will be appreciated that a range of siRNA molecules specific to mortalin can be utilized according to the teachings of the present invention (SEQ ID NO: 173 to 344, Table 1, hereinbelow) to down-regulate mortalin level.

According to an exemplary embodiment, the siRNA molecule specific to mortalin is SEQ ID NO: 173, SEQ ID NO: 174, SEQ ID NO: 175, SEQ ID NO: 176, SEQ ID NO: 177, SEQ ID NO: 178, SEQ ID NO: 179, SEQ ID NO: 180, SEQ ID NO: 181, SEQ ID NO: 182, SEQ ID NO: 183, SEQ ID NO: 184, SEQ ID NO: 185, SEQ ID NO: 186, SEQ ID NO: 187, SEQ ID NO: 188, SEQ ID NO: 189, SEQ ID NO: 190, SEQ ID NO: 191, SEQ ID NO: 192, SEQ ID NO: 193, SEQ ID NO: 194, SEQ ID NO: 195, SEQ ID NO: 196, SEQ ID NO: 197, SEQ ID NO: 198, SEQ ID NO: 199, SEQ ID NO: 200, SEQ ID NO: 201, SEQ ID NO: 202, SEQ ID NO: 203, SEQ ID NO: 204, SEQ ID NO: 205, SEQ ID NO: 206, SEQ ID NO: 207, SEQ ID NO: 208, SEQ ID NO: 209, SEQ ID NO: 210, SEQ ID NO: 211, SEQ ID NO: 212, SEQ ID NO: 213, SEQ ID NO: 214, SEQ ID NO: 215, SEQ ID NO: 216, SEQ ID NO: 217, SEQ ID NO: 218, SEQ ID NO: 219, SEQ ID NO: 220, SEQ ID NO: 221, SEQ ID NO: 222, SEQ ID NO: 223, SEQ ID NO: 224, SEQ ID NO: 225, SEQ ID NO: 226, SEQ ID NO: 227, SEQ ID NO: 228, SEQ ID NO: 229, SEQ ID NO: 230, SEQ ID NO: 231, SEQ ID NO: 232, SEQ ID NO: 233, SEQ ID NO: 234, SEQ ID NO: 235, SEQ ID NO: 236, SEQ ID NO: 237, SEQ ID NO: 238, SEQ ID NO: 239, SEQ ID NO: 240, SEQ ID NO: 241, SEQ ID NO: 242, SEQ ID NO: 243, SEQ ID NO: 244, SEQ ID NO: 245, SEQ ID NO: 246, SEQ ID NO: 247, SEQ ID NO: 248, SEQ ID NO: 249, SEQ ID NO: 250, SEQ ID NO: 251, SEQ ID NO: 252, SEQ ID NO: 253, SEQ ID NO: 254, SEQ ID NO: 255, SEQ ID NO: 256, SEQ ID NO: 257, SEQ ID NO: 258, SEQ ID NO: 259, SEQ ID NO: 260, SEQ ID NO: 261, SEQ ID NO: 262, SEQ ID NO: 263, SEQ ID NO: 264, SEQ ID NO: 265, SEQ ID NO: 266, SEQ ID NO: 267, SEQ ID NO: 268, SEQ ID NO: 269, SEQ ID NO: 270, SEQ ID NO: 271, SEQ ID NO: 272, SEQ ID NO: 273, SEQ ID NO: 274, SEQ ID NO: 275, SEQ ID NO: 276, SEQ ID NO: 277, SEQ ID NO: 278, SEQ ID NO: 279, SEQ ID NO: 280, SEQ ID NO: 281, SEQ ID NO: 282, SEQ ID NO: 283, SEQ ID NO: 284, SEQ ID NO: 285, SEQ ID NO: 286, SEQ ID NO: 287, SEQ ID NO: 288, SEQ ID NO: 289, SEQ ID NO: 290, SEQ ID NO: 291, SEQ ID NO: 292, SEQ ID NO: 293, SEQ ID NO: 294, SEQ ID NO: 295, SEQ ID NO: 296, SEQ ID NO: 297, SEQ ID NO: 298, SEQ ID NO: 299, SEQ ID NO: 300, SEQ ID NO: 301, SEQ ID NO: 302, SEQ ID NO: 303, SEQ ID NO: 304, SEQ ID NO: 305, SEQ ID NO: 306, SEQ ID NO: 307, SEQ ID NO: 308, SEQ ID NO: 309, SEQ ID NO: 310, SEQ ID NO: 311, SEQ ID NO: 312, SEQ ID NO: 313, SEQ ID NO: 314, SEQ ID NO: 315, SEQ ID NO: 316, SEQ ID NO: 317, SEQ ID NO: 318, SEQ ID NO: 319, SEQ ID NO: 320, SEQ ID NO: 321, SEQ ID NO: 322, SEQ ID NO: 323, SEQ ID NO: 324, SEQ ID NO: 325, SEQ ID NO: 326, SEQ ID NO: 327, SEQ ID NO: 328, SEQ ID NO: 329, SEQ ID NO: 330, SEQ ID NO: 331, SEQ ID NO: 332, SEQ ID NO: 333, SEQ ID NO: 334, SEQ ID NO: 335, SEQ ID NO: 336, SEQ ID NO: 337, SEQ ID NO: 338, SEQ ID NO: 339, SEQ ID NO: 340, SEQ ID NO: 341, SEQ ID NO: 342, SEQ ID NO: 343 or SEQ ID NO: 344.

The siRNA sequences specified in Table 1 hereinbelow were specifically selected by analyzes of the mortalin mRNA sequence (SEQ ID NO: 346) using siRNA design tools (www.ambion.com/techlib/misc/siRNA_finder.html, www.dharmacon.com/DesignCenter/DesignCenterPage.aspx and https://rnaidesigner.invitrogen.com/sirna/).

TABLE 1 siRNA sequences for silencing mortalin

| Target sequence | Position in gene | GC content (%) | siRNA sequence (sense) |
|---|---|---|---|
| TGCCTCGTACTCCTCCATTTA (Seq id no: 1) | 82 | 47.6 | UGCCUCGUACUCCUCCAUUUA (Seq id no: 173) |
| TGGCCTTAGTCATGAGGCT (Seq id no: 2) | 199 | 47.6 | UGGCCUUAGUCAUGAGGCU (Seq id no: 174) |
| GGCGGGATTATGCATCAGA (Seq id no: 3) | 234 | 47.6 | GGCGGGAUUAUGCAUCAGA (Seq id no: 175) |
| GCAATCAAGGGAGCAGTTG (Seq id no: 4) | 254 | 47.6 | GCAAUCAAGGGAGCAGUUG (Seq id no: 176) |
| TCAAGGGAGCAGTTGTTGG (Seq id no: 5) | 258 | 47.6 | UCAAGGGAGCAGUUGUUGG (Seq id no: 177) |
| GGGAGCAGTTGTTGGTATT (Seq id no: 6) | 262 | 42.9 | GGGAGCAGUUGUUGGUAUU (Seq id no: 178) |
| CTCCTGCGTGGCAGTTATG (Seq id no: 7) | 298 | 52.4 | CUCCUGCGUGGCAGUUAUG (Seq id no: 179) |
| TGGCAGTTATGGAAGGTAA (Seq id no: 8) | 308 | 42 | UGGCAGUUAUGGAAGGUAA (Seq id no: 180) |
| GGTAAACAAGCAAAGGTGC (Seq id no: 9) | 320 | 42.9 | GGUAAACAAGCAAAGGUGC (Seq id no: 181) |
| ACAAGCAAAGGTGCTGGAG (Seq id no: 10) | 325 | 47.6 | ACAAGCAAAGGUGCUGGAG (Seq id no: 182) |
| GCAAAGGTGCTGGAGAATG (Seq id no: 11) | 329 | 47.6 | GCAAAGGUGCUGGAGAAUG (Seq id no: 183) |

TABLE 1-continued siRNA sequences for silencing mortalin

| Target sequence | Position in gene | GC content (%) | siRNA sequence (sense) |
|---|---|---|---|
| AGGTGCTGGAGAATGCCGA (Seq id no: 12) | 333 | 52.4 | AGGUGCUGGAGAAUGCCGA (Seq id no: 184) |
| TGCCGAAGGTGCCAGAACC (Seq id no: 13) | 346 | 57.1 | UGCCGAAGGUGCCAGAACC (Seq id no: 185) |
| GGTGCCAGAACCACCCCTT (Seq id no: 14) | 353 | 57.1 | GGUGCCAGAACCACCCCUU (Seq id no: 186) |
| CCACCCCTTCAGTTGTGGC (Seq id no: 15) | 363 | 57.1 | CCACCCCUUCAGUUGUGGC (Seq id no: 187) |
| GCGACAGGCTGTCACCAAC (Seq id no: 16) | 424 | 57.1 | GCGACAGGCUGUCACCAAC (Seq id no: 188) |
| AATTGTCCGTGCCTCCAAT (Seq id no: 17) | 535 | 42.9 | AAUUGUCCGUGCCUCCAAU (Seq id no: 189) |
| TTGTCCGTGCCTCCAATGG (Seq id no: 18) | 537 | 52.4 | UUGUCCGUGCCUCCAAUGG (Seq id no: 190) |
| TGGTGATGCCTGGGTTGAG (Seq id no: 19) | 553 | 52.4 | UGGUGAUGCCUGGGUUGAG (Seq id no: 191) |
| ATTGTATTCTCCGAGTCAG (Seq id no: 20) | 583 | 38.1 | AUUGUAUUCUCCGAGUCAG (Seq id no: 192) |
| GAGTCAGATTGGAGCATTT (Seq id no: 21) | 597 | 42 | GAGUCAGAUUGGAGCAUUU (Seq id no: 193) |
| GAGCATTTGTGTTGATGAA (Seq id no: 22) | 608 | 37 | GAGCAUUUGUGUUGAUGAA (Seq id no: 194) |
| GATGAAAGAGACTGCAGAA (Seq id no: 23) | 625 | 38.1 | GAUGAAAGAGACUGCAGAA (Seq id no: 195) |
| AGAGACTGCAGAAAATTAC (Seq id no: 24) | 631 | 33.3 | AGAGACUGCAGAAAAUUAC (Seq id no: 196) |
| AATTACTTGGGGCACACAG (Seq id no: 25) | 644 | 42.9 | AAUUACUUGGGGCACACAG (Seq id no: 197) |
| TTACTTGGGGCACACAGCA (Seq id no: 26) | 646 | 47.6 | UUACUUGGGGCACACAGCA (Seq id no: 198) |
| AAAATGCTGTGATCACAGT (Seq id no: 27) | 666 | 33.3 | AAAAUGCUGUGAUCACAGU (Seq id no: 199) |
| AATGCTGTGATCACAGTC (Seq id no: 28) | 668 | 42.9 | AAUGCUGUGAUCACAGUC (Seq id no: 200) |
| TGCTGTGATCACAGTCCCA (Seq id no: 29) | 670 | 47.6 | UGCUGUGAUCACAGUCCCA (Seq id no: 201) |
| TGACTCGCAGAGACAGGCC (Seq id no: 30) | 700 | 57.1 | UGACUCGCAGAGACAGGCC (Seq id no: 202) |
| AGATGCTGGCCAGATATCT (Seq id no: 31) | 724 | 42.9 | AGAUGCUGGCCAGAUAUCU (Seq id no: 203) |
| TGTGCTTCGGGTGATTAAT (Seq id no: 32) | 751 | 38.1 | UGUGCUUCGGGUGAUUAAU (Seq id no: 204) |
| TGAGCCCACAGCTGCTGCT (Seq id no: 33) | 769 | 57.1 | UGAGCCCACAGCUGCUGCU (Seq id no: 205) |
| TGCCTATGGTCTAGACAAA (Seq id no: 34) | 792 | 42 | UGCCUAUGGUCUAGACAAA (Seq id no: 206) |
| AGACAAATCAGAAGACAAA (Seq id no: 35) | 804 | 32 | AGACAAAUCAGAAGACAAA (Seq id no: 207) |
| GACAAAGTCATTGCTGTAT (Seq id no: 36) | 815 | 33.3 | GACAAAGUCAUUGCUGUAU (Seq id no: 208) |
| TGATTTAGGTGGTGGAACT (Seq id no: 37) | 837 | 42 | UGAUUUAGGUGGUGGAACU (Seq id no: 209) |
| GGAAATTCAGAAAGGAGTA (Seq id no: 38) | 873 | 37 | GGAAAUUCAGAAAGGAGUA (Seq id no: 210) |
| AGGAGTATTTGAGGTGAAA (Seq id no: 39) | 883 | 33.3 | AGGAGUAUUUGAGGUGAAA (Seq id no: 211) |
| ATCCACAAATGGGGATACC (Seq id no: 40) | 901 | 42.9 | AUCCACAAAUGGGGAUACC (Seq id no: 212) |
| ATGGGGATACCTTCTTAGG (Seq id no: 41) | 909 | 42.9 | AUGGGGAUACCUUCUUAGG (Seq id no: 213) |
| GACTTTGACCAGGCCTTGC (Seq id no: 42) | 935 | 52.4 | GACUUUGACCAGGCCUUGC (Seq id no: 214) |
| GGAGTTCAAGAGAGACCA (Seq id no: 43) | 970 | 42.9 | GGAGUUCAAGAGAGACCA (Seq id no: 215) |
| GAGAGAGACAGGGGTTGAT (Seq id no: 44) | 979 | 47.6 | GAGAGAGACAGGGGUUGAU (Seq id no: 216) |
| AGACAACATGGCACTTCAG (Seq id no: 45) | 1006 | 42.9 | AGACAACAUGGCACUUCAG (Seq id no: 217) |
| CATGGCACTTCAGAGGGTA (Seq id no: 46) | 1012 | 47.6 | CAUGGCACUUCAGAGGGUA (Seq id no: 218) |
| GCTGCTGAAAAGGCTAAAT (Seq id no: 47) | 1037 | 38.1 | GCUGCUGAAAAGGCUAAAU (Seq id no: 219) |

TABLE 1-continued siRNA sequences for silencing mortalin

| Target sequence | Position in gene | GC content (%) | siRNA sequence (sense) |
|---|---|---|---|
| AAGGCTAAATGTGAACTCT (Seq id no: 48) | 1046 | 33.3 | AAGGCUAAAUGUGAACUCU (Seq id no: 220) |
| GGCTAAATGTGAACTCTCC (Seq id no: 49) | 1048 | 42.9 | GGCUAAAUGUGAACUCUCC (Seq id no: 221) |
| ATGTGAACTCTCCTCATCT (Seq id no: 50) | 1054 | 38.1 | AUGUGAACUCUCCUCAUCU (Seq id no: 222) |
| CTCTCCTCATCTGTGCAGA (Seq id no: 51) | 1061 | 47.6 | CUCUCCUCAUCUGUGCAGA (Seq id no: 223) |
| TTTGCCCTATCTTACAATG (Seq id no: 52) | 1090 | 33.3 | UUUGCCCUAUCUUACAAUG (Seq id no: 224) |
| TGGATTCTTCTGGACCCAA (Seq id no: 53) | 1107 | 42.9 | UGGAUUCUUCUGGACCCAA (Seq id no: 225) |
| GGACCCAAGCATTTGAATA (Seq id no: 54) | 1120 | 42 | GGACCCAAGCAUUUGAAUA (Seq id no: 226) |
| TATGAAGTTGACCCGTGCT (Seq id no: 55) | 1135 | 42.9 | UAUGAAGUUGACCCGUGCU (Seq id no: 227) |
| GTTGACCCGTGCTCAATTT (Seq id no: 56) | 1141 | 42.9 | GUUGACCCGUGCUCAAUUU (Seq id no: 228) |
| TTTGAAGGGATTGTCACTG (Seq id no: 57) | 1157 | 38.1 | UUUGAAGGGAUUGUCACUG (Seq id no: 229) |
| GGGATTGTCACTGATCTAA (Seq id no: 58) | 1163 | 38.1 | GGGAUUGUCACUGAUCUAA (Seq id no: 230) |
| GATCTAATCAGAAGGACTA (Seq id no: 59) | 1177 | 37 | GAUCUAAUCAGAAGGACUA (Seq id no: 231) |
| TCAGAAGGACTATCGCTCC (Seq id no: 60) | 1182 | 47.6 | UCAGAAGGACUAUCGCUCC (Seq id no: 232) |
| GGACTATCGCTCCATGCCA (Seq id no: 61) | 1188 | 52.4 | GGACUAUCGCUCCAUGCCA (Seq id no: 233) |
| AAAGCTATGCAAGATGCAG (Seq id no: 62) | 1208 | 38.1 | AAAGCUAUGCAAGAUGCAG (Seq id no: 234) |
| AGCTATGCAAGATGCAGAA (Seq id no: 63) | 1210 | 38.1 | AGCUAUGCAAGAUGCAGAA (Seq id no: 235) |
| GATGCAGAAGTCAGCAAGA (Seq id no: 64) | 1220 | 42.9 | GAUGCAGAAGUCAGCAAGA (Seq id no: 236) |
| GTCAGCAAGAGTGACATAG (Seq id no: 65) | 1229 | 42.9 | GUCAGCAAGAGUGACAUAG (Seq id no: 237) |
| GAGTGACATAGGAGAAGTG (Seq id no: 66) | 1237 | 42.9 | GAGUGACAUAGGAGAAGUG (Seq id no: 238) |
| TGACATAGGAGAAGTGATT (Seq id no: 67) | 1242 | 37 | UGACAUAGGAGAAGUGAUU (Seq id no: 239) |
| GTGATTCTTGTGGGTGGCA (Seq id no: 68) | 1253 | 47.6 | GUGAUUCUUGUGGGUGGCA (Seq id no: 240) |
| GGTTCAGCAGACTGTACAG (Seq id no: 69) | 1288 | 47.6 | GGUUCAGCAGACUGUACAG (Seq id no: 241) |
| GTAAAGCTGTCAATCCTGA (Seq id no: 70) | 1329 | 38.1 | GUAAAGCUGUCAAUCCUGA (Seq id no: 242) |
| AGCTGTCAATCCTGATGAG (Seq id no: 71) | 1333 | 42.9 | AGCUGUCAAUCCUGAUGAG (Seq id no: 243) |
| TCCTGATGAGGCTGTGGCC (Seq id no: 72) | 1342 | 57.1 | UCCUGAUGAGGCUGUGGCC (Seq id no: 244) |
| ACTCTAGGAGGTGTCTTTA (Seq id no: 73) | 1451 | 38.1 | ACUCUAGGAGGUGUCUUUA (Seq id no: 245) |
| TAGGAATACCACTATTCCA (Seq id no: 74) | 1483 | 33.3 | UAGGAAUACCACUAUUCCA (Seq id no: 246) |
| TACCACTATTCCAACCAAG (Seq id no: 75) | 1489 | 38.1 | UACCACUAUUCCAACCAAG (Seq id no: 247) |
| CCAAGAAGAGCCAGGTATT (Seq id no: 76) | 1503 | 42.9 | CCAAGAAGAGCCAGGUAUU (Seq id no: 248) |
| GAAGAGCCAGGTATTCTCT (Seq id no: 77) | 1507 | 42.9 | GAAGAGCCAGGUAUUCUCU (Seq id no: 249) |
| GAGCCAGGTATTCTCTACT (Seq id no: 78) | 1510 | 42.9 | GAGCCAGGUAUUCUCUACU (Seq id no: 250) |
| ACGCAAGTGGAAATTAAAG (Seq id no: 79) | 1544 | 33.3 | ACGCAAGUGGAAAUUAAAG (Seq id no: 251) |
| GTGGAAATTAAAGTGTGTC (Seq id no: 80) | 1550 | 33.3 | GUGGAAAUUAAAGUGUGUC (Seq id no: 252) |
| ATTAAAGTGTGTCAGGGTG (Seq id no: 81) | 1556 | 38.1 | AUUAAAGUGUGUCAGGGUG (Seq id no: 253) |
| AGTGTGTCAGGGTGAAAGA (Seq id no: 82) | 1561 | 42.9 | AGUGUGUCAGGGUGAAAGA (Seq id no: 254) |
| AGAGAGATGGCTGGAGACA (Seq id no: 83) | 1577 | 47.6 | AGAGAGAUGGCUGGAGACA (Seq id no: 255) |

TABLE 1-continued siRNA sequences for silencing mortalin

| Target sequence | Position in gene | GC content (%) | siRNA sequence (sense) |
|---|---|---|---|
| CAAACTCCTTGGACAGTTT (Seq id no: 84) | 1597 | 38.1 | CAAACUCCUUGGACAGUUU (Seq id no: 256) |
| ACTCCTTGGACAGTTTACT (Seq id no: 85) | 1600 | 38.1 | ACUCCUUGGACAGUUUACU (Seq id no: 257) |
| TGGGATAGTACATGTTTCT (Seq id no: 86) | 1687 | 33.3 | UGGGAUAGUACAUGUUUCU (Seq id no: 258) |
| GATAGTACATGTTTCTGCTAA (Seq id no: 87) | 1692 | 33.3 | GAUAGUACAUGUUUCUGCUAA (Seq id no: 259) |
| AGATAAAGGCACAGGACGT (Seq id no: 88) | 1711 | 42.9 | AGAUAAAGGCACAGGACGU (Seq id no: 260) |
| AGGCACAGGACGTGAGCAG (Seq id no: 89) | 1717 | 57.1 | AGGCACAGGACGUGAGCAG (Seq id no: 261) |
| TCCAGTCTTCTGGTGGATT (Seq id no: 90) | 1746 | 42.9 | UCCAGUCUUCUGGUGGAUU (Seq id no: 262) |
| GTGGATTAAGCAAAGATGATA (Seq id no: 91) | 1760 | 33.3 | GUGGAUUAAGCAAAGAUGAUA (Seq id no: 263) |
| ATGCAGAGAAATATGCTGA (Seq id no: 92) | 1797 | 33.3 | AUGCAGAGAAAUAUGCUGA (Seq id no: 264) |
| GCAGAGAAATATGCTGAAGAA (Seq id no: 93) | 1801 | 38.1 | GCAGAGAAAUAUGCUGAAGAA (Seq id no: 265) |
| ATATGCTGAAGAAGACCGG (Seq id no: 94) | 1807 | 42.9 | AUAUGCUGAAGAAGACCGG (Seq id no: 266) |
| GAAGACCGGCGAAAGAAGG (Seq id no: 95) | 1817 | 52.4 | GAAGACCGGCGAAAGAAGG (Seq id no: 267) |
| GACCGGCGAAAGAAGGAAC (Seq id no: 96) | 1820 | 52.4 | GACCGGCGAAAGAAGGAAC (Seq id no: 268) |
| CGAAAGAAGGAACGAGTTGAA (Seq id no: 97) | 1828 | 42.9 | CGAAAGAAGGAACGAGUUGAA (Seq id no: 269) |
| GAAGGAACGAGTTGAAGC (Seq id no: 98) | 1830 | 42.9 | AGAAGGAACGAGUUGAAGC (Seq id no: 270) |
| GGAACGAGTTGAAGCAGTT (Seq id no: 99) | 1834 | 42.9 | GGAACGAGUUGAAGCAGUU (Seq id no: 271) |
| CGAGTTGAAGCAGTTAATA (Seq id no: 100) | 1838 | 33.3 | CGAGUUGAAGCAGUUAAUA (Seq id no: 272) |
| GCAGTTAATATGGCTGAAG (Seq id no: 101) | 1847 | 38.1 | GCAGUUAAUAUGGCUGAAG (Seq id no: 273) |
| TATGGCTGAAGGAATCATT (Seq id no: 102) | 1855 | 33.3 | UAUGGCUGAAGGAAUCAUU (Seq id no: 274) |
| GGAATCATTCACGACACAG (Seq id no: 103) | 1865 | 42.9 | GGAAUCAUUCACGACACAG (Seq id no: 275) |
| TCATTCACGACACAGAAAC (Seq id no: 104) | 1869 | 38.1 | UCAUUCACGACACAGAAAC (Seq id no: 276) |
| ACAGAAACCAAGATGGAAGAA (Seq id no: 105) | 1882 | 38.1 | ACAGAAACCAAGAUGGAAGAA (Seq id no: 277) |
| ACCAAGATGGAAGAATTCA (Seq id no: 106) | 1886 | 33.3 | ACCAAGAUGGAAGAAUUCA (Seq id no: 278) |
| GATGGAAGAATTCAAGGAC (Seq id no: 107) | 1891 | 38.1 | GAUGGAAGAAUUCAAGGAC (Seq id no: 279) |
| GAATTCAAGGACCAATTAC (Seq id no: 108) | 1898 | 33.3 | GAAUUCAAGGACCAAUUAC (Seq id no: 280) |
| TTCAAGGACCAATTACCTG (Seq id no: 109) | 1901 | 38.1 | UUCAAGGACCAAUUACCUG (Seq id no: 281) |
| GGACCAATTACCTGCTGAT (Seq id no: 110) | 1906 | 42.9 | GGACCAAUUACCUGCUGAU (Seq id no: 282) |
| TTACCTGCTGATGAGTGCA (Seq id no: 111) | 1913 | 42.9 | UUACCUGCUGAUGAGUGCA (Seq id no: 283) |
| CAAGCTGAAAGAAGAGATTT (Seq id no: 112) | 1933 | 33.3 | CAAGCUGAAAGAAGAGAUU (Seq id no: 284) |
| GCTGAAAGAAGAGATTTCC (Seq id no: 113) | 1936 | 38.1 | GCUGAAAGAAGAGAUUUCC (Seq id no: 285) |
| GAGATTTCCAAAATGAGGG (Seq id no: 114) | 1946 | 38.1 | GAGAUUUCCAAAAUGAGGG (Seq id no: 286) |
| AATGAGGGAGCTCCTGGCT (Seq id no: 115) | 1957 | 52.4 | AAUGAGGGAGCUCCUGGCU (Seq id no: 287) |
| TGAGGGAGCTCCTGGCTAG (Seq id no: 116) | 1959 | 57.1 | UGAGGGAGCUCCUGGCUAG (Seq id no: 288) |
| AAGACAGCGAAACAGGAGA (Seq id no: 117) | 1980 | 42.9 | AAGACAGCGAAACAGGAGA (Seq id no: 289) |
| GACAGCGAAACAGGAGAAA (Seq id no: 118) | 1982 | 42.9 | GACAGCGAAACAGGAGAAA (Seq id no: 290) |
| CAGCGAAACAGGAGAAAAT (Seq id no: 119) | 1986 | 42 | CAGCGAAACAGGAGAAAAU (Seq id no: 291) |

TABLE 1-continued siRNA sequences for silencing mortalin

| Target sequence | Position in gene | GC content (%) | siRNA sequence (sense) |
|---|---|---|---|
| GCTAGAAAAGACAGCGAAA (Seq id no: 120) | 1975 | 42 | GCUAGAAAAGACAGCGAAA (Seq id no: 292) |
| AATATTAGACAGGCAGCAT (Seq id no: 121) | 2000 | 33.3 | AAUAUUAGACAGGCAGCAU (Seq id no: 293) |
| TATTAGACAGGCAGCATCC (Seq id no: 122) | 2002 | 42.9 | UAUUAGACAGGCAGCAUCC (Seq id no: 294) |
| GCTGTTCGAAATGGCATAC (Seq id no: 123) | 2044 | 42.9 | GCUGUUCGAAAUGGCAUAC (Seq id no: 295) |
| ATGGCATACAAAAAGATGG (Seq id no: 124) | 2054 | 33.3 | AUGGCAUACAAAAAGAUGG (Seq id no: 296) |
| AAAGATGGCATCTGAGCGA (Seq id no: 125) | 2065 | 42.9 | AAAGAUGGCAUCUGAGCGA (Seq id no: 297) |
| AGATGGCATCTGAGCGAGA (Seq id no: 126) | 2067 | 47.6 | AGAUGGCAUCUGAGCGAGA (Seq id no: 298) |
| GCGAGAAGGCTCTGGAAGT (Seq id no: 127) | 2082 | 58 | GCGAGAAGGCUCUGGAAGU (Seq id no: 299) |
| GGCTCTGGAAGTTCTGGCA (Seq id no: 128) | 2087 | 52.4 | GGCUCUGGAAGUUCUGGCA (Seq id no: 300) |
| GTTCTGGCACTGGGGAACA (Seq id no: 129) | 2097 | 52.4 | GUUCUGGCACUGGGGAACA (Seq id no: 301) |
| CAAAAGGAAGATCAAAAGG (Seq id no: 130) | 2114 | 33.3 | CAAAAGGAAGAUCAAAAGG (Seq id no: 302) |
| AAGGAAGATCAAAAGGAGG (Seq id no: 131) | 2117 | 38.1 | AAGGAAGAUCAAAAGGAGG (Seq id no: 303) |
| GGAAGATCAAAAGGAGGAA (Seq id no: 132) | 2119 | 38.1 | GGAAGAUCAAAAGGAGGAA (Seq id no: 304) |
| GATCAAAAGGAGGAAAAAC (Seq id no: 133) | 2123 | 33.3 | GAUCAAAAGGAGGAAAAAC (Seq id no: 305) |
| TAGCAGAAATTTTGAAGCC (Seq id no: 134) | 2150 | 33.3 | UAGCAGAAAUUUUGAAGCC (Seq id no: 306) |
| ATTTTGAAGCCAGAAGGAC (Seq id no: 135) | 2158 | 38.1 | AUUUUGAAGCCAGAAGGAC (Seq id no: 307) |
| GCCAGAAGGACAACATATG (Seq id no: 136) | 2166 | 42.9 | GCCAGAAGGACAACAUAUG (Seq id no: 308) |
| GGACAACATATGAAGCTTA (Seq id no: 137) | 2173 | 33.3 | GGACAACAUAUGAAGCUUA (Seq id no: 309) |
| CATATGAAGCTTAGGAGTG (Seq id no: 138) | 2179 | 38.1 | CAUAUGAAGCUUAGGAGUG (Seq id no: 310) |
| GCTTAGGAGTGAAGAGACT (Seq id no: 139) | 2187 | 42.9 | GCUUAGGAGUGAAGAGACU (Seq id no: 311) |
| GAGACTTCCTGAGCAGAAA (Seq id no: 140) | 2202 | 42.9 | GAGACUUCCUGAGCAGAAA (Seq id no: 312) |
| ATGGGCGAACTTCAGTCTT (Seq id no: 141) | 2218 | 42.9 | AUGGGCGAACUUCAGUCUU (Seq id no: 313) |
| CTTCAGTCTTTTTACTGTG (Seq id no: 142) | 2227 | 33.3 | CUUCAGUCUUUUUACUGUG (Seq id no: 314) |
| TGGACAGTGATTCTAACAG (Seq id no: 143) | 2316 | 38.1 | UGGACAGUGAUUCUAACAG (Seq id no: 315) |
| GACAGTGATTCTAACAGTATA (Seq id no: 144) | 2320 | 33.3 | GACAGUGAUUCUAACAGUAUA (Seq id no: 316) |
| TATTCTATGTCCCTAGCCT (Seq id no: 145) | 2349 | 38.1 | UAUUCUAUGUCCCUAGCCU (Seq id no: 317) |
| AAGGAGGTAGGATGAATTG (Seq id no: 146) | 2390 | 38.1 | AAGGAGGUAGGAUGAAUUG (Seq id no: 318) |
| GGAGGTAGGATGAATTGAT (Seq id no: 147) | 2392 | 38.1 | GGAGGUAGGAUGAAUUGAU (Seq id no: 319) |
| GTGACCATATTTTCAAGGG (Seq id no: 148) | 2442 | 38.1 | GUGACCAUAUUUUCAAGGG (Seq id no: 320) |
| GGGGTGAAACCATCTCGCA (Seq id no: 149) | 2458 | 52.4 | GGGGUGAAACCAUCUCGCA (Seq id no: 321) |
| ACCATCTCGCACACAGCAA (Seq id no: 150) | 2466 | 47.6 | ACCAUCUCGCACACAGCAA (Seq id no: 322) |
| TGAAGGTAGTCATCCATAG (Seq id no: 151) | 2485 | 38.1 | UGAAGGUAGUCAUCCAUAG (Seq id no: 323) |
| GGTAGTCATCCATAGACTT (Seq id no: 152) | 2489 | 38.1 | GGUAGUCAUCCAUAGACUU (Seq id no: 324) |
| CCATAGACTTGAAATGAGA (Seq id no: 153) | 2500 | 37 | CCAUAGACUUGAAAUGAGA (Seq id no: 325) |
| ATGAGACCACATATGGGGA (Seq id no: 154) | 2511 | 42.9 | AUGAGACCACAUAUGGGGA (Seq id no: 326) |
| CTGAGGCCTTGCAAGTCAA (Seq id no: 155) | 2592 | 47.6 | CUGAGGCCUUGCAAGUCAA (Seq id no: 327) |

TABLE 1-continued siRNA sequences for silencing mortalin

| Target sequence | Position in gene | GC content (%) | siRNA sequence (sense) |
|---|---|---|---|
| GTCAAGCTGGCTGTGCCAT (Seq id no: 156) | 2606 | 52.4 | GUCAAGCUGGCUGUGCCAU (Seq id no: 328) |
| GCTGGCTGTGCCATGTTTG (Seq id no: 157) | 2611 | 52.4 | GCUGGCUGUGCCAUGUUUG (Seq id no: 329) |
| TCTAGAACAATGGGAAACT (Seq id no: 158) | 2647 | 33.3 | UCUAGAACAAUGGGAAACU (Seq id no: 330) |
| CAATGGGAAACTTAGCTAT (Seq id no: 159) | 2654 | 33.3 | CAAUGGGAAACUUAGCUAU (Seq id no: 331) |
| AACAAGGTAGGAATGAGGC (Seq id no: 160) | 2695 | 42.9 | AACAAGGUAGGAAUGAGGC (Seq id no: 332) |
| CAAGGTAGGAATGAGGCTA (Seq id no: 161) | 2697 | 42.9 | CAAGGUAGGAAUGAGGCUA (Seq id no: 333) |
| GGTAGGAATGAGGCTAGAC (Seq id no: 162) | 2700 | 47.6 | GG UAGGAAUGAGGCUAGAC (Seq id no: 334) |
| TGAGGCTAGACCTTTAACT (Seq id no: 163) | 2708 | 38.1 | UGAGGCUAGACCUUUAACU (Seq id no: 335) |
| CTTCCCTAAGGCATACTTT (Seq id no: 164) | 2725 | 38.1 | CUUCCCUAAGGCAUACUUU (Seq id no: 336) |
| GGCATACTTTTCTAGCTAC (Seq id no: 165) | 2734 | 38.1 | GGCAUACUUUUCUAGCUAC (Seq id no: 337) |
| GAAGAATTCAAGGACCAATTA (Seq id no: 166) | 1897 | 33.3 | GAAGAAUUCAAGGACCAAUUA (Seq id no: 338) |
| ACCTGCTGATGAGTGCAACAA (Seq id no: 167) | 1917 | 47.6 | ACCUGCUGAUGAGUGCAACAA (Seq id no: 339) |
| GAAGAGACTTCCTGAGCAGAA (Seq id no: 168) | 2199 | 47.6 | GAAGAGACUUCCUGAGCAGAA (Seq id no: 340) |
| GACTTGAAATGAGACCACATA (Seq id no: 169) | 2505 | 38.1 | GACUUGAAAUGAGACCACAUA (Seq id no: 341) |
| ATCCTTCTAGTTAGCCTAGTA (Seq id no: 170) | 2536 | 38.1 | AUCCUUCUAGUUAGCCUAGUA (Seq id no: 342) |
| GCAGAGGAATCTAGAACAA (Seq id no: 171) | 2640 | 42 | GCAGAGGAAUCUAGAACAA (Seq id no: 343) |
| AGGAATGAGGCTAGACCTTTA (Seq id no: 172) | 2705 | 42.9 | AGGAAUGAGGCUAGACCUUUA (Seq id no: 344) |

According to one embodiment, the method of treating the disease associated with the pathological cell population further comprises administering to the subject an antibody capable of specifically binding the pathological cell population thereby increasing an association of complement with the pathological cell population in a subject in need of treatment.

As used herein, the term "complement" when relating to an association of complement with a pathological cell population of the present invention, refers to any complement protein, or any complex of complement proteins, including activated complement C1, C3 and C4 which are capable of attaching (bridging) between leukocytes and lymphocytes and nucleated cells and complement membrane attack complex (MAC)/C5b-9, which is capable of facilitating cytolysis of a nucleated cell.

According to the teachings of the present invention, increasing an association of complement with the pathological cell population can be advantageously used for augmenting cytolysis of the pathological cells in a pathological/therapeutic context wherein there is association of complement with the pathological cells at supra-lytic levels in the subject. Alternately, increasing the association can be used for inducing cytolysis of pathological cells in a pathological/therapeutic context wherein there is no association of complement with the pathological cells, or where the association occurs at sub-lytic levels, in the subject.

Preferably, increasing the association of complement with the pathological cell population is effected by administering to the subject an antibody e.g. an antibody constant region, capable of binding the pathological cells, which enables initiation of the classical pathway of complement activation. The antibody constant region enabling initiation of the classical pathway of complement activation is preferably the constant region of Ig(mu) or Ig(gamma), the heavy chains of antibodies having the IgM or IgG isotype, respectively. Thus, natural antibodies having a constant region capable of initiating the classical pathway of complement activation are typically of the IgM or IgG isotype. It will be appreciated that administering to the subject an antibody capable of specifically binding the pathological cells and having a constant region capable of initiating the classical pathway of complement activation will facilitate membrane attack complex assembly at the cell surface of cells of the pathological cell population and will result in concomitant complement-mediated cytolysis of the pathological cells.

Increasing the association of complement with the pathological cell population can be achieved by administering to the subject essentially any compound which comprises a moiety capable of initiating assembly of attack complex such as a suitable antibody constant region, and which further comprises a moiety capable of specifically binding the pathological cell population.

It will be appreciated that the compound may be assembled at the surface of cells of the pathological population by administering to the subject a first compound which can specifically bind the pathological cells, and a second compound which can specifically bind the first compound and which comprises a suitable antibody constant region for initiating complement mediated cytolysis. Such a scheme can be performed with enhanced safety by administering to the subject the first compound, allowing the first compound to specifically bind to the pathological cells and allowing the weakly/non-specifically bound or unbound molecules thereof to exit the circulation, and only afterwards administering to the subject the second compound. The first and second compounds may be conjugated to complementary affinity binding moieties, such as streptavidin and biotin, so as to achieve optimally rapid, specific and stable binding therebetween following administration of the second compound. Increasing the association of complement with the pathological cell population according to such a scheme will result in minimal non-specific association of the antibody constant region with, and concomitant cytolysis of, cells other than the pathological cell population.

Examples of types of suitable moieties capable of specifically binding a pathological cell population of the present invention include antibody fragments capable of specifically binding surface molecules of the pathological cells, and specific biological ligands of cell surface molecules of the pathological cells.

It will be well within the purview of one of ordinary skill in the art to obtain a compound which comprises a moiety capable of specifically binding a target antigen conjugated to an antibody constant region. For example, a fusion protein which comprises a non-immunoglobulin polypeptide moiety capable of specifically binding a pathological cell and which comprises an antibody constant region of the present invention may be produced according to standard art recombinant protein production methodology (for guidance, refer, for example, to the list of references provided in the introductory paragraph to the Examples section which follows) for producing such chimeric immunoglobulins, which may be referred to as "immunoadhesins" or "Fc fusion proteins" in the art.

Preferably, an antibody constant region of the present invention specifically binds at least one epitope of a target antigen (on the pathological cells).

As used herein, the term "epitope" refers to any antigenic determinant on an antigen to which the antibody specifically binds.

Epitopic determinants usually consist of chemically active surface groupings of molecules such as amino acids or carbohydrate side chains and usually have specific three dimensional structural characteristics, as well as specific charge characteristics.

As used herein, the term "antibody constant region" refers to the non-variable part of the antibody molecule that is capable of modulating immune cell activity.

Methods of generating antibodies (i.e., monoclonal and polyclonal) are well known in the art. Antibodies may be generated via any one of several methods known in the art, which methods can employ induction of in-vivo production of antibody molecules, screening of immunoglobulin libraries (Orlandi D. R. et al., 1989. Proc. Natl. Acad. Sci. U.S.A. 86:3833-3837; Winter G. et al., 1991. Nature 349:293-299) or generation of monoclonal antibody molecules by continuous cell lines in culture. These include, but are not limited to, the hybridoma technique, the human B-cell hybridoma technique, and the Epstein-Barr virus (EBV)-hybridoma technique (Kohler G. et al., 1975. Nature 256:495-497; Kozbor D. et al., 1985. J. Immunol. Methods 81:31-42; Cote R J. et al., 1983. Proc. Natl. Acad. Sci. U.S.A. 80:2026-2030; Cole S P. et al., 1984. Mol. Cell. Biol. 62:109-120).

In cases where target antigens are too small to elicit an adequate immunogenic response when generating antibodies in-vivo, such antigens (haptens) can be coupled to antigenically neutral carriers such as keyhole limpet hemocyanin (KLH) or serum albumin [e.g., bovine serum albumin (BSA)] carriers (see, for example, U.S. Pat. Nos. 5,189,178 and 5,239,078]. Coupling a hapten to a carrier can be effected using methods well known in the art. For example, direct coupling to amino groups can be effected and optionally followed by reduction of the imino linkage formed. Alternatively, the carrier can be coupled using condensing agents such as dicyclohexyl carbodiimide or other carbodiimide dehydrating agents. Linker compounds can also be used to effect the coupling; both homobifunctional and heterobifunctional linkers are available from Pierce Chemical Company, Rockford, Ill. The resulting immunogenic complex can then be injected into suitable mammalian subjects such as mice, rabbits, and the like. Suitable protocols involve repeated injection of the immunogen in the presence of adjuvants according to a schedule which boosts production of antibodies in the serum. The titers of the immune serum can readily be measured using immunoassay procedures which are well known in the art.

The antisera obtained can be used directly or monoclonal antibodies may be obtained as described hereinabove.

Antibody fragments can be obtained using methods well known in the art. [(see, for example, Harlow and Lane, "Antibodies: A Laboratory Manual", Cold Spring Harbor Laboratory, New York, (1988)]. For example, antibody fragments according to the present invention can be prepared by proteolytic hydrolysis of the antibody or by expression in $E.\ coli$ or mammalian cells (e.g., Chinese hamster ovary cell culture or other protein expression systems) of DNA encoding the fragment.

Alternatively, antibody fragments can be obtained by pepsin or papain digestion of whole antibodies by conventional methods. An $(Fab')_2$ antibody fragments can be produced by enzymatic cleavage of antibodies with pepsin to provide a 5S fragment. This fragment can be further cleaved using a thiol reducing agent, and optionally a blocking group for the sulfhydryl groups resulting from cleavage of disulfide linkages to produce 3.5S Fab' monovalent fragments. Alternatively, enzymatic cleavage using pepsin produces two monovalent Fab' fragments and an Fc fragment directly. Ample guidance for practicing such methods is provided in the literature of the art (for example, refer to: Goldenberg, U.S. Pat. Nos. 4,036,945 and 4,331,647; Porter, R R., 1959. Biochem. J. 73:119-126). Other methods of cleaving antibodies, such as separation of heavy chains to form monovalent light-heavy chain fragments, further cleavage of fragments, or other enzymatic, chemical, or genetic techniques may also be used, so long as the fragments bind to the antigen that is recognized by the intact antibody.

It will be appreciated that for human therapy, humanized antibodies may be preferably used. Humanized forms of non human (e.g., murine) antibodies are genetically engineered chimeric antibodies or antibody fragments having—preferably minimal—portions derived from non human antibodies. Humanized antibodies include antibodies in which complementary determining regions of a human antibody (recipient antibody) are replaced by residues from a complementarity determining region of a non human species (donor antibody) such as mouse, rat or rabbit having the desired functionality. In some instances, Fv framework residues of the human antibody are replaced by corresponding non human residues. Humanized antibodies may also comprise residues which are found neither in the recipient antibody nor in the imported complementarity determining region or framework sequences. In general, the humanized antibody will comprise substantially all of at least one, and typically two, variable domains, in which all or substantially all of the complementarity determining regions correspond to those of a non human antibody and all, or substantially all, of the framework regions correspond to those of a relevant human consensus sequence. Humanized antibodies optimally also include at least a portion of an antibody constant region, such as an Fc region, typically derived from a human antibody (see, for example, Jones et al., 1986. Nature 321:522-525; Riechmann et al., 1988. Nature 332:323-329; and Presta, 1992. Curr. Op. Struct. Biol. 2:593-596).

Methods for humanizing non human antibodies are well known in the art. Generally, a humanized antibody has one or more amino acid residues introduced into it from a source which is non human. These non human amino acid residues are often referred to as imported residues which are typically taken from an imported variable domain. Humanization can be essentially performed as described (see, for example: Jones et al., 1986. Nature 321:522-525; Riechmann et al., 1988. Nature 332:323-327; Verhoeyen et al., 1988. Science 239:1534-1536; U.S. Pat. No. 4,816,567) by substituting human complementarity determining regions with corresponding rodent complementarity determining regions. Accordingly, such humanized antibodies are chimeric antibodies, wherein substantially less than an intact human variable domain has been substituted by the corresponding sequence from a non human species. In practice, humanized antibodies may be typically human antibodies in which some complementarity determining region residues and possibly some framework residues are substituted by residues from analogous sites in rodent antibodies.

Human antibodies can also be produced using various techniques known in the art, including phage display libraries [see, for example, Hoogenboom and Winter, 1991. J. Mol. Biol. 227:381; Marks et al., 1991. J. Mol. Biol. 222:581; Cole et al., "Monoclonal Antibodies and Cancer Therapy", Alan R. Liss, pp. 77 (1985); Boerner et al., 1991. J. Immunol. 147: 86-95). Humanized antibodies can also be made by introducing sequences encoding human immunoglobulin loci into transgenic animals, e.g., into mice in which the endogenous immunoglobulin genes have been partially or completely inactivated. Upon antigenic challenge, human antibody production is observed in such animals which closely resembles that seen in humans in all respects, including gene rearrangement, chain assembly, and antibody repertoire. Ample guidance for practicing such an approach is provided in the literature of the art (for example, refer to: U.S. Pat. Nos. 5,545,807, 5,545,806, 5,569,825, 5,625,126, 5,633,425, and 5,661,016; Marks et al., 1992. Bio/Technology 10:779-783; Lonberg et al., 1994. Nature 368:856-859; Morrison, 1994. Nature 368: 812-13; Fishwild et al., 1996. Nature Biotechnology 14:845-51; Neuberger, 1996. Nature Biotechnology 14:826; Lonberg and Huszar, 1995. Intern. Rev. Immunol. 13:65-93).

Once antibodies are obtained, they may be tested for binding capacity, for example via ELISA, so as to determine suitable functional concentrations.

For treating a disease associated with a pathological cell population such as a tumoral disease, increasing the association of complement with the pathological tumor cell population so as to therapeutically increase complement-mediated cytolysis thereof may be optimally effected by administering to the subject a siRNA molecule specific to mortalin concomitantly to an antibody capable of specifically binding an antigen which is specifically displayed by the tumor cell population. In the case of a malignant tumor, such antigens are commonly referred to as tumor-associated antigens, and characterization and identification of such antigens is routinely practiced in the art, for example during diagnosis and staging of the disease. Antibodies specific for such antigens which may be used to treat a disease of the present invention along with the mortalin-specific siRNA molecules include, for example, Rituxan (rituximab) commonly used for treatment of relapsed or refractory CD20-positive non-Hodgkin's B-cell lymphoma; and Herceptin (trastuzumab) commonly employed for treatment of mammary tumors overexpressing the human epidermal growth factor receptor 2 (HER-2).

While various tumor specific antibodies have been developed for cancer therapy, their in-vivo efficiency in complement activation is poor, and, as such, the present invention, which utilizes mortalin-specific siRNA molecules in combination with antibodies (e.g. anti-CD20 mAb such as Rituximab/Mabthera or tumor specific antibodies), can be used to enhance complement-mediated cytolysis of tumors cells induced by such antibodies, thereby significantly improving cancer treatment.

For treating a disease associated with a pathological cell population such as an intracellular pathogen infection, increasing the association of complement with the pathological infected cell population so as to therapeutically increase complement-mediated cytolysis thereof may be optimally effected by concomitantly administering to the subject a siRNA molecule specific to mortalin and an antibody capable of specifically binding an antigen of the pathogen displayed on the surface of the infected cell population. Such antigens include those which are displayed complexed with an MHC molecule. Antibodies specific for such MHC-antigen complexes are well known in the art.

For treating a disease associated with a pathological cell population such as an autoimmune disease mediated by pathogenic autoantigen specific T-cells or B-cells/antibodies, increasing the association of complement with the pathological lymphocyte population so as to therapeutically increase complement-mediated cytolysis thereof may be optimally effected by concurrently administering to the subject a siRNA molecule specific to mortalin and an antibody capable of specifically binding an autoantigen-specific T-cell or B-cell antigen receptor of the pathological T-lymphocyte or B-lymphocyte population, respectively.

Similarly, for treating transplantation-related diseases, siRNA molecules specific to mortalin can be used together with antibodies specific for T- or B-cell receptors to increase complement-mediated cytotoxicity of pathological T- or B-cells, respectively, so as to therapeutically increase complement-mediated cytolysis of such pathological lymphocytes. For example, such treatment of allograft rejection may be achieved using the siRNAs encoded by SEQ ID NO: 173 to 344 along with antibodies specific for T-cell receptors of the pathological allograft-reactive T-cell population. Moreover, such treatment of xenograft rejection may be achieved using siRNA molecules specific to mortalin along with antibodies specific for B-cell receptors of the pathological xenograft-reactive B-cell population. Furthermore, such treatment of graft-versus-host disease (GVHD) may be achieved using siRNA molecules specific to mortalin along with antibodies specific for T- or B-cell receptors, as suitable, of the pathological host-reactive T- or B-cell population.

Antibodies specific for T-cell or B-cell receptors, commonly termed "anti-idiotype" antibodies, are well known and routinely employed in the art.

It will be appreciated that antibodies specific for any one of various antigens other than lymphocyte receptors, which are specifically displayed at the surface of pathogenic lymphocyte populations in subjects having a transplantation-related disease may also be used (concomitantly with siRNA molecules specific to mortalin) to induce cytolysis of such lymphocyte populations so as to achieve disease treatment according to the teachings of the present invention. Such antigens may be, for example allelic variants specifically expressed in the graft recipient but not in the graft, or vice-versa.

A siRNA molecule used for down-regulating the level of the mortalin polypeptide in the pathological cell population of the present invention, can be suitably formulated as a pharmaceutical composition.

Furthermore, according to another aspect of the present invention there is provided an article of manufacture which comprises a siRNA molecule selected from the group consisting of SEQ ID NO: 173 to 344 and an antibody capable of specifically binding a pathological cell population.

Ample guidance regarding suitable formulation of pharmaceutical compositions and their packaging as articles of manufacture is provided hereinbelow.

One of ordinary skill in the art, such as a physician, preferably a physician specialized in the disease to be treated, will possess the necessary expertise for adapting the teachings of the present invention for suitably treating a disease of the present invention in a given subject. In particular, one of ordinary skill in the art will possess the necessary expertise for selecting a suitable administration route for administering a therapeutic compound of the present invention, will possess the necessary expertise for selecting a suitable dosage and frequency of administration for administering a therapeutic compound of the present invention, and will possess the necessary expertise for suitably monitoring the disease so as to achieve a desired therapeutic outcome.

Suitable routes of administration of a therapeutic compound of the present invention are described hereinbelow.

A siRNA of the present invention may be suitably administered over any one of various durations; and may be suitably administered continuously, or discontinuously in order to achieve disease treatment.

Examples of types and specific examples of diseases treatable according to the method of the present invention are listed hereinbelow.

Types of tumoral diseases amenable to treatment via the method of the present invention include benign tumors, warts, polyps, precancers, and malignant tumors/cancer.

Specific examples of tumoral diseases which can be treated using the siRNAs of the present invention include, but are not limited to, adrenocortical carcinoma, hereditary; bladder cancer; breast cancer; breast cancer, ductal; breast cancer, invasive intraductal; breast cancer, sporadic; breast cancer, susceptibility to; breast cancer, type 4; breast cancer, type 4; breast cancer-1; breast cancer-3; breast-ovarian cancer; Burkitt's lymphoma; cervical carcinoma; colorectal adenoma; colorectal cancer; colorectal cancer, hereditary nonpolyposis, type 1; colorectal cancer, hereditary nonpolyposis, type 2; colorectal cancer, hereditary nonpolyposis, type 3; colorectal cancer, hereditary nonpolyposis, type 6; colorectal cancer, hereditary nonpolyposis, type 7; dermatofibrosarcoma protuberans; endometrial carcinoma; esophageal cancer; gastric cancer, fibrosarcoma, glioblastoma multiforme; glomus tumors, multiple; hepatoblastoma; hepatocellular cancer; hepatocellular carcinoma; leukemia, acute lymphoblastic; leukemia, acute myeloid; leukemia, acute myeloid, with eosinophilia; leukemia, acute nonlymphocytic; leukemia, chronic myeloid; Li-Fraumeni syndrome; liposarcoma, lung cancer; lung cancer, small cell; lymphoma, non-Hodgkin's; lynch cancer family syndrome II; male germ cell tumor; mast cell leukemia; medullary thyroid; medulloblastoma; melanoma, meningioma; multiple endocrine neoplasia; myeloid malignancy, predisposition to; myxosarcoma; neuroblastoma; osteosarcoma; ovarian cancer; ovarian cancer, serous; ovarian carcinoma; ovarian sex cord tumors; pancreatic cancer; pancreatic endocrine tumors; paraganglioma, familial nonchromaffin; pilomatricoma; pituitary tumor, invasive; prostate adenocarcinoma; prostate cancer; renal cell carcinoma, papillary, familial and sporadic; retinoblastoma; rhabdoid predisposition syndrome, familial; rhabdoid tumors; rhabdomyosarcoma; small-cell cancer of lung; soft tissue sarcoma, squamous cell carcinoma, head and neck; T-cell acute lymphoblastic leukemia; Turcot syndrome with glioblastoma; tylosis with esophageal cancer; uterine cervix carcinoma, Wilms' tumor, type 2; and Wilms' tumor, type 1, and the like.

Precancers are well characterized and known in the art (refer, for example, to Berman J J. and Henson D E., 2003. Classifying the precancers: a metadata approach. BMC Med Inform Decis Mak. 3:8). Classes of precancers amenable to treatment via the method of the present invention include acquired small or microscopic precancers, acquired large lesions with nuclear atypia, precursor lesions occurring with inherited hyperplastic syndromes that progress to cancer, and acquired diffuse hyperplasias and diffuse metaplasias. Examples of small or microscopic precancers include HGSIL (High grade squamous intraepithelial lesion of uterine cervix), AIN (anal intraepithelial neoplasia), dysplasia of vocal cord, aberrant crypts (of colon), PIN (prostatic intraepithelial neoplasia). Examples of acquired large lesions with nuclear atypia include tubular adenoma, AILD (angioimmunoblastic lymphadenopathy with dysproteinemia), atypical meningioma, gastric polyp, large plaque parapsoriasis, myelodysplasia, papillary transitional cell carcinoma in-situ, refractory anemia with excess blasts, and Schneiderian papilloma. Examples of precursor lesions occurring with inherited hyperplastic syndromes that progress to cancer include atypical mole syndrome, C cell adenomatosis and MEA. Examples of acquired diffuse hyperplasias and diffuse metaplasias include AIDS, atypical lymphoid hyperplasia, Paget's disease of bone, post-transplant lymphoproliferative disease and ulcerative colitis.

Preferably, the tumoral disease is a malignant primary or metastatic tumor, more preferably a malignant hematopoietic malignancy, more preferably a leukemia or lymphoma, and most preferably an erythroleukemia, a chronic myeloid leukemia, T cell lymphoma or B cell lymphoma. As is described and illustrated in the Examples section which follows, the method of the present invention can be used to increase complement-mediated cytolysis of human erythroleukemia cells (refer, for example, to FIGS. 1-2).

Specific examples of intracellular pathogens infections which may be treated according to the teachings of the present invention include, but are not limited to, infections by viral pathogens, intracellular mycobacterial pathogens (such as, for example, *Mycobacterium tuberculosis*), intracellular bacterial pathogens (such as, for example, *Listeria monocytogenes*), or intracellular protozoan pathogens (such as, for example, *Leishmania* and *Trypanosoma*).

Specific types of viral pathogens causing infectious diseases treatable according to the teachings of the present invention include, but are not limited to, retroviruses, circoviruses, parvoviruses, papovaviruses, adenoviruses, herpesviruses, iridoviruses, poxviruses, hepadnaviruses, picornaviruses, caliciviruses, togaviruses, flaviviruses, reoviruses, orthomyxoviruses, paramyxoviruses, rhabdoviruses, bunyaviruses, coronaviruses, arenaviruses, and filoviruses.

Specific examples of viral infections which may be treated according to the teachings of the present invention include, but are not limited to, human immunodeficiency virus (HIV)-induced acquired immunodeficiency syndrome (AIDS), influenza, rhinoviral infection, viral meningitis, Epstein-Barr virus (EBV) infection, hepatitis A, B or C virus infection, measles, papilloma virus infection/warts, cytomegalovirus (CMV) infection, Herpes simplex virus infection, yellow fever, Ebola virus infection, rabies, etc.

Specific examples of transplantation-related diseases which may be treated according to the teachings of the present invention include but are not limited to graft rejection, chronic graft rejection, subacute graft rejection, hyperacute graft rejection, acute graft rejection, allograft rejection, xenograft rejection and graft-versus-host disease (GVHD).

Specific examples of antibody-mediated autoimmune diseases which may be treated according to the teachings of the present invention include, but are not limited to, rheumatoid diseases, rheumatoid autoimmune diseases, rheumatoid arthritis (Krenn V. et al., Histol Histopathol 2000 July; 15 (3):791), spondylitis, ankylosing spondylitis (Jan Voswinkel et al., Arthritis Res 2001; 3 (3): 189), systemic diseases, systemic autoimmune diseases, systemic lupus erythematosus (Erikson J. et al., Immunol Res 1998; 17 (1-2):49), sclerosis, systemic sclerosis (Renaudineau Y. et al., Clin Diagn Lab Immunol. 1999 March; 6 (2):156); Chan O T. et al., Immunol Rev 1999 June; 169:107), glandular diseases, glandular autoimmune diseases, pancreatic autoimmune diseases, diabetes, Type I diabetes (Zimmet P. Diabetes Res Clin Pract 1996 October; 34 Suppl:S125), thyroid diseases, autoimmune thyroid diseases, Graves' disease (Orgiazzi J. Endocrinol Metab Clin North Am 2000 June; 29 (2):339), thyroiditis, spontaneous autoimmune thyroiditis (Braley-Mullen H. and Yu S, J Immunol 2000 Dec. 15; 165 (12):7262), Hashimoto's thyroiditis (Toyoda N. et al., Nippon Rinsho 1999 August; 57 (8):1810), myxedema, idiopathic myxedema (Mitsuma T. Nippon Rinsho. 1999 August; 57 (8):1759); autoimmune reproductive diseases, ovarian diseases, ovarian autoimmunity (Garza K M. et al., J Reprod Immunol 1998 February; 37 (2):87), autoimmune anti-sperm infertility (Diekman A B. et al., Am J Reprod Immunol. 2000 March; 43 (3):134), repeated fetal loss (Tincani A. et al., Lupus 1998; 7 Suppl 2:S107-9), neurodegenerative diseases, neurological diseases, neurological autoimmune diseases, multiple sclerosis (Cross A H. et al., J Neuroimmunol 2001 Jan. 1; 112 (1-2):1), Alzheimer's disease (Oron L. et al., J Neural Transm Suppl. 1997; 49:77), myasthenia gravis (Infante A J. And Kraig E, Int Rev Immunol 1999; 18 (1-2):83), motor neuropathies (Kornberg A J. J Clin Neurosci. 2000 May; 7 (3):191), Guillain-Barre syndrome, neuropathies and autoimmune neuropathies (Kusunoki S. Am J Med Sci. 2000 April; 319 (4):234), myasthenic diseases, Lambert-Eaton myasthenic syndrome (Takamori M. Am J Med Sci. 2000 April; 319 (4):204), paraneoplastic neurological diseases, cerebellar atrophy, paraneoplastic cerebellar atrophy, non-paraneoplastic stiff man syndrome, cerebellar atrophies, progressive cerebellar atrophies, encephalitis, Rasmussen's encephalitis, amyotrophic lateral sclerosis, Sydeham chorea, Gilles de la Tourette syndrome, polyendocrinopathies, autoimmune polyendocrinopathies (Antoine J C. and Honnorat J. Rev Neurol (Paris) 2000 January; 156 (1):23); neuropathies, dysimmune neuropathies (Nobile-Orazio E. et al., Electroencephalogr Clin Neurophysiol Suppl 1999; 50:419); neuromyotonia, acquired neuromyotonia, arthrogryposis multiplex congenita (Vincent A. et al., Ann NY Acad Sci. 1998 May 13; 841:482), cardiovascular diseases, cardiovascular autoimmune diseases, atherosclerosis (Matsuura E. et al., Lupus. 1998; 7 Suppl 2:S135), myocardial infarction (Vaarala O. Lupus. 1998; 7 Suppl 2:S132), thrombosis (Tincani A. et al., Lupus 1998; 7 Suppl 2:S107-9), granulomatosis, Wegener's granulomatosis, arteritis, Takayasu's arteritis and Kawasaki syndrome (Praprotnik S. et al., Wien Klin Wochenschr 2000 Aug. 25; 112 (15-16):660); anti-factor VIII autoimmune disease (Lacroix-Desmazes S. et al., Semin Thromb Hemost. 2000; 26 (2):157); vasculitises, necrotizing small vessel vasculitises, microscopic polyangiitis, Churg and Strauss syndrome, glomerulonephritis, pauci-immune focal necrotizing glomerulonephritis, crescentic glomerulonephritis (Noel L H. Ann Med Interne (Paris). 2000 May; 151 (3):178); antiphospholipid syndrome (Flamholz R. et al., J Clin Apheresis 1999; 14 (4):171); heart failure, agonist-like beta-adrenoceptor antibodies in heart failure (Wallukat G. et al., Am J Cardiol. 1999 Jun. 17; 83 (12A):75H), thrombocytopenic purpura (Moccia F. Ann Ital Med Int. 1999 April-June; 14 (2):114); hemolytic anemia, autoimmune hemolytic anemia (Efremov D G. et al., Leuk Lymphoma 1998 January; 28 (3-4):285), gastrointestinal diseases, autoimmune diseases of the gastrointestinal tract, intestinal diseases, chronic inflammatory intestinal disease (Garcia Herola A. et al., Gastroenterol Hepatol. 2000 January; 23 (1):16), celiac disease (Landau YE. and Shoenfeld Y. Harefuah 2000 Jan. 16; 138 (2):122), autoimmune diseases of the musculature, myositis, autoimmune myositis, Sjogren's syndrome (Feist E. et al., Int Arch Allergy Immunol 2000 September; 123 (1):92); smooth muscle autoimmune disease (Zauli D. et al., Biomed Pharmacother 1999 June; 53 (5-6):234), hepatic diseases, hepatic autoimmune diseases, autoimmune hepatitis (Manns M P. J Hepatol 2000 August; 33 (2):326) and primary biliary cirrhosis (Strassburg C P. et al., Eur J Gastroenterol Hepatol. 1999 June; 11 (6):595).

As described hereinabove, the present invention provides articles of manufacture and pharmaceutical compositions comprising the siRNAs of the present invention.

As used herein a "pharmaceutical composition" refers to a preparation of one or more of the active ingredients described herein with other chemical components such as physiologically suitable carriers and excipients. The purpose of the pharmaceutical composition is to facilitate administration of the active ingredients to the subject.

Hereinafter, the phrases "physiologically acceptable carrier" and "pharmaceutically acceptable carrier" which may be interchangeably used refer to a carrier or a diluent that does not cause significant irritation to the subject and does not abrogate the biological activity and properties of the administered active ingredients. An adjuvant is included under these phrases.

Herein, the term "excipient" refers to an inert substance added to the pharmaceutical composition to further facilitate administration of an active ingredient of the present invention. Examples, without limitation, of excipients include calcium carbonate, calcium phosphate, various sugars and types of starch, cellulose derivatives, gelatin, vegetable oils and polyethylene glycols. The pharmaceutical composition may advantageously take the form of a foam or a gel.

Techniques for formulation and administration of drugs may be found in "Remington's Pharmaceutical Sciences," Mack Publishing Co., Easton, Pa., latest edition, which is incorporated herein by reference.

Suitable routes of administration include any of various suitable systemic and/or local routes of administration.

Suitable routes of administration may, for example, include the inhalation, oral, buccal, rectal, transmucosal, topical, transdermal, intradermal, transnasal, intestinal and/or parenteral routes; the intramuscular, subcutaneous and/or intramedullary injection routes; the intrathecal, direct intraventricular, intravenous, intraperitoneal, intranasal, and/or intraocular injection routes; and/or the route of direct injection into a tissue region of the subject.

The pharmaceutical composition may be manufactured by processes well known in the art, e.g., by means of conventional mixing, dissolving, granulating, dragee-making, levigating, emulsifying, encapsulating, entrapping or lyophilizing processes.

Pharmaceutical compositions for use in accordance with the present invention thus may be formulated in conventional manner using one or more physiologically acceptable carriers comprising excipients and auxiliaries, which facilitate processing of the active ingredients into preparations which, can be used pharmaceutically. Proper formulation is dependent upon the route of administration chosen.

For injection, the active ingredients of the pharmaceutical composition may be formulated in aqueous solutions, preferably in physiologically compatible buffers such as Hank's solution, Ringer's solution, or physiological salt buffer.

For transmucosal administration, penetrants appropriate to the barrier to be permeated are used in the formulation. Such penetrants are generally known in the art.

For oral administration, the pharmaceutical composition can be formulated readily by combining the active ingredients with pharmaceutically acceptable carriers well known in the art. Such carriers enable the pharmaceutical composition to be formulated as tablets, pills, dragees, capsules, liquids, gels, syrups, slurries, suspensions, and the like, for oral ingestion by a patient. Pharmacological preparations for oral use can be made using a solid excipient, optionally grinding the resulting mixture, and processing the mixture of granules, after adding suitable auxiliaries if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carbomethylcellulose; and/or physiologically acceptable polymers such as polyvinylpyrrolidone (PVP). If desired, disintegrating agents may be added, such as cross-linked polyvinyl pyrrolidone, agar, or alginic acid or a salt thereof such as sodium alginate.

Dragee cores are provided with suitable coatings. For this purpose, concentrated sugar solutions may be used which may optionally contain gum arabic, talc, polyvinyl pyrrolidone, carbopol gel, polyethylene glycol, titanium dioxide, lacquer solutions and suitable organic solvents or solvent mixtures. Dyestuffs or pigments may be added to the tablets or dragee coatings for identification or to characterize different combinations of active ingredient doses.

Pharmaceutical compositions which can be used orally, include push-fit capsules made of gelatin as well as soft, sealed capsules made of gelatin and a plasticizer, such as glycerol or sorbitol. The push-fit capsules may contain the active ingredients in admixture with filler such as lactose, binders such as starches, lubricants such as talc or magnesium stearate and, optionally, stabilizers. In soft capsules, the active ingredients may be dissolved or suspended in suitable liquids, such as fatty oils, liquid paraffin, or liquid polyethylene glycols. In addition, stabilizers may be added. All formulations for oral administration should be in dosages suitable for the chosen route of administration.

For buccal administration, the compositions may take the form of tablets or lozenges formulated in conventional manner.

For administration via the inhalation route, the active ingredients for use according to the present invention can be delivered in the form of an aerosol/spray presentation from a pressurized pack or a nebulizer with the use of a suitable propellant, e.g., a fluorochlorohydrocarbon such as dichlorodifluoromethane, trichlorofluoromethane, dichlorotetrafluoroethane; carbon dioxide; or a volatile hydrocarbon such as butane, propane, isobutane, or mixtures thereof. In the case of a pressurized aerosol, the dosage unit may be determined by providing a valve to deliver a metered amount. Capsules and cartridges of, e.g., gelatin for use in a dispenser may be formulated containing a powder mix of the active ingredients and a suitable powder base such as lactose or starch.

The pharmaceutical composition may be formulated for parenteral administration, e.g., by bolus injection or continuous infusion. Formulations for injection may be presented in unit dosage form, e.g., in ampoules or in multidose containers with optionally, an added preservative. The compositions may be suspensions, solutions or emulsions in oily or aqueous vehicles, and may contain formulatory agents such as suspending, stabilizing and/or dispersing agents.

A pharmaceutical composition for parenteral administration may include an aqueous solution of the active ingredients in water-soluble form. Additionally, suspensions of the active ingredients may be prepared as appropriate oily or water based injection suspensions. Suitable lipophilic solvents or vehicles include fatty oils such as sesame oil, or synthetic fatty acids esters such as ethyl oleate, triglycerides or liposomes. Aqueous injection suspensions may contain substances, which increase the viscosity of the suspension, such as sodium carboxymethyl cellulose, sorbitol or dextran. Optionally, the suspension may also contain suitable stabilizers or agents which increase the solubility of the active ingredients to allow for the preparation of highly concentrated solutions.

Alternatively, the active ingredients may be in powder form for constitution with a suitable vehicle, e.g., sterile, pyrogen-free water based solution, before use.

The pharmaceutical composition may also be formulated in rectal compositions such as suppositories or retention enemas, using, e.g., conventional suppository bases such as cocoa butter or other glycerides.

The pharmaceutical composition should contain the active ingredients in an amount effective to achieve disease treatment.

Determination of a therapeutically effective amount is well within the capability of those skilled in the art, especially in light of the detailed disclosure provided herein.

For any preparation used in the methods of the invention, the therapeutically effective amount or dose can be estimated initially from in vitro and cell culture assays. For example, a dose can be formulated in animal models to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patients condition. (See e.g., Fingl, et al., 1975, in "The Pharmacological Basis of Therapeutics", Ch. 1 p. 1).

Dosage amount and interval may be adjusted individually to provide plasma or brain levels of the active ingredients which are sufficient to achieve the desired therapeutic effect (minimal effective concentration, MEC). The MEC will vary for each preparation, but can be estimated from in vitro data. Dosages necessary to achieve the MEC will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or until cure is effected or diminution of the disease state is achieved.

The amount of the composition to be administered will be dependent on the subject being treated, the severity of the affliction, the manner of administration, the judgment of the prescribing physician, etc.

Compositions of the present invention may, if desired, be presented in a pack or dispenser device, such as an FDA approved kit, which may contain one or more unit dosage forms containing the active ingredients. The pack may, for example, comprise metal or plastic foil, such as a blister pack. The pack or dispenser device may be accompanied by instructions for administration. The pack or dispenser may also be accommodated by a notice associated with the container in a form prescribed by a governmental agency regulating the manufacture, use or sale of pharmaceuticals, which notice is reflective of approval by the agency of the form of the compositions or human or veterinary administration. Such notice, for example, may be of labeling approved by the U.S. Food and Drug Administration for prescription drugs or of an approved product insert.

Thus, the present invention provides optimal methods of, pharmaceutical compositions for, and articles of manufacture for treating, via the use of mortalin-specific siRNA, diseases associated with pathological cells and treatable via complement-mediated cytolysis of such pathological cells and/or associated with pathological complement-mediated cytotoxicity, such as tumoral, infectious, transplantation-related and autoimmune-mediated diseases.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below.

Example 1

Mortalin Specific siRNA Effectively Suppresses Mortalin Expression in-vivo

Materials and Methods:

Tumor induction: Tumor induction was carried out by injection of K562 human chronic myeloid leukemia cells ($6 \times 10^6$ cells) subcutaneously into athymic Nude mice in 100 □l PBS. After 2 weeks, tumor size reached an average diameter of 1 cm.

Effect of mortalin specific siRNA on mortalin expression: Analysis of siRNA on silencing of mortalin was established by intratumorally injecting 3 groups of 3 tumor comprising mice. One group was intratumorally injected with 15 nmol of mortalin specific siRNA1 (SEQ ID NO: 192), one group was intratumorally injected with a non-specific scramble siRNA (SEQ ID NO: 345, Dharmacon, siStable) and a third group served as negative control and was not injected with siRNA. Two days later, the tumor masses were excised and immediately put on ice with lysis buffer containing protease inhibitors. The tumors were chopped into small pieces and extracted. Following determination of protein concentration, equal amounts of protein were mixed with sample buffer, heated for 5 minutes at 95° C. and separated on SDS-PAGE gels. The proteins were blotted onto Nitrocellulose membrane and analyzed with anti-mortalin antibodies (Santa Cruz Biotechnology, Santa Cruz, Calif. and rabbit anti-mortalin antibodies prepared by inventors) and with anti-actin antibodies (R&D Systems, Minneapolis, Minn.). The membranes were developed with an ECL kit (Amersham) and the mortalin and actin bands were analyzed by densitometry. The density of the mortalin bands was corrected according to the density of the actin bands.

Results:

As evident in FIG. 1, two days following in vivo intratumoral injection of mortalin specific siRNA, a major reduction in mortalin expression level was recorded. This reduction in mortalin expression level was specific to mortalin-specific siRNA and was not observed in mice treated with control siRNA. Thus, in vivo treatment of cancer with siRNA specific to mortalin silenced mortalin expression.

Example 2

Mortalin Specific siRNA Effectively Suppresses Tumor Growth in-vivo

Materials and Methods:

Tumor induction: Tumor induction was carried out by injection of K562 human chronic myeloid leukemia (6×10⁶ cells) subcutaneously into athymic Nude mice in 100 µl PBS. After 2 weeks, tumor size reached an average diameter of 1 cm.

Effect of mortalin specific siRNA on tumor growth: Analysis of mortalin specific siRNA on tumor growth was established by intratumorally injecting 3 groups of 8 tumor comprising mice. One group was intratumorally injected with 30 nmol mortalin specific siRNA1 (SEQ ID NO: 192), one group was intratumorally injected with control siRNA (SEQ ID NO: 345, Dharmacon, siStable) and a third group served as negative control and was not injected with siRNA. The size of the tumor was monitored by Caliper measurements. Since most tumors grew in ellipsoids and not in circles, the long and short diameters were measured and multiplied.

Figure 2:
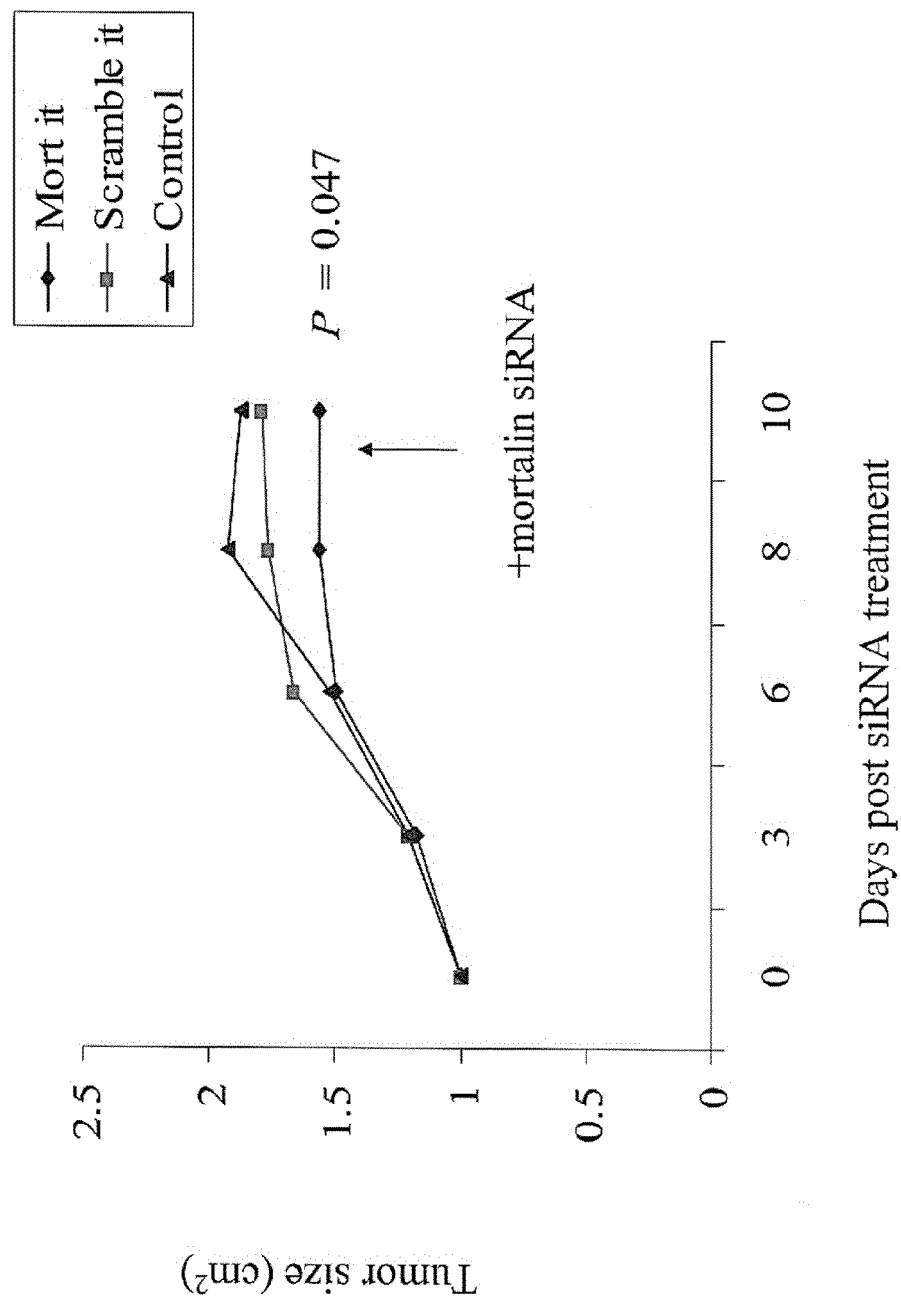
FIG. 2 is a line graph depicting in vivo reduction in tumor growth following intratumoral injection of mortalin specific siRNA. The results show K562 tumor size (in $cm^2$) in mice injected once (on day 0) intratumorally with 15 nmol mortalin specific siRNA1 (SEQ ID NO: 192, depicted by diamonds), control siRNA (SEQ ID NO: 345, depicted by pink squares), or control non-injected (depicted by triangles). Tumor size was analyzed by t-test and was found to be significant on Day 10 ($P<0.047$). Of note, the results indicate a major difference in tumor size in mice treated by mortalin-specific siRNA and mice treated by control siRNA.

Results:

In vivo, intratumoral injections of mortalin specific siRNA lead to a significant decreases in tumor size on Day 10 (FIG. 2). A major difference in tumor size was recorded in mice treated by mortalin specific siRNA compared to mice treated by control siRNA. Thus, in vivo treatment of cancer with siRNA specific to mortalin efficiently reduced tumor size.

Example 3

Mortalin Specific siRNA Enhances Sensitivity of EL4 Cells to Lysis by Complement Materials and Methods:

Cell transfection: EL4 T-lymphoma cells were transfected with siRNA directed to mouse mortalin (mot-2, SEQ ID NO: 348; Dharmacon, siStable) mRNA in the presence of Lipofectamine (Invitrogen) according to manufacturer's instructions and were cultured for 48 hours. Cells transfected with non-specific siRNA (NS, SEQ ID NO: 350; Dharmacon, siStable) served as control.

Cytotoxicity assay: Cytotoxicity assays were carried out in which the EL4 transformed cells were treated with normal human serum (NHS), as a source of complement, or with heat-inactivated normal human serum (HI-NHS) as negative control. After 60 minutes at 37° C., percent cell death was determined by Trypan blue inclusion.

Figure 3:
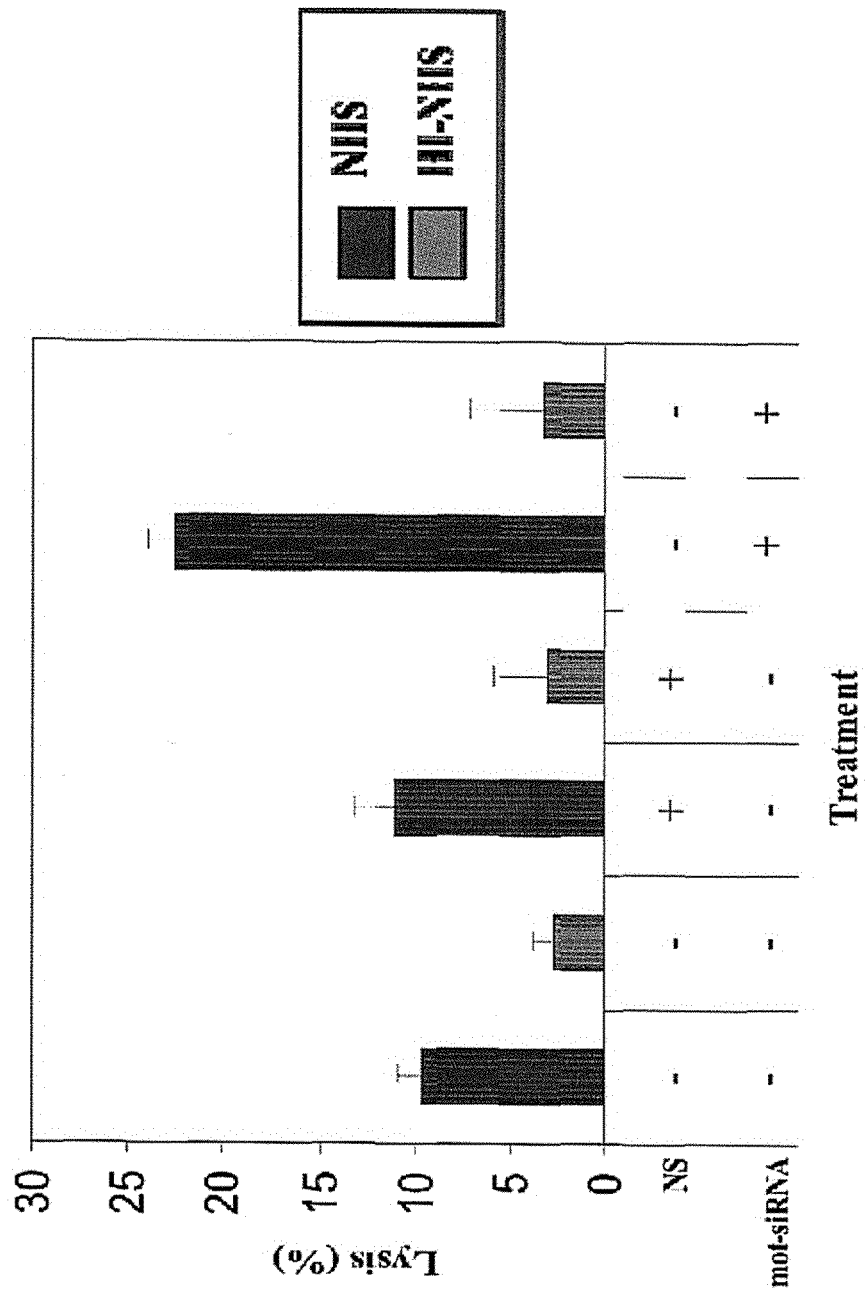
FIG. 3 is a bar graph depicting enhanced sensitivity to lysis by complement in EL4 T lymphoma cells transfected with mortalin specific siRNA. The results show EL4 cells transfected with mortalin specific siRNA (mot-siRNA, SEQ ID NO: 348) or with non specific siRNA (NS, SEQ ID NO: 350). Cytotoxicity assay was carried out with normal human serum (NHS) as source of complement or with heat inactivated human serum (HI-NHS) in which the complement is inactivated.

Results:

Treatment with mortalin specific siRNA reduced the level of mortalin in EL4 cells to 30% of control levels as determined by Western blotting (results not shown). Cytotoxicity assays of these cells with normal human serum (NHS), as a source of complement, or with heat-inactivated normal human serum (HI-NHS) showed that treatment with siRNA significantly enhanced the sensitivity of EL4 cells to lysis by complement. (*, P<0.05, FIG. 3).

Example 4

Transfection with Mortalin Specific siRNA Reduces EL4 Tumor Growth in Mice

Cell transfection: EL4 T-lymphoma cells were transfected with siRNA directed to mouse mortalin (mortalin siRNA, SEQ ID NO: 348; Dharmacon, siStable) mRNA in the presence of Lipofectamine (Invitrogen) according to manufacturer's instructions and were cultured for 48 hours. Cells transfected with non-specific siRNA (scrambled siRNA, SEQ ID NO: 350; Dharmacon, siStable) served as control.

In vivo induction of tumor growth: Mortalin specific siRNA- or scramble siRNA-transfected EL4 cells were injected subcutaneously into two groups of C57Bl/6 mice (1×10³ cells/mouse, 3 mice per group). Tumor size was measured by a Caliper over a period of 27 days before the experiment was terminated.

Figure 4:
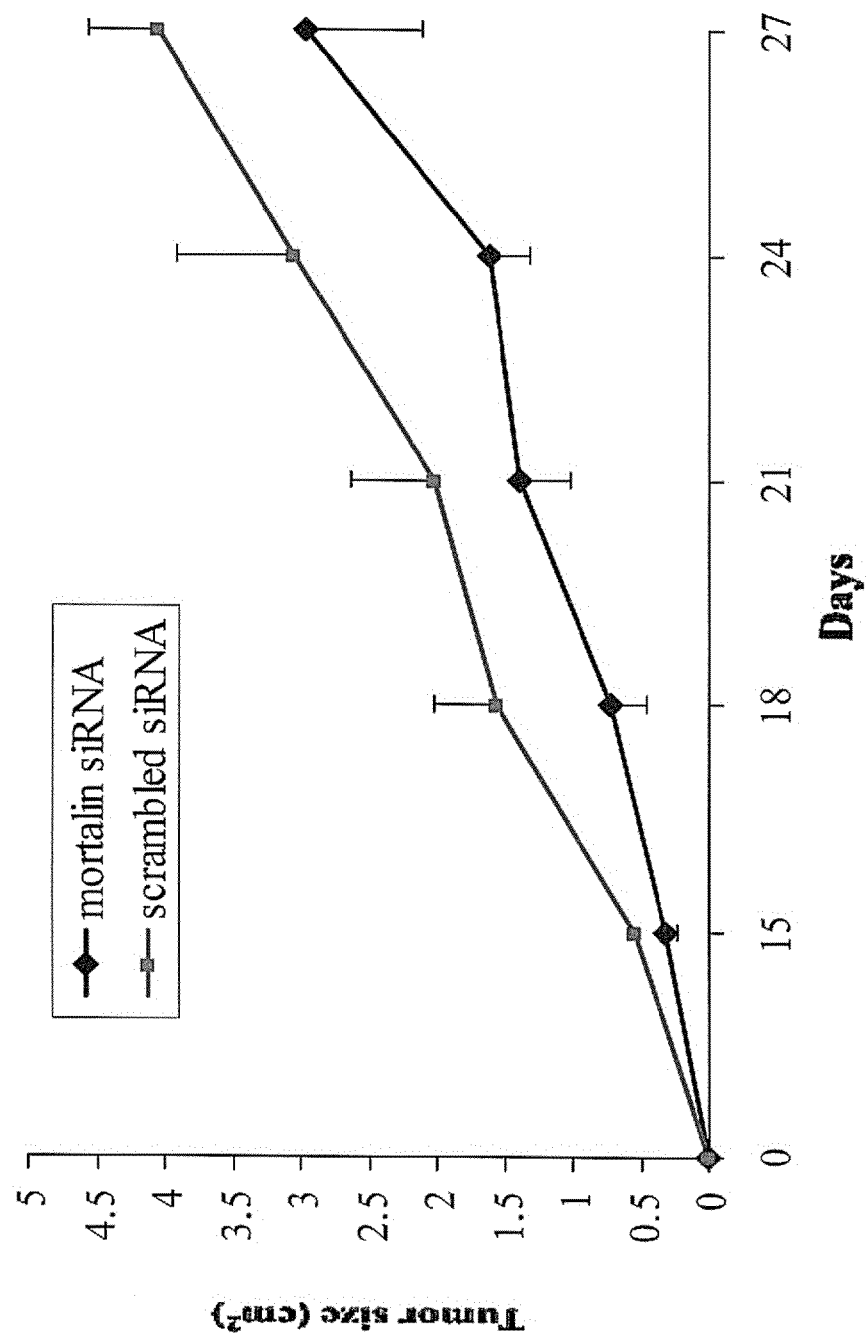
FIG. 4 is a line graph depicting reduced in vivo tumor growth in EL4 T lymphoma cells transfected with mortalin specific siRNA. The results show EL4 cells transfected with mouse specific mortalin siRNA (siRNA mortalin, SEQ ID NO: 348) or with non-specific scrambled siRNA (scrambled siRNA, SEQ ID NO: 350). Cells were injected subcutaneously into two groups of C57Bl/6 mice ($1\times10^3$ cells/mouse, 3 mice per group). Tumor size was measured by a Caliper over a period of 27 days.

Results:

As is evident in FIG. 4, injection of mortalin specific siRNA transfected EL4 cells into C57B1/6 mice reduced the subcutaneous growth of EL4 cells compared to scramble siRNA transfected cells (*, P<0.05).

Example 5

Transfection with Mortalin Specific siRNA Reduces EL4 Cell Growth Within the Blood Circulation of Effected Mice Materials and Methods:

Cell transfection: As depicted in detail in Example 4, hereinabove.

Intravenous injection of EL4 cells into mice and measurement of EL4 cell levels: Mortalin specific siRNA (SEQ ID NO: 348) or scramble siRNA (SEQ ID NO: 350) transfected EL4 cells were injected intravenously into three groups of C57Bl/6 mice (5×10⁴ cells/mouse, 3 mice per group). After two weeks, the experiment was terminated, peripheral blood was collected and centrifuged at 2000 rpm for 10 minutes. Pellet of cells containing mixed red (RBC) and white (WBC) blood cells was treated with RBC lysis buffer. The WBCs, containing the EL4 cells, were counted in Hemacytometer in the presence of Trypan blue.

Figure 5:
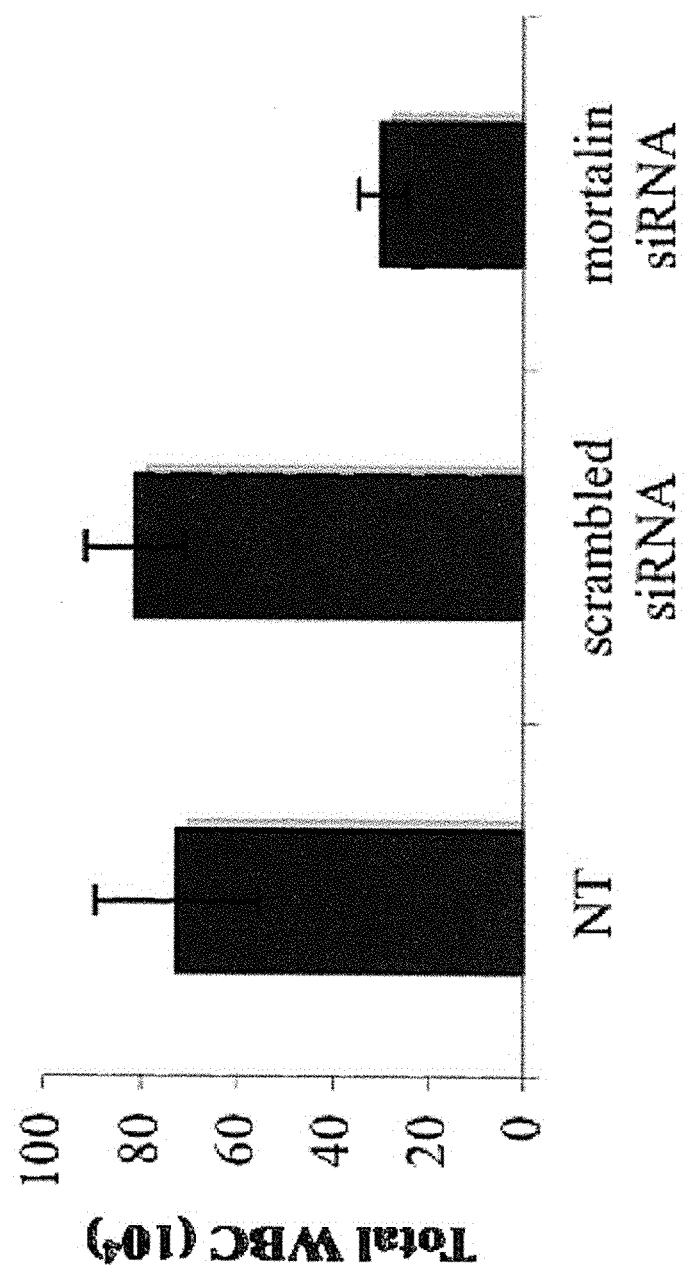
FIG. 5 is a bar graph depicting reduced growth of EL4 cells transfected with mortalin specific siRNA within the blood circulation of effected mice. The results show EL4 cells transfected with mouse specific mortalin siRNA (siRNA mortalin, SEQ ID NO: 348) or with non-specific scrambled siRNA (scrambled siRNA, SEQ ID NO: 350). Cells were injected intravenously into three groups of C57Bl/6 mice ($5\times10^4$ cells/mouse, 3 mice per group). After two weeks the experiment was terminated, peripheral blood was collected, centrifuged and cell pellet was treated with red blood cell lysis buffer. EL4 cell levels were counted within the WBC fraction in mice not treated (NT), injected with scrambled siRNA or with mortalin specific siRNA.

Results:

As evident from the results (FIG. 5), EL4 cells constituted approximately 90% of the total WBC in the non treated and scrambled siRNA treated group (all cells were viable). However, transfection of EL4 cells with mortalin siRNA significantly reduced the growth of EL4 cells within the circulation of C57Bl/6 mice (*, P<0.05).

Example 6

Mortalin Specific siRNA Suppresses EL4 Tumor Growth in-vivo

Materials and Methods:

Tumor induction: Tumor induction was carried out by subcutaneously injecting EL4 cells into two groups of C57Bl/6 mice (1×10³ cells/mouse, 5 mice per group). Tumor size was measured by a Caliper.

Effect of mortalin specific siRNA on tumor growth: When the tumor size reached approximately 0.5 cm², siRNA directed to mouse mortalin (mot-2, SEQ ID NO: 348) mRNA or control non-specific scrambled siRNA (control, SEQ ID NO: 350) was injected into the tumor mass (30 nmol/0.1 ml). Tumor size was measured over a period of 12 days before the experiment was terminated. The size of the tumor was monitored by Caliper measurements.

Figure 6:
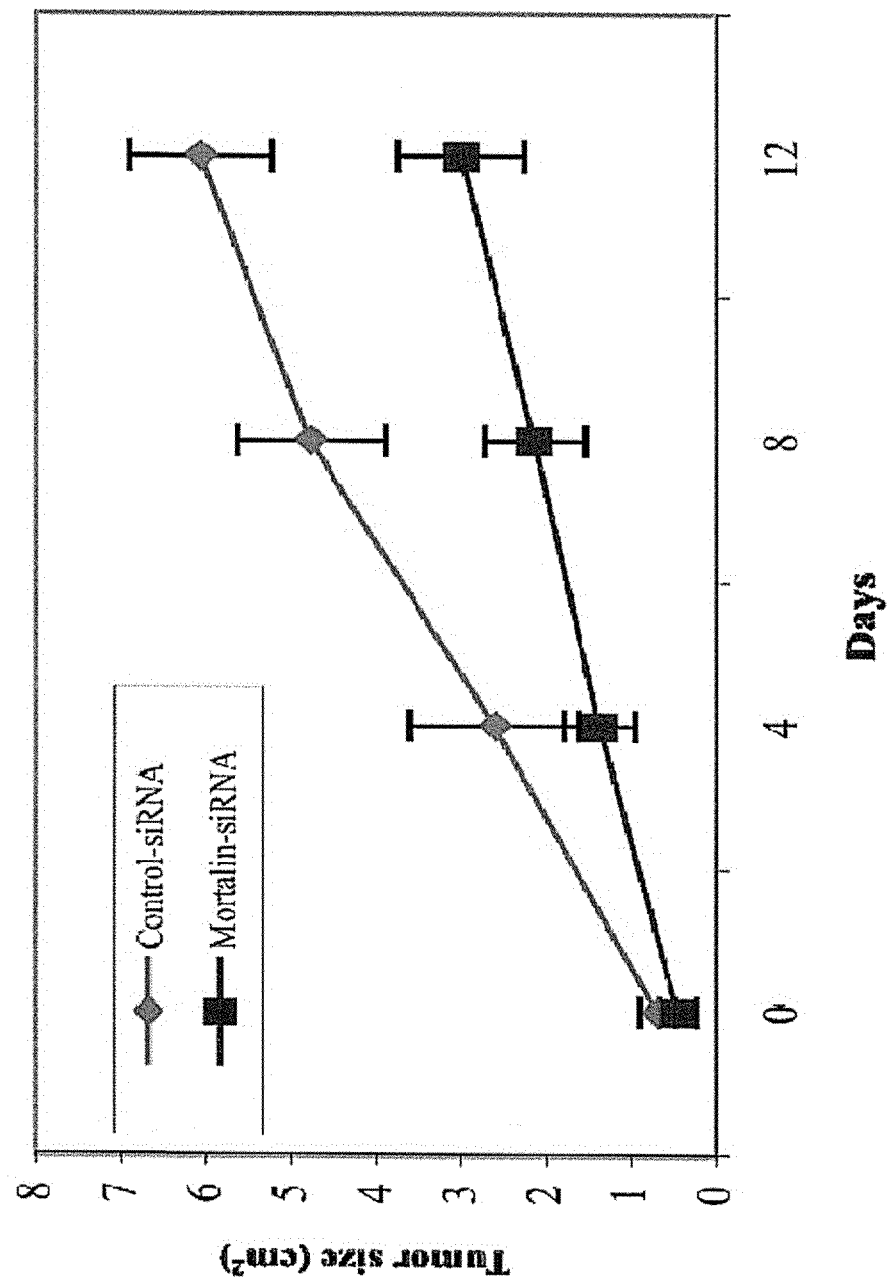
FIG. 6 is a line graph depicting reduced tumor growth by intratumoral injection of mortalin specific siRNA. The results show EL4 cells subcutaneously injected into two groups of C57Bl/6 mice ($1\times10^3$ cells/mouse, 5 mice/group). When tumor size reached approximately 0.5 $cm^2$, siRNA directed to mouse mortalin (mot-2, SEQ ID NO: 348) mRNA or control non-specific scrambled siRNA (control, SEQ ID NO: 350) was injected into the tumor mass (30 nmol/0.1 ml). Tumor size was measured over a period of 12 days by a Caliper.

Results:

As shown in FIG. 6, injection of mortalin specific siRNA directly into the tumor significantly reduced tumor size (*, P<0.05).

Example 7

Antibody Based Therapy Suppresses DHL-4 Tumor Growth in-vivo

Materials and Methods:

Tumor induction: 14 nude mice were injected subcutaneously with $2 \times 10^6$ DHL-4 human B lymphoma cells. Tumor size was measured by a Caliper.

Effect of Rituximab/Mabthera (anti-CD20 mAb) on tumor growth: When tumor size reached about 0.4 cm², the mice were divided into two groups (7 mice in each group). One group received two intraperitoneal injections of Rituximab/Mabthera (2.5 mg/mouse; Roche) at 5 days interval. The control group received pure human IgG. Tumor size was measured by Caliper.

Figure 7:
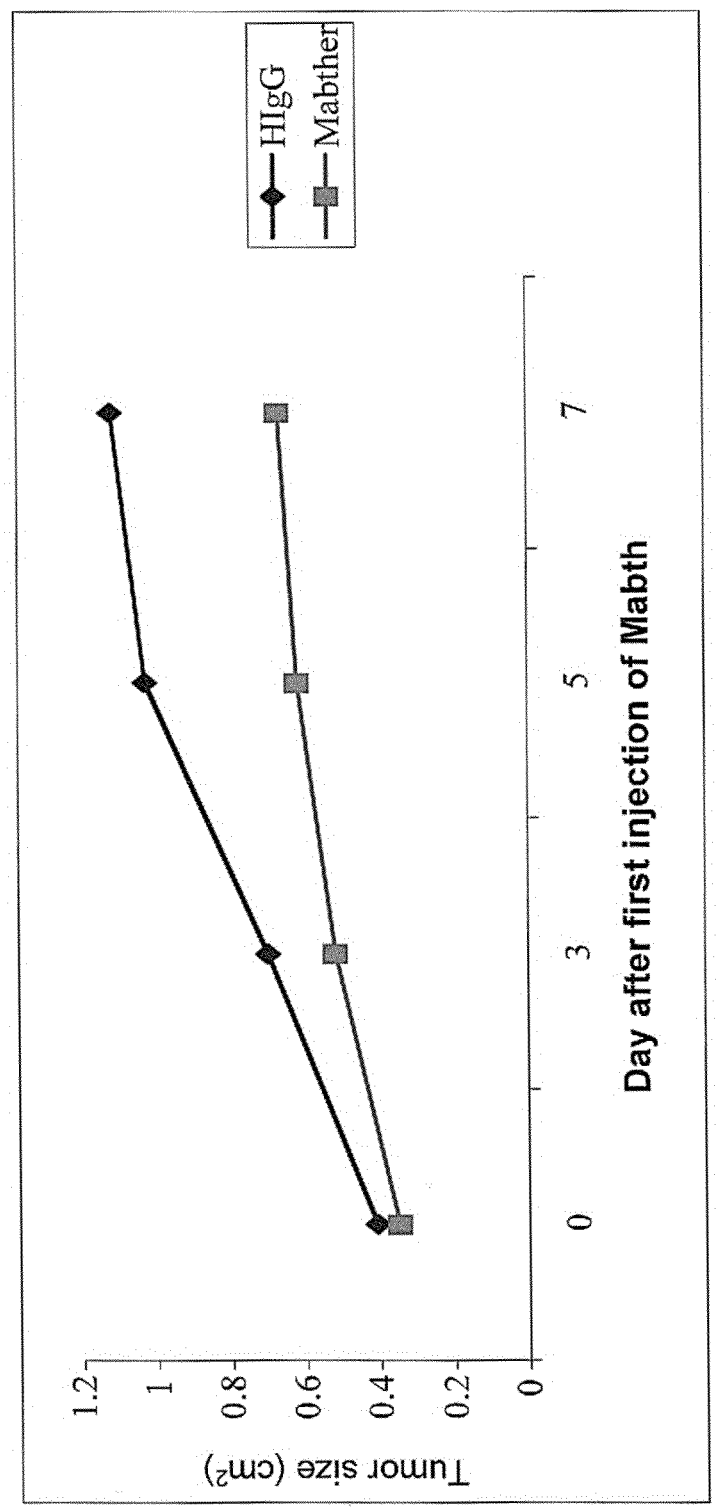
FIG. 7 is a line graph depicting reduced tumor growth by intraperitoneal injections of Rituximab/Mabthera (anti-CD20 mAb). The results show DHL-4 cells injected subcutaneously into nude mice. When tumor size reached about 0.4 $cm^2$, the mice were divided into two groups (7 mice each). One group received two intraperitoneal injections of Rituximab/Mabthera at 5 days interval. The control group received pure human IgG (HIgG). Tumor size was measured by Caliper.
Figure 8:
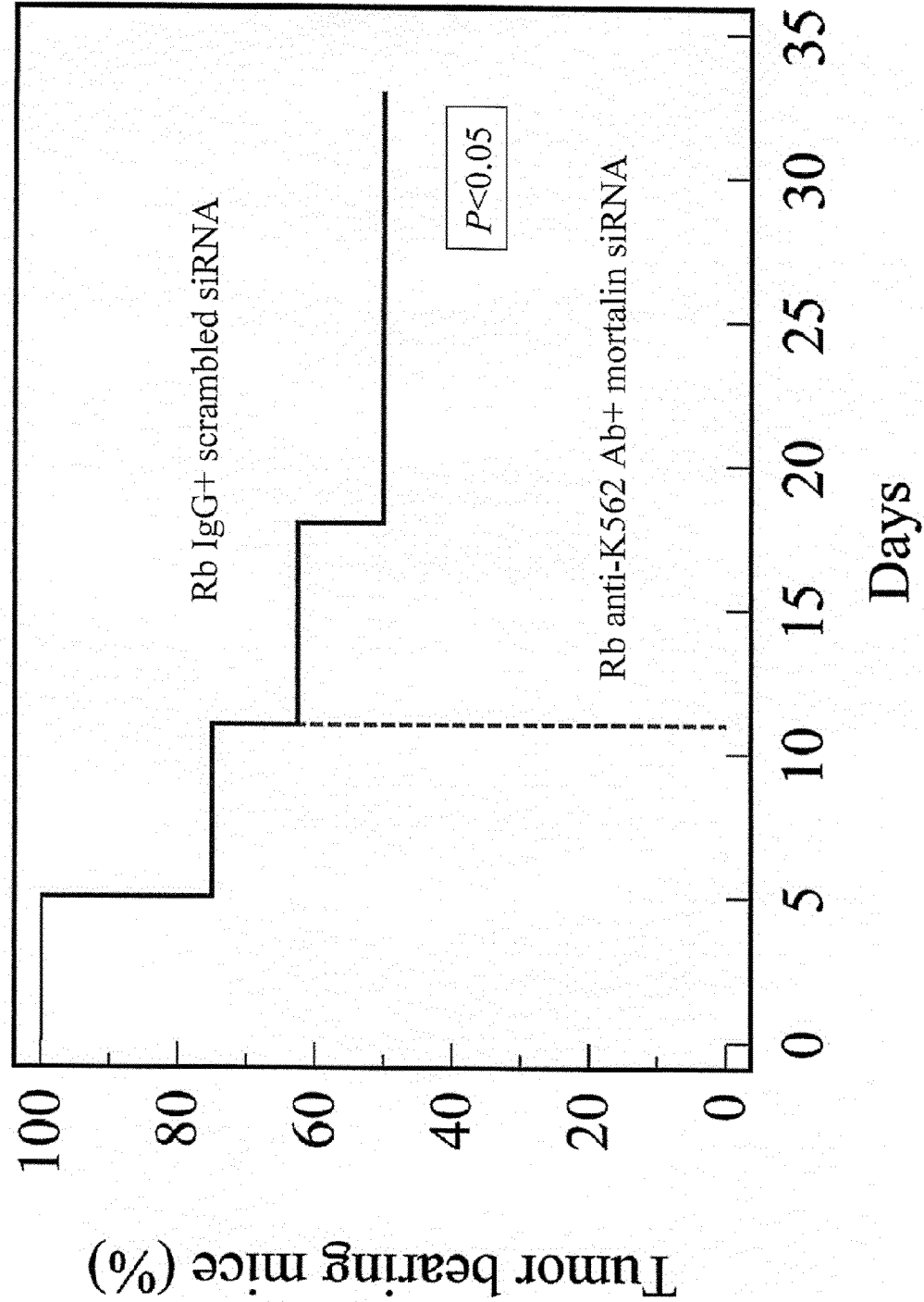
FIG. 8 depicts combined therapy with tumor specific antibody and siRNA specific to mortalin. The results show K562 cells implanted subcutaneously into nude mice. When tumors reached about 0.5 $cm^2$ in diameter, mice were divided into two groups (8 mice/group). The first group (depicted by dashed line) was treated with combined mortalin-siRNA (15 nmol/mouse, intravenously) and rabbit anti-K562 IgG (300 pg/mouse, intraperitoneally). The second group (control group, depicted by solid line) was treated with scrambled-siRNA and normal rabbit IgG as control. Treatments were given three times in intervals of 3 days between each treatment. The mice were examined every 2-3 days for tumor growth. Tumor size was measured by Caliper. Tumor size was analyzed by Kaplan-Meyer analysis and was found to be significant ($P<0.05$).

Results:

As evident from FIG. 7, intraperitoneal injections of Rituximab/Mabthera delayed the growth rate of DHL-4 human B lymphoma cells in nude mice.

Example 8

Combination Therapy (siRNA and antibody) Leads to in-vivo Tumor Regression

Materials and Methods:

K562 human chronic myeloid leukemia cells ($6 \times 10^6$ cells) were implanted subcutaneously into nude mice. When the tumors reached about 0.5 cm² in diameter, the mice were divided into two groups (8 mice/group). The first group was treated with combined mortalin specific siRNA (SEQ ID NO: 348, 15 nmol/mouse, intravenously) and rabbit anti-K562 IgG (300 pg/mouse, intraperitoneally, rabbit anti-K562 antibodies prepared by inventors). The second group (control group) received scrambled siRNA (SEQ ID NO: 350) and normal rabbit IgG. Treatments were given three times in intervals of 3 days between each treatment. The mice were examined every 2-3 days for tumor size.

Results:

Five days after the last treatment, two mice from each treatment group demonstrated complete regression of the tumor. However, 11 days after the last treatment all mice treated with combined therapy of siRNA specific to mortalin and antibody (anti-K562 antibody) showed complete tumor regression. At the same time, in the control group treated with scrambled siRNA and normal rabbit IgG, one additional mouse underwent tumor regression on day 11 and an additional mouse underwent tumor regretion on day 18. The tumors in the 4 remaining control mice progressively developed until day 33 (when the experiment was terminated). Kaplan-Meyer analysis of the data indicated a significant difference (P<0.05) between the treated and control groups.

Taken together, the results demonstrated that combined treatment with anti-tumor antibody and mortalin specific siRNA led to complete regression of the tumors in 8 out of 8 mice within 11 days. In the control group, treatment led to regression in 4 out of 8 mice within 18 days, while 4 out of 8 mice had developed progressive disease until day 33 when the experiment was terminated (in order to minimize suffering of the mice as these tumors would have most likely lead to their death.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims. All publications, patents, and patent applications and sequences identified by their GenBank accession numbers mentioned in this specification are herein incorporated in their entirety by reference into the specification, to the same extent as if each individual publication, patent, or patent application or sequence identified by its GenBank accession number was specifically and individually indicated to be incorporated herein by reference. In addition, citation or identification of any reference in this application shall not be construed as an admission that such reference is available as prior art to the present invention.

What is claimed is:

1. A method of decreasing vesicular shedding of complement from cancer cells and increasing complement-mediated cytolysis of cancer cells in a subject, thereby augmenting the cytolytic effect of antibodies that bind to cancer cells and recruit complement thereto, the method comprising:
administering to the subject antibodies that specifically bind the cancer cells and have a constant region capable of initiating complement-mediated cytotoxicity; and
administering a mortalin-specific siRNA molecule as set forth in SEQ ID NO: 192,
wherein said siRNA molecule is administered in an amount sufficient to decease the level of expression of mortalin in said cancer cells, thereby decreasinge vesicular shedding of complement from cancer cells and increase complement mediated cytolysis of said cancer cells, thereby augmenting the cytolytic effect of said antibodies on said cancer cells in the subject, and wherein said cancer cells are leukemic cells.

* * * * *